(12) United States Patent
Wilbur et al.

(10) Patent No.: US 7,141,676 B1
(45) Date of Patent: Nov. 28, 2006

(54) WATER SOLUBLE MULTI-BIOTIN-CONTAINING COMPOUNDS

(75) Inventors: D. Scott Wilbur, Edmonds, WA (US); Pradip M. Pathare, Seattle, WA (US); Donald K. Hamlin, Payuallup, WA (US); Feng Wan, Seattle, WA (US)

(73) Assignee: University of Washington, Seattle, WA (US)

( * ) Notice: Subject to any disclaimer, the term of this patent is extended or adjusted under 35 U.S.C. 154(b) by 392 days.

(21) Appl. No.: 10/261,040

(22) Filed: Sep. 30, 2002

Related U.S. Application Data

(63) Continuation-in-part of application No. 09/324,267, filed on Jun. 2, 1999, now abandoned, which is a continuation-in-part of application No. 08/798,413, filed on Feb. 7, 1997, now abandoned.

(60) Provisional application No. 60/011,321, filed on Feb. 8, 1996.

(51) Int. Cl.
*C07D 235/02* (2006.01)

(52) U.S. Cl. .......... 548/303.7; 424/1.65; 424/DIG. 16; 424/1.11

(58) Field of Classification Search .............. 424/1.65, 424/1.11, 1.45, DIG. 16; 435/7.5, 111; 548/303.7, 548/304.1; 514/387
See application file for complete search history.

(56) References Cited

U.S. PATENT DOCUMENTS 5,521,319 A * 5/1996 Huber et al. ............. 548/364.1
5,714,166 A * 2/1998 Tomalia et al. ............ 424/486

* cited by examiner

*Primary Examiner*—Dameron L. Jones
(74) *Attorney, Agent, or Firm*—Mueller and Smith, LPA

(57) ABSTRACT

Water-soluble discrete multi-biotin-containing compounds with at least three (3) biotin moieties are disclosed. The water-soluble biotin-containing compounds may additionally comprise one or more moieties that confer resistance to cleavage by biotinidase or that is cleavable in vitro or in vivo. The discrete multi-biotin-containing compounds may include a reactive moiety that provides a site for reaction with yet another moiety, such as a targeting, diagnostic or therapeutic functional moiety. Biotinylation reagents comprising water-soluble linker moieties are also disclosed and may additionally comprise a biotinidase protective group. Methods for amplifying the number of sites for binding biotin-binding proteins at a selected target using multi-biotin compounds also are disclosed.

13 Claims, 2 Drawing Sheets

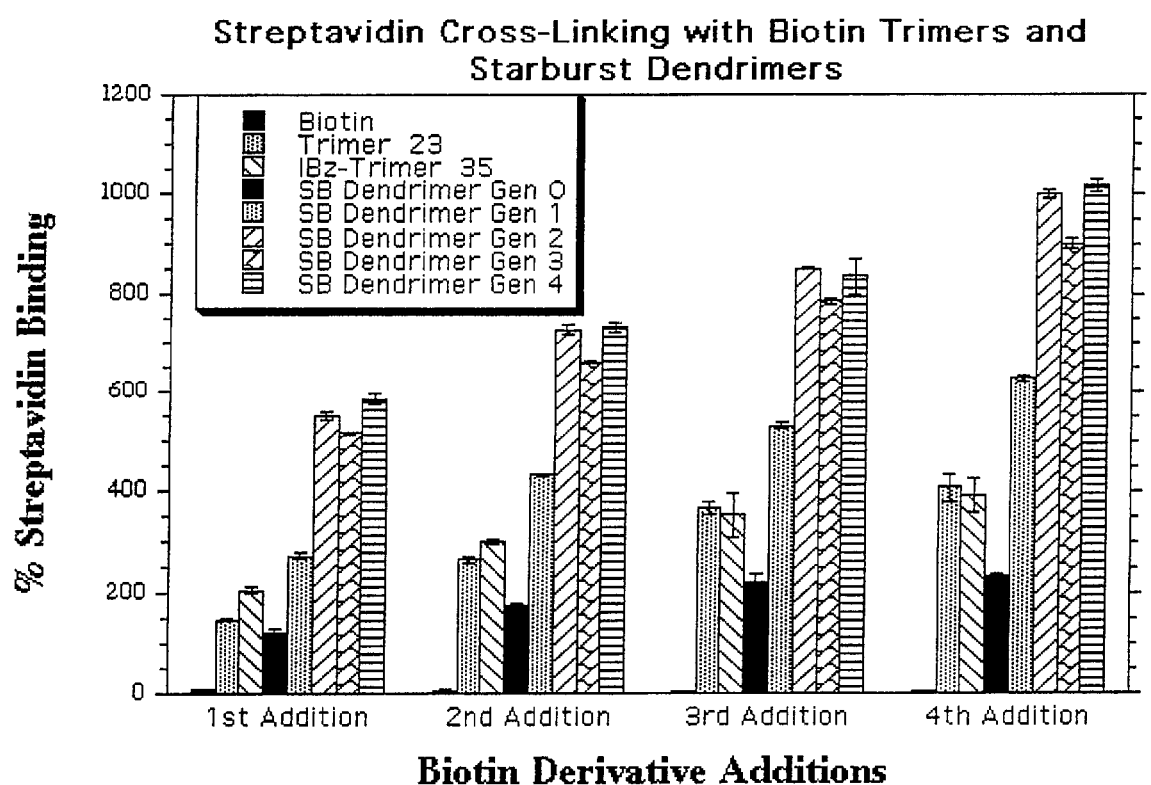

US 7,141,676 B1

WATER SOLUBLE MULTI-BIOTIN-CONTAINING COMPOUNDS

CROSS-REFERENCE TO RELATED APPLICATIONS

This application is a continuation-in-part of application Ser. No. 09/324,267, filed Jun. 2, 1999, now abandoned, which was a continuation-in-part of application Ser. No. 08/798,413 filed Feb. 7, 1997, now abandoned, which claims priority from U.S. Provisional Patent Application No. 60/011,321, filed Feb. 8, 1996.

FIELD OF THE INVENTION

The present invention relates generally to discrete multi-biotin-containing compounds, biotinylation reagents, and methods for synthesizing such compounds and reagents. More specifically, the present invention relates to discrete biotin-containing compounds with at least three (3) biotin moieties, and to biotinylation reagents suitable for in vitro and in vivo applications which biotinylation reagents are soluble in aqueous media and preferably resistant to biotinidase. The biotin-containing compounds additionally may comprise constituents that confer other functionalities, such as conjugation sites for diagnostic or therapeutic moieties. The compounds according to the invention may also comprise reporter moieties (e.g., fluorophores) that can be used to determine the number of multi-biotin species that have been attached to a functional moiety such as an antibody.

BACKGROUND OF THE INVENTION

The very strong interaction of biotin with the proteins avidin and streptavidin renders biotin-containing compounds useful for numerous applications. For example, many diagnostic tests use biotinylated derivatives. The widely used enzyme linked immunosorbent assay (ELISA), which was developed as an alternative to radioimmunoassays, employs biotinylated antibodies. Other biotinylated compounds have been used as probes and biotinylated nucleic acids have also been widely used. Purification techniques such as affinity chromatography frequently employ biotinylated materials.

More recently, biotin derivatives have been used in diagnosis and therapy of human disease. Notably, investigators have shown that use of a combination of monoclonal antibodies, streptavidin and/or avidin, and radiolabeled biotin derivatives, improves the diagnostic and therapeutic characteristics of the radiolabeled monoclonal antibody tumor targeting system. An example would be the "pre-targeting" of monoclonal antibody conjugates using the biotin/(strept) avidin ligand/anti-ligand pair for imaging and therapy of cancer.

One disadvantage of using biotin derivatives for many of these applications is their generally low solubility in aqueous media. In many examples, biotin derivatives and biotinylation reagents generally need to be solubilized in organic solvents or a medium comprising a substantial level of organic constituents to attain aqueous solubility. Insolubility of biotin derivatives and biotinylation reagents in aqueous solutions is particularly problematic for in vivo applications where organic solvents cannot be used.

It has been recognized that the availability of biotin derivatives for binding with avidin- and streptavidin-containing compounds may be greater when a spacer molecule is used between the biotin moiety and the other moieties to which the biotin is attached. The spacer molecules previously used have generally possessed low solubility in aqueous medium. Such spacer molecules reduce the aqueous solubility of the biotin-containing compound. In addition to causing solubility problems, the lipophilic nature of the biotin derivatives with spacer molecules of low water solubility may cause them to associate with blood components, rendering their biological half-life in in vivo applications longer than desired. Prior investigators have attached water solubilizing moieties to biotin and to compounds containing two biotin moieties, however, the prior art has failed to disclose or suggest biotin-containing compounds that comprise at least three (3) biotin moieties which are resistant to the enzyme biotinidase.

Heretofore, U.S. Pat. Nos. 5,541,287 and 5,578,287 disclose compositions for use in pre-targeted delivery of diagnostic and therapeutic agents, which compositions employ biotin/avidin as the ligand/anti-ligand binding pair. These patents disclose that the 1,4,7,10-tetraazacyclododecane-N, N',N'',N'''-tetra acetic acid (DOTA)-biotin adducts have desirable in vivo biodistribution and are cleared primarily by renal excretion. However, these patents only teach biotin-containing compounds of up to two (2) biotin moieties. These patents also report that the disclosed adducts are not stable in serum due to the presence of biotinidase. Poor in vivo stability therefore limits the use of such conjugates in therapeutic applications.

U.S. Pat. No. 5,326,778 discloses conjugates of biotin and deferoxamine for radioimmunoimaging and radioimmunotherapy, which conjugates are capable of binding metal ions to avidin or streptavidin. This patent fails to suggest a biotin-containing compound that contains at least three (3) biotin moieties and water-solubilizing moieties of 6 to 50 atoms in length.

U.S. Pat. No. 5,482,698 discloses a method for the detection and therapy of lesions with biotin/avidin polymer conjugates. The preferred polymers are the starburst dendrimers or dextrans. This patent, however, does not suggest water-soluble linker moieties of 6 to 50 atoms in length and biotinidase blocking groups in a discrete multi-biotin-containing compound. This reference also fails to suggest how dendrimers and dextrans can be used to produce discrete, water-soluble, multi-biotin-containing compounds.

U.S. Pat. No. 5,521,319 teaches that biotin compounds, which comprise water-soluble linkers, can be conjugated to various moieties; however, there is no suggestion that three (3) or more biotin moieties be present in the compound and that biotinidase blocking groups be incorporated to impart in vivo stability.

U.S. Pat. No. 5,750,357 describes a detectable synthetic copolymer wherein one monomer is a binding agent for microorganisms and the second monomer is a detectable label or a binding site for a detectable label, such as biotin. The polymerization of these two monomers results in a random co-polymer that may contain three (3) or more biotin moieties. However, there is no suggestion or disclosure that each biotin moiety be linked to a water-soluble moiety of 6 to 50 atoms in length, which in turn is linked to a cross-linker compound that has at least tri-functionality, such as benzene 1,3,5-tricarbonyl trichloride, starburst dendrimers, cascade dendrimers, polylysine, polyglutamic acid, and polyaspartic acid. The thermally initiated random polymerization disclosed produces a reaction mixture that consists of numerous polymeric species with varying molecular weights and number of biotin moieties. Such random biotin-containing compounds have a very limited utility in diagnostic and therapeutic applications. Further, this patent does not address the need for a biotinidase blocking moiety.

Hnatowich, et al., in "Investigations of Avidin and Biotin for Imaging Applications", *J. Nucl. Med.*, Vol. 28, pp. 1294–1302, No. 8 (1987), discloses a biocytin-DTPA-biotin dimer reaction product. This reference, however, does not suggest a compound comprising at least three (3) biotin moieties, water-soluble linker moieties of 6 to 50 atoms in length, and biotinidase protective moieties.

Biotinylated dextrans have been proposed as molecular probes by, for example, R. P. Haugland, *Handbook of Fluorescent Probes and Research Chemicals*, Sixth Edition, Chapter 15.5, Molecular Probes, Inc., Eugene, Oreg. These probes are not discrete molecular entities and do not address the need for resistance to biotinidase activity, nor do they suggest the use of water-soluble linker moieties of 6 to 50 atoms in length.

It is apparent, then, that the prior art has paid little attention to the water solubility of biotin-containing compounds, or the synthesis of biotin reagents having three (3) or more biotin moieties and resistance to biotinidase. Because biotin-containing compounds are of increasing interest for diagnostic and therapeutic applications, there is a need for enhanced biotin-containing compounds exhibiting excellent water solubility and improved resistance to cleavage by the serum enzyme biotinidase. The compounds according to the invention meet these needs, in part, through the selection of water-soluble linkers that allow for the optimum binding of the biotin moiety to avidin/streptavidin.

BRIEF SUMMARY OF THE INVENTION

One aspect of the present invention is directed to discrete multi-biotin-containing compounds that are useful in vivo to amplify a signal or increase the amount of material bound to a site. As used herein, the term "discrete" means a singular molecular entity and not a mixture of molecular entities (such as those resulting from a random polymerization reaction or a random labeling reaction). For example, the amount of radioactivity presented to a cancer cell that has been labeled with an antibody can be greatly increased through the use of multi-biotin-containing compounds according to the invention.

Thus, there is disclosed a biotin-containing compound, which is a discrete biotin-containing compound of the general structural formula (1):

C-(L-P-B)$_n$.     (A)

In structure (A), C is a multifunctional cross-linking moiety having discrete size and containing n substituents, which are reactive, or can be made reactive, with L. The "cross-linkers", C, can be one or more of an at least tri-functional aromatic compounds (e.g., benzenes), starburst dendrimers, or cascade dendrimers. Representative cross-linkers of at least tri-functionality useful in the present invention include, for example, polycarboxyl and polyamine compounds with 3 to 64 functional groups, discrete polylysine, polyglutamic acids, and polyaspartic acids. Functionality also can be added to C to make C reactive with other molecules. Such functionality includes, for example, active esters, isothiocyanates, maleimides, disulfides, combinations thereof, and the like.

In structure (A), the water-soluble linker, L, is selected from water-soluble linker moieties of discrete size being between 6 to 50 atoms in length. The "water-soluble linker" (L) can be one or more of alkyl, heteroalkyl, aryl, or heteroaryl linker moieties, which moeties contain one or more of ethers, hydroxyls, amines, thioethers, thiols, esters, maleimides, iodoacetamides, hydroxylamines, acyl hydrazines, carboxylic acids, polyphosphoric acids, phenols, sulfonic acids, iodoacetamides, aldehydes, nitrophenylazides, polylysines, ammoniums, amides, ketones, decaboranes, dodedaboranes, boranes, closo- or nido-carboranes.

In structure (A), P is a biotinidase protective group that blocks biotinidase activity. The "biotinidase protective group", P, reduces the effectiveness of biotinidase to cleave the biotin moiety from the molecule of the invention. P can be one or more of α-amino acids, N-methyl moieties, α-alkyl moieties, or aryl moieties.

In structure (A), B is selected from biotin moieties, including modified biotin moities. The "biotin moiety", B, can be one or more of desthiobiotin, biotin sulfone, iminobiotin, alkylated biotins, or acetylated biotins.

In structure (A), n ranges from 3 to 64.

There is also disclosed a biotin-containing compound of the structural formula:

C-(L-B)$_n$     (B)

wherein C, L, B and n are defined as above.

There is further disclosed a biotin-containing compound of the structural formula:

T$_m$-C-(L-B)$_n$     (C)

wherein C, L, B and n are defined as above, m is 1 to 5; and T is selected from a therapeutic, diagnostic or other active moieties, such as, for example targeting molecules. Representative "T" moieties include those chemical entities that:
 1) carry diagnostic and/or therapeutic radionuclides;
 2) are diagnostic and/or therapeutic photoactive molecules;
 3) are chemotherapeutic agents, or precursors or prodrugs thereof;
 4) are protein toxins or derivatives thereof;
 5) target tumors through a variety of receptor modalities;
 6) bind with biologically active proteins;
 7) cause the molecule to be excluded from cells;
 8) allow the molecule to enter cells; or
 9) cause it to target infections.

More specifically, the "T" moiety may be, for example, a molecule chelated to or bound with a radionuclide (e.g., I-123, I-125, I-131, In-111, Y-90, At-211, Bi-213, etc); a photoactive group (e.g., dansyl, fluorescein, cyanocobalamin, cyanine dye, porphyrin, etc.); a drug (e.g., dehydrotestosterone, adriamycin, vincristine, 5-fluorouracil, etc.); a cancer targeting agent (e.g., monoclonal antibody or fragment, growth factor, signaling peptide, etc.); an MRI active agent (e.g., chelated gadolinium (Gd), fluorinated compounds, boron-11 compounds, etc); a neutron activated molecule (e.g., boron-10 containing molecules, Gd containing molecules, etc.); or a membrane crossing agent (e.g., tranferrin, folate, cyanocobalamin, etc.).

There also is disclosed a functionalized biotin-containing compound of the structural formula:

T-C-(L-P-B)$_n$     (D)

wherein T, C, L, P, B and n are defined as above.

There further is disclosed a multi-biotin-containing compound of the structural formula:

T$_m$-C-(L-(P)$_y$-B)$_n$     (E)

wherein C is a cross-linker of at least tri-functionality being one or more of discrete tri-functionalized aromatic compounds, polycarboxylic compounds, polyamino compounds, starburst dendrimers or cascade dendrimers. L is a water-soluble moiety being between 6 to 50 atoms in length that is one or more of ethers, hydroxyls, amines, thioethers and thiols. P is a biotinidase protective group being one or more of a-amino acids, N-methyl moieties, α-alkyl moieties, or aryl moieties. y is 0 or 1. B is a biotin moieties. n can range from 3 to 64, preferably 3 to 32. T is a therapeutic or diagnostic moiety. m can range from 1 to 5.

In preferred embodiments of the invention, the water-soluble linker moieties are one or more of 4,7,10-trioxa-1, 13-tridecanediamine or 12-N-methylamino-4,7,10-trioxa-dodecanoic acid. As disclosed above, the biotin-containing compound also may comprise diagnostic and therapeutic moieties joined to the compound.

Also disclosed is a non-polymerized biotin-containing compound comprising at least three (3) biotin moieties joined by water-soluble linker moieties to a dendrimer, wherein said linker moieties are between 8 to 20 atoms in length.

In yet another embodiment, the present invention is a novel biotinylation reagent that may be used to prepare the multi-biotin-containing compounds of the invention. The biotinylation reagent has the structural formula:

$$X\text{-}R\text{-}C\text{-}(L\text{-}P\text{-}B)_n \qquad (F)$$

wherein B, P, L, C, and n are defined as above. The purpose of R is to separate the multi-biotin core (L-P-B) from another molecule (e.g., biomolecule) so that steric encumbrance does not interfere with the binding of avidin, streptavidin or other biotin binding protein. Additionally, the spacer, R, moves the multi-biotin conjugate away from a biomolecule such that it is less likely to interfere with natural function of that biomolecule (such as, for example, binding with a receptor). To that end, R may be C, L, or other molecule that binds/reacts with C and X. In fact, R may not be required for some C's and, therefore, is optional in structure (F).

X is a reactive functionality or a precursor thereof carried by R, which can be C or any other molecule reactable with C. Representative reactive functionalities, X, include, but are not limited to, nucleophilic groups, including one or more of amines, sulfhydryl groups or alkoxides; and electrophilic groups, including one or more of activated carboxylates, mixed anhydrides, isothiocyanates, isocyanates, ketones, aldehydes, α,β-unsaturated ene-one moieties, alkyl halides, benzyl halides or similar functional groups with or without protecting moieties on them, wherein these chemical protecting moieties are not the enzymatic protective groups "P" as defined herein. Activated carboxylates include, for example, N-succinimidyl esters, tetrafluorophenyl esters, and similar moieties as described in the literature. The chemical protecting groups include, for example, t-butyloxycarbonyl (t-Boc), t-Bu esters, benzyloxycarbonyl (Z), phthalimidio, fluorenylmethyloxycarbonyl (Fmoc), and similar moieties described in the literature.

The present invention additionally relates to a biotin-containing compound comprising at least three (3) biotin moieties joined to at least three water-soluble linker moieties of between 8 to 20 atoms and a cross-linking agent of at least tri-functionality. In a preferred embodiment, the water-soluble linker moiety comprises one or more moieties being one or more of polyether, polyhydroxyl, or polyamino moieties.

In a preferred embodiment, the multi-biotin-containing compound has water solubility greater than 0.2 mg/mL at neutral pH and ambient temperature. Still more preferred, the multi-biotin-containing compound has water solubility greater than 1 mg/mL at neutral pH and ambient temperature, and most preferably a water solubility greater than 5 mg/mL.

As thus disclosed, the multi-biotin-containing compounds of the present invention are prepared by reacting a biotin molecule with water-soluble linker moieties to form biotin/water-soluble linker adducts. The biotin/water-soluble linker adduct preferably also comprises a biotinidase protective group between the biotin moiety and the water-soluble linker. This molecule then is bonded to a cross-linker that possesses at least tri-functionality to result in a discrete molecular entity that comprises three (3) or more biotin moieties. Such biotin-containing compounds preferably comprise one or more protective groups that confer resistance to cleavage by biotinidase and a reactive or functional moiety that provides a site for reaction with yet another moiety, such as a targeting, diagnostic, or therapeutic moiety.

BRIEF DESCRIPTION OF THE DRAWINGS

For a fuller understanding of the nature and advantages of the present invention, reference should be had to the following detailed description taken in connection with the accompanying drawings, in which:

FIG. 2 illustrates the results of the experiments described in Example 12, demonstrating the successful cross-linking of streptavidin with biotin dendrimers.

Figure 1:
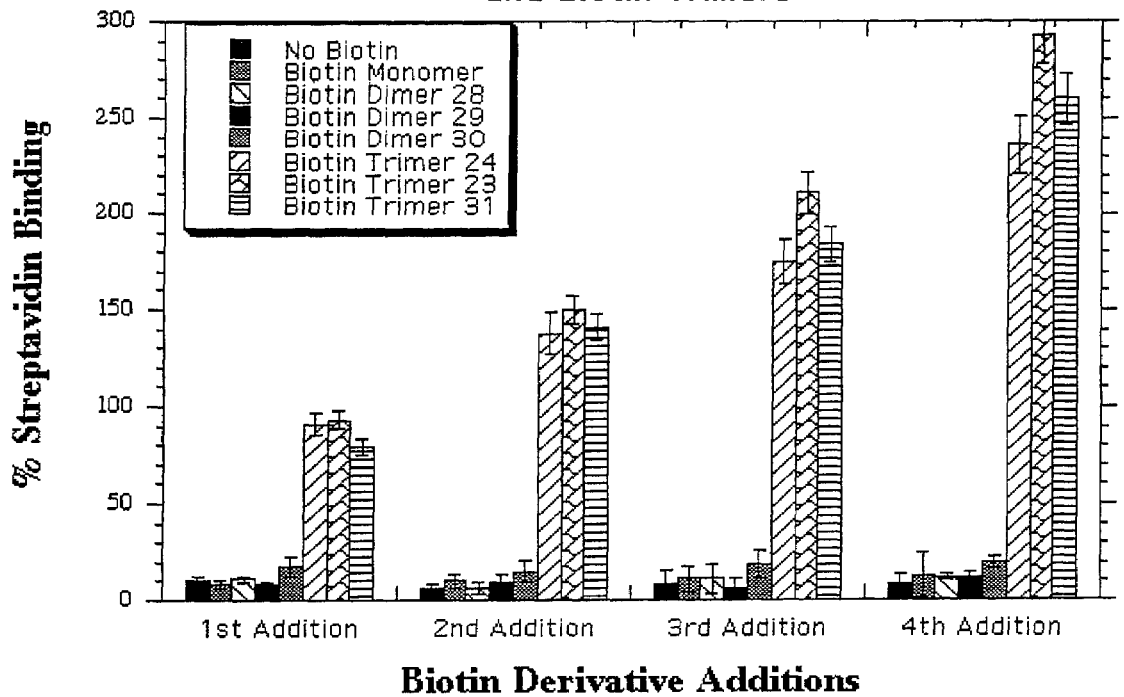
FIG. 1 graphically illustrates the percentage streptavidin binding of the biotin monomer and the dimers and trimers as a function of sequential biotin compound additions as described in connection with Example 7.

The drawings will be described in greater detail below.

DETAILED DESCRIPTION OF THE INVENTION

Most of the science and application of polymer chemistry is focused in the area of understanding and "controlling" the tremendous range of variables that affect the molecular weight distribution of the resultant polymers. This applies even to the simplest formulations and the best chemistries found to date to narrow this weight distribution. The nature of the polymer process will never result in the making of a single pure component. Reference is made to an introductory text in polymer chemistry such as, inter alia, Dr. George Odian's, *Principles of Polymerization*, (ISBN 0-471-05146-2), to fully appreciate the complexity of the science of "controlling" molecular weight distribution of polymers.

Most polymers are analyzed to determine their PDI, which represents their polydispersity index or the molecular weight distribution of the polymer sample. The common thermal- and photo-initiated acrylate polymerizations give PDI's at least >1.5, often as high as 20–50 (the higher the number the broader the distribution and the more different compounds in the sample). An idealized example cited in Odian's book (pg. 389) of a very narrow distribution has a PDI=1.002. For a polymer with an average MW of 500,000 having a Poison distribution, 95% of the individual polymer products have MW's between 450,000 and 550,000. If the monomer were styrene, with a MW of about 100, this would represent a mixture of at least 1,000 different compounds.

Actual polymerizations of this living anionic polymerization example for making MW "standards" have PDI's of 1.06–1.12.

The invention is directed to the production of discrete multi-biotin-containing compounds that are useful, for example, in vivo to amplify a signal or increase the amount of material bound to a site. The term "discrete" means a singular molecular entity and not a mixture of molecular entities (such as those resulting from a random polymerization reaction or a random labeling reaction). The discreteness of the inventive biotin compounds distinguishes them from the art.

Naturally occurring biotin, illustrated below as structure 1, in conjugated form is useful for many different applications as a result of its strong binding affinity with the proteins avidin and streptavidin.

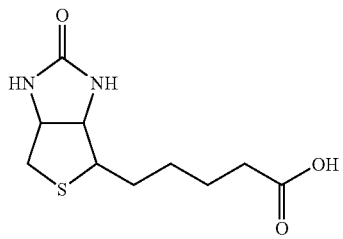

1

Many modified forms of biotin have been synthesized for various applications and are useful in the present invention as the biotin moiety, B, in addition to natural biotin. Modifications of biotin at positions other than the carboxylate group, for example, provide molecules that have weaker interactions with avidin or streptavidin. Such modified biotin molecules, such as desthiobiotin shown below as structure 2, and biotin sulfone shown below as structure 3, are useful for some applications because they bind tightly enough to provide a strong association, yet they bind in a reversible fashion such that they can be displaced by tighter binding biotin derivatives (e.g., structure 1). Other modifications of biotin, such as conversion of the ureido functionality to an guanidinium functionality (e.g., iminobiotin, shown below, structure 4) or conversion of the amide-NH by alkylation (e.g., methylation) or by acylation (e.g., acetyl) produce biotins of varying binding strengths and can be the biotin moiety, B, of the compounds of the present invention.

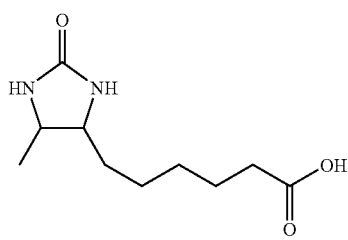

2

-continued

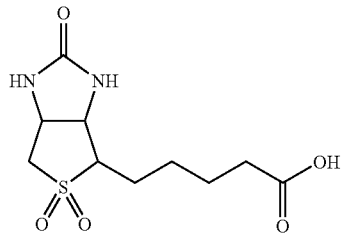

3

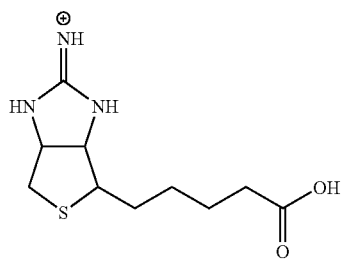

4

Modifications of biotin or biotin derivatives by reaction with amines of sterically bulky groups, such as proteins (e.g., insulin), or sterically small molecules, such as branched chain moieties including 2-dimethyl-amino compounds or amino-aryl moieties, also are advantageous for some applications. Preferred steric moieties that can be conjugated with the carboxylate of biotin, or a modified biotin, include substituted and unsubstituted aminobenzoic acids or aminomethylbenzoic acids. As stated above, the biotin moiety, B, includes naturally occurring biotin and modifications of naturally occurring biotin that bind to avidin, streptavidin, modifications thereof, and constituents thereof.

The solubility of naturally occurring biotin in water is approximately 0.2 mg/mL at neutral pH and ambient temperature. Prior art modified biotins generally have a lower water solubility than natural biotin, and the prior art biotin compounds having more than one modified biotin moiety per molecule generally are substantially insoluble in aqueous media. For example, a prior art biotin compound comprising two biotin moieties joined by an aliphatic 1,12-diaminododecane linker moiety has such low water solubility that routine HPLC analysis does not detect any dimers in aqueous solution.

The solubility of biotin moieties in aqueous media is enhanced according to the present invention by attaching a water-soluble linker moiety, typically through the carboxylate group of the biotin. Water-soluble linker moieties, L, according to the present invention, compromise any linker moiety that, when conjugated or coupled (e.g., covalently bonded) to a biotin moiety and the cross-linker, C, increases the water solubility of the biotin-containing compound. The biotin-containing compounds of the present invention typically have aqueous solubility of greater than 0.2 mg/mL at neutral pH and ambient temperature. Biotin-containing compounds and biotinylation reagents of the present invention preferably exhibit a water solubility of at least about 1 mg/mL at neutral pH and ambient temperature, and most preferably exhibit a water solubility of at least about 5 mg/mL at neutral pH and ambient temperature. Dissolving the compound in water, stirring the solution, and allowing the solution to stand at room temperature for about 24 hours determines solubility. The solution then is centrifuged and the resultant aqueous layer analyzed using high performance liquid chromatography ("HPLC"). The HPLC analysis is conducted with a gradient using acetonitrile or methanol and water as the solvent mixture on a reversed-phase column.

The linker, L, has two principal purposes: (1) act as a spacer molecule between the biotin and the cross-liner, C, and (2) act as a moiety to increase the water solubility when multiple biotin entities are present. The spacer distance is defined by the 6 to 50-atom length of L when it is in its extended linear form. To increase the water solubility, heteroatoms or functional groups, which form hydrogen bonds with water, are incorporated into, or appended onto, the atoms that make up the linker chain.

Water-soluble linker moieties, L, preferably comprise hydrophilic moieties (e.g., polar functional groups) including electronically neutral and charged (e.g., ionic) moieties. Suitable hydrophilic moieties include electronically neutral moieties containing polar functional groups (i.e., groups that contain atoms of differing electronegativity such as organic compounds containing nitrogen, oxygen, and sulfur) that increase their hydrophilicity. Typically, these neutral hydrophilic moieties contain functional groups that hydrogen bond with water. Such hydrogen bonding groups include, inter alia, ether (—O—), hydroxy (—OH), amino (—$NR_2$, —NHR, —$NH_2$), and to a lesser extent thioether (—S—), and thiol (—SH) groups.

Other polar functional groups that may serve as hydrophilic moieties include, for example, ethers and carbonyl-containing groups such as acids, esters, amides, ketones, and aldehydes. Moieties that comprise multiple polar functional groups are more hydrophilic than those moieties that comprise a single polar functional group. Suitable moieties comprising multiple polar groups include, for example, polyhydroxyl, polyamido, polyether, polyphosphoric acid, polyalcohol, and polyamine moieties. The polyhydroxyl moieties include, for example, glycols, glycerols, and polysaccharides including glucose, fructose, galactose, idose, inositol, mannose, tagatose, and N-methylglucamine. Polyether moieties include, for example, polyethylene glycol, penta(ethylene glycol), tetra(ethylene glycol), and tri (ethylene glycol). Polyamine moieties include, for example, polylysine, spermine, and spermidine. Representative polycarboxylates include, for example, polyglutamic acid and polyaspartic acid.

Suitable charged hydrophilic moieties become either formally negatively or positively charged in water. Suitable negatively charged moieties include, for example, acid anions resulting from the dissociation of acids in water. For example, carboxylic acids (COOH) dissociate to form negatively charged carboxylate ions ($CO_2^-$) at pHs of greater than about 5. Other stronger acids, such as phosphoric ($H_3PO_4$) and sulfonic ($H_2SO_3$) acids, ionize to form phosphate ($PO_4^{-3}$) and sulfonate ($SO_3^{-2}$) anions, respectively, at pHs of greater than about 2. Other more weakly acidic moieties, such as phenols and thiols, also may dissociate to form their corresponding anionic derivatives that also are water solubilizing. Other suitable negatively charged moieties include, for example, monocarbon carboranes, nido-carboranes, decaboranes, and dodecaboranes.

Depending upon the pH of the aqueous solution, basic moieties may become formally positively charged moieties in water. These moieties become highly water-soluble through protonation in aqueous solution. For example, at a pH lower than about 8, amines ($NR_2$, $NHR_2$, $NH_2$) become ammonium ions ($NHR_2^+$, $NH_2R^+$, $NH_3^+$), which are water-soluble moieties. Quaternary ammonium moieties (—$NR_3^+$) are water-soluble at all pHs. Suitable charged solubilizing moieties also include polylysine groups.

Water-soluble linkers preferably are relatively linear molecules greater than 4 atoms in length, preferably between 6 and 50 atoms in length, and most preferably about 8 to 20 atoms in length. In one preferred embodiment, the linker is a linear molecule of 12 to 15 atoms in length. In the context of the present invention, the term "atom" refers to a chemical element, such as C, N, O S, or the like. The number of atom ranges provided herein is based on the relatively linear accounting of the water-soluble linker. One of ordinary skill in the art will appreciate that a linker may be linear, branched, or ring structures, and may include combinations of these features.

Suitable water-soluble linkers comprise at least two coupling or reactive groups allowing the linker to bind to both a biotin moiety (with or without the protective group P) and at least the tri-functional cross-linker, C. Empirical factors, such as the size (e.g., molecular weight and molecular conformation) and the nature (e.g., charge and constituents) of the water-soluble linker moiety, will be dictated by the specific application of the biotin-containing compound, e.g., therapeutic or diagnostic.

The cross-linker, C, is a discrete chemical entity that provides a scaffolding with a defined number of functional groups that can be reacted with, or modified to react with, linker molecules, L, to ultimately obtain discrete multi-biotin molecules. To obtain the discrete nature of the inventive multi-biotin composition, reaction with L must be conducted in such a manner that all of the coupling functionalities on C (e.g., primary amine groups, activated esters, etc.) react; otherwise, mixtures of compounds will be obtained. The inventive multi-biotin composition only applies to those cross-linkers that are not mixtures of compounds produced in a polymerization process (i.e., they are of discrete size and form), and are not molecules (such as, monoclonal antibodies), which lose their binding affinity due to reaction with all of a particular type of functional group (e.g., primary amine or carboxylate) present on the molecule.

The cross-linker, C, may provide, in addition to the binding sites for the water-soluble linkers, one or more binding sites for one or more functional or target moieties. One of ordinary skill in the art will appreciate that this allows for any number of different molecules to couple with the biotin-containing compound, including, for example, markers, such as radiolabeled and fluorescent molecules; proteins and peptides, such as antibodies; and conjugating molecules. Suitable at least tri-functional linkers include, but are not limited to, benzene 1,3,5-tricarbonyl trichloride, starburst dendrimers, cascade dendrimers, polyamine compounds, and polycarboxyl compounds. Functionality also can be added to C to make C reactive with other molecules. Such functionality includes, for example, active esters, isothiocyanates, maleimides, disulfides, combinations thereof, and the like Two principal types of water-soluble linker moieties, L, are preferred for use in the biotin-containing compounds and biotinylation reagents of the present invention. One type is a non-ionized water-soluble linker, which is made more soluble by functional groups, such as, for example, ethers or hydroxyl groups. Non-ionized linker moieties render the biotin-containing compound more water-soluble, while retaining the neutral character of the biotin moiety. Particularly advantageous non-ionized linker moieties comprise chains with at least one ether moiety in them, and which are terminated with one or more amines, carboxylic acids, thiols, hydroxyl groups, or combinations of those functionalities. Examples of non-ionized soluble linker moieties are the commercially available molecules including, for example, 4,7,10-trioxa-1,13-tridecanediamine, 2,2'-(ethylenedioxy)diethylamine, and tetraethylene glycol. Thioether containing linker moieties also are advantageous in this application. It should be recognized that after conversion to the water-soluble linker, L, there will be no ionizable feature in the molecule.

In the preparation of the biotin-containing compounds according to the invention, the biotin moiety, B, typically is activated at a selected coupling site (e.g., carboxylic group) and the water-soluble linker, L, then is coupled to the biotin moiety to form a biotin moiety/water-soluble linker adduct. This adduct can be prepared using any one of several means, including, for example, an amide forming reaction, employing an amine group on the linker and the carboxylate coupling site on the biotin moiety. Alternatively, a water-soluble linker may be coupled to a biotin moiety through an amide forming reaction employing a carboxylate group on the water-soluble linker and an amino group on the biotin moiety. It should be noted that after forming the biotin/water-soluble linker adduct, B-L, this reaction product then is reacted with the cross-linker, C. As discussed below, it is sometimes advantageous to place a biotinidase blocking moiety, P, between B and L, thus forming a B-P-L structure.

The amide reaction to form the biotin/water-soluble linker adduct may include the use of coupling agents. Suitable coupling agents include, for example, carbodiimide coupling agents, such as 1-ethyl-3-(3-dimethylaminopropyl) carbodiimide hydrochloride (EDC), 1-benzyl-3-(3-dimethylaminopropyl)carbodiimide (BDC), 1-cyclohexyl-3-(2-morpholinyl-4-ethyl)carbodiimide (CMC), and 1,3-dicyclohexylcarbodiimide (DCC). Other suitable techniques are described in detail in Bodanszky, "Principles of Peptide Synthesis", *Springer Verlag,*. Berlin, 1984.

Generally, non-ionized water-soluble ether linking moieties can be bonded to biotin through the carboxylate (or activated carboxylate) functionality of a biotin moiety or through conjugation wherein the biotin carboxylate functionality has been reduced and activated towards reactions with nucleophiles. Detailed syntheses of representative biotin-containing compounds are set forth in the Examples below.

Some examples of useful biotin/moiety water-soluble linker adducts are shown below as structures 5–9.

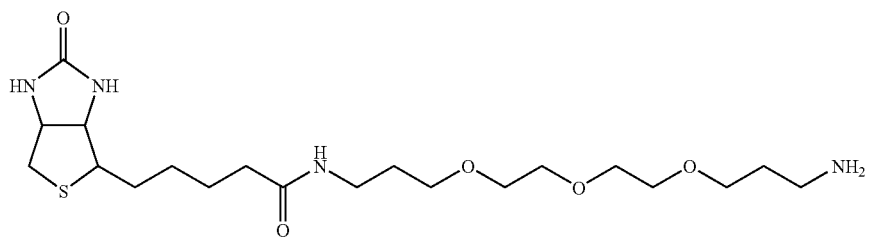

5

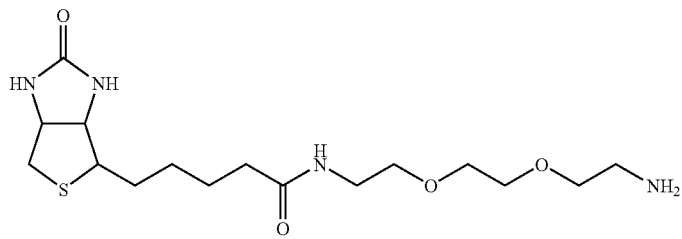

6

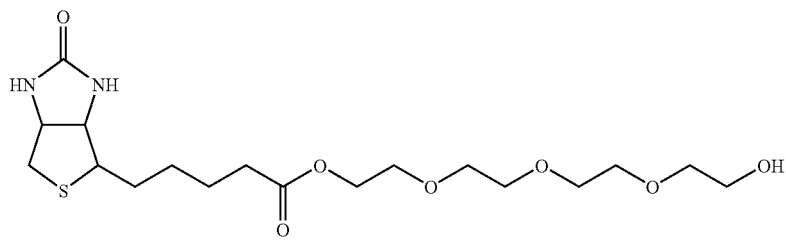

7

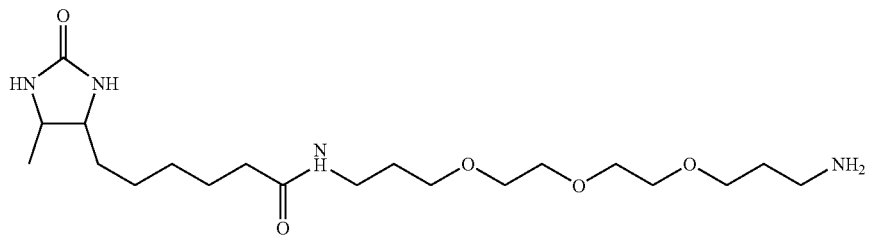

8

9

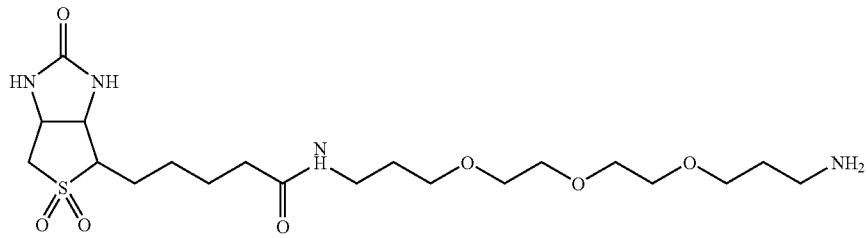

The water-soluble linker moieties also may contain other functional groups attached to or within the chain (e.g., amides) as illustrated in structures 10 and 11 and may be synthesized in a sequential step of reactions.

10

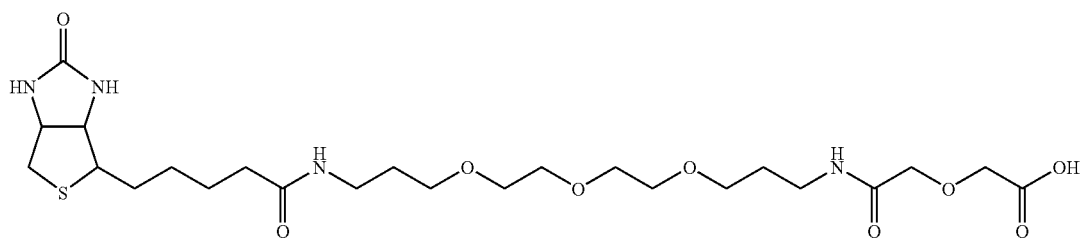

11

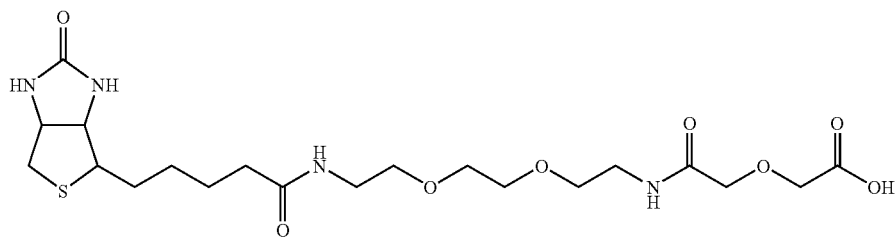

A second type of water-soluble linker moiety comprises an ionized or ionizable moiety. The ionized functionality is preferably at least three (3) atoms away from the point of conjugation with the biotin moiety. Functional groups containing, for example, a sulfonate or an ammonium ion are advantageous. Linker moieties comprising anionic borane and carborane cage molecules are especially preferred, since these moieties provide biotin-containing compounds having enhanced water solubility and a site for radiolabeling.

Representative biotin/water-soluble linker adducts comprising ionic or ionizable functionalities are illustrated in structures 12 and 13 below:

12

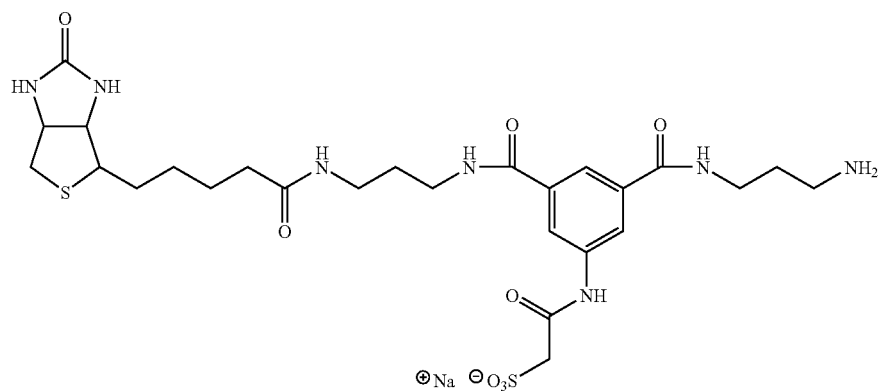

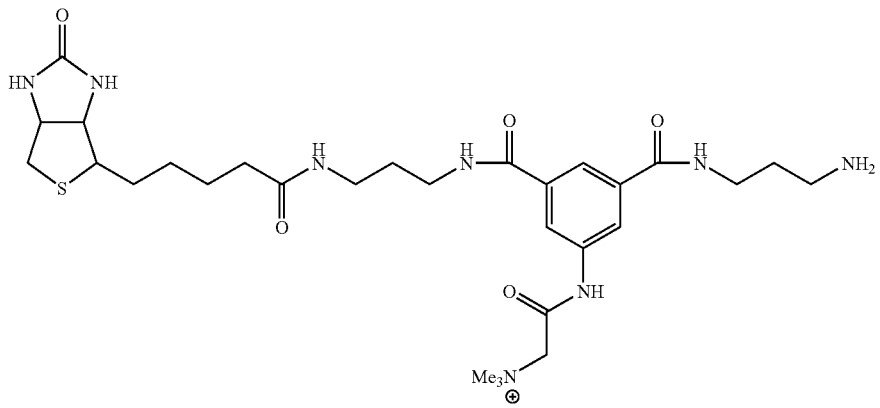

13

Other combinations of ionic or ionizable functionalities and water-soluble linker moieties may be used in combination with differing lengths of chains containing the ionic moiety branched from the water-soluble linker moiety.

Useful ionic water-soluble linker moieties include those that contain anionic boron cage moieties, such as a dodecaborane (icosahedral) cage moiety, which has a minus 2 (−2) charge and a nido-dicarbon carborane cage moiety, which has a minus 1 (−1) charge. Other anionic boranes or carboranes (closo or nido) may be used as water-soluble linkers as well. The borane cage water solubilized linkers are useful when it is desirable to radiohalogenate the biotin-containing compound.

The compounds illustrated in structures 14–16 are exemplary of biotin/water-soluble linker adducts that comprise polyhydroxyl moieties. These adducts may comprise from about 2 to 20 hydroxyl moieties. The hydroxyl groups may be bonded to the linking chain itself (as shown below in structures 14 and 15) or are bonded to a branch point of the linker (as exemplified in structure 16).

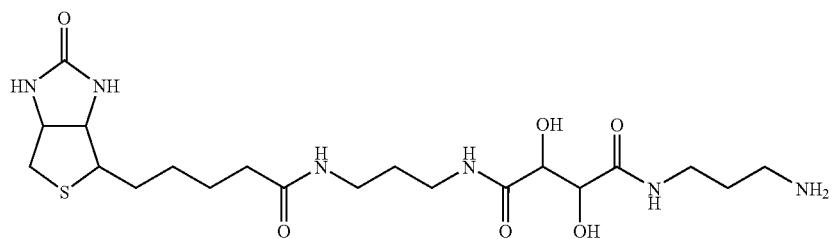

14

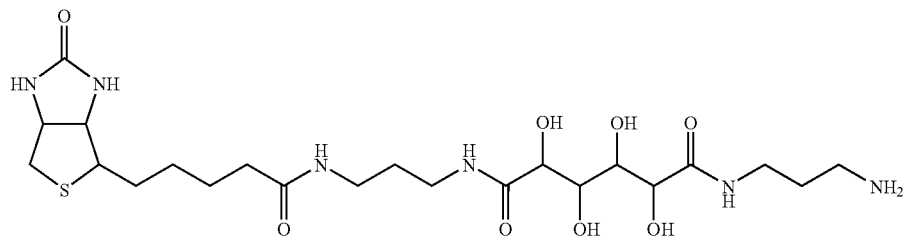

15

-continued

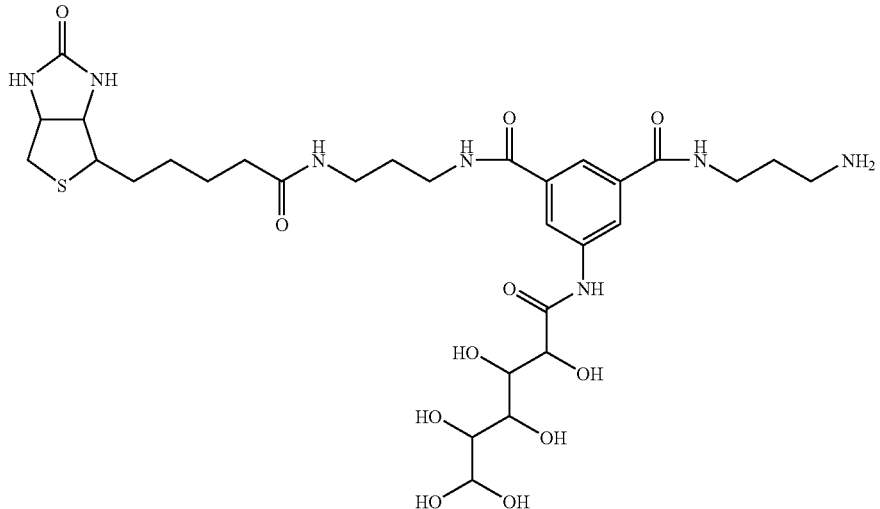

16

Modification of the biotin/water-soluble linker adduct sometimes is desirable to prevent the serum enzyme biotinidase from cleaving the water-soluble linker from the biotin. This is one preferred embodiment of the invention. Introduction of a steric group alpha to the amine (or another functionality) of the water-soluble linker, which is attached to the biotin carboxylate group, provides resistance to cleavage by biotinidase. Suitable steric moieties include, for example, carboxylates, larger alkyl groups, aryl groups, heteroaryl groups, and similar groups that function in the same manner. Depending upon the steric bulk of the branching group alpha to the amine (or other) functionality attached to the carboxylate, some reduction in binding affinity for biotin-binding proteins may result. The particular application of the biotin-containing compound determines how much steric bulk is desired or can be tolerated in the branched group. Water-soluble linkers possessing a branched chain alpha methyl (or other steric) group to the biotin moiety have been found useful in reducing in vivo degradation by biotinidase. Preferred α-methyl group containing linkers include, for example, 3-aminobutyric acid, 1,2-diaminopropane, and 1,4-diaminohexane (Dytek A). As will be described below, amino acids and N-methyl groups have been found useful in retarding biotinidase activity against the compounds of the invention.

After preparation of the biotin/water-soluble linking adduct, the adduct is activated to form the biotinylation reagent according to the invention of structural formula B-P-L-X. B-P-L-X then is reacted with a cross-linker, C, that possesses at least tri-functionality. Exemplary activated biotin/water-soluble linker adducts that can be reacted with a cross-linker, C, include, for example, an activated ester (e.g., tetrafluorophenyl), 17; maleimide, 18; iodoacetamide, 19; hydroxylamine, 20; acyl hydrazine, 21; and nitrophenylazide, 22. Additional reactive functionalities are described by Wilbur in *Bioconjugate Chem.*, 3, 433–470 (1992); and Bodanszky, *Principles of Peptide Synthesis*, Chapter II, pp. 28–35, Springer-Verlag, New York, N.Y. (1984).

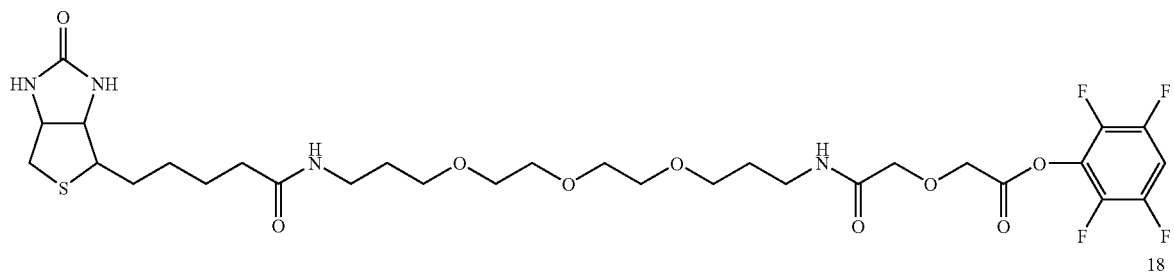

17

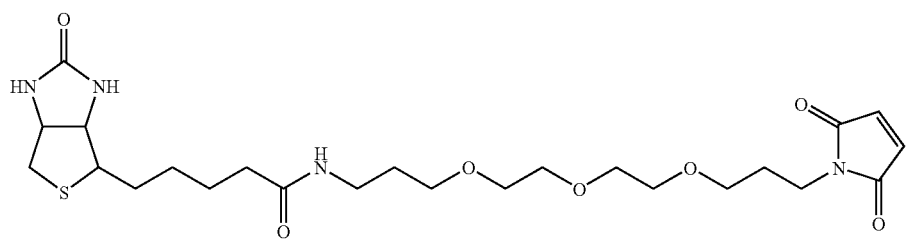

18

-continued

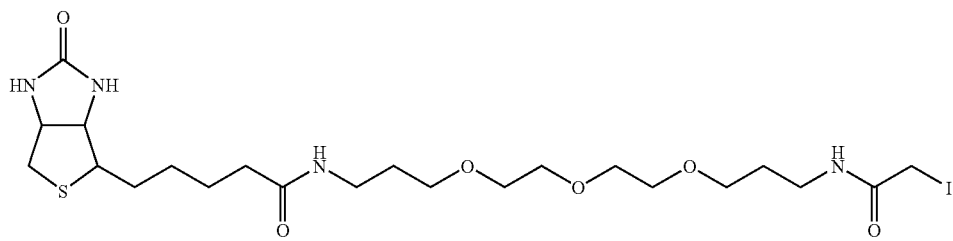

19

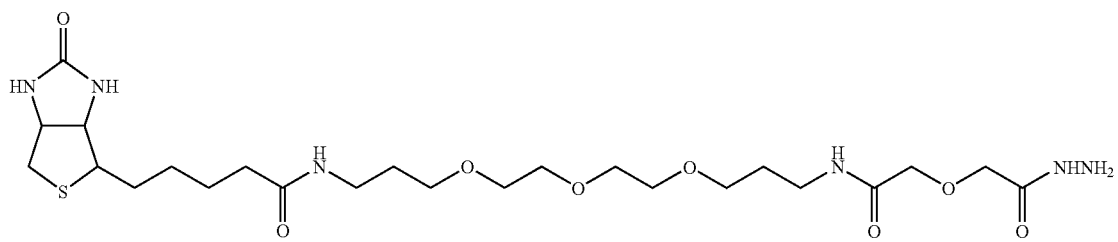

20

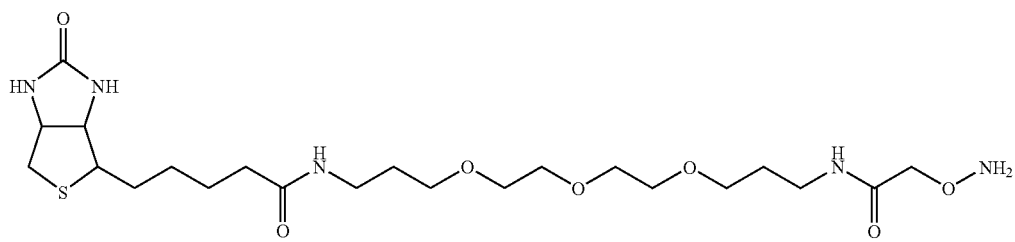

21

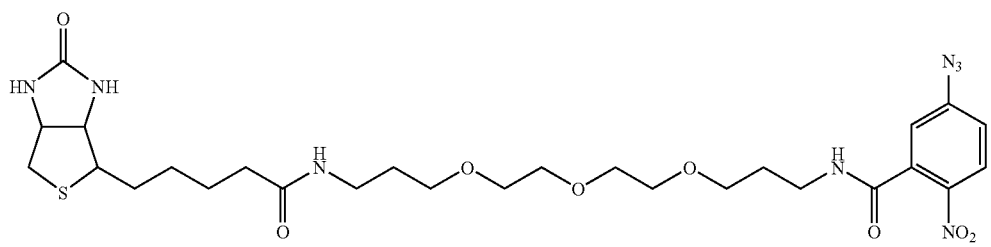

22

As disclosed above, the biotin-containing compounds of the present invention may be linked to targeting moieties, such as, for example, monoclonal antibodies, or fragments or constituents thereof. For example, a combination of an intact monoclonal antibody or a fragment (e.g., F(ab')$_2$, Fab', Fab, scFv, scFv$_2$) with biologically produced, genetically engineered, and/or chemically modified avidin, deglycosylated avidin, or streptavidin, can form a target for the biotin-containing compounds of the invention and used in in vitro assays, or for diagnostic and therapeutic in vivo applications. An important factor in these applications is that the biotin-containing compounds of the present invention are highly water-soluble, and this is important since binding proteins are most stable in aqueous media. More specifically, the multi-water-soluble biotin-containing compounds according to the present invention can be linked to diagnostic or therapeutic functional moieties and used in in vitro assays or for in vivo applications for imaging and/or therapy of human disorders (e.g., cancer, blood clotting, myocardial infarcts, and the like).

Another application for the water-soluble biotin-containing compounds of the present invention is to provide a targeting system that can be used with therapeutic drugs. Targeting of any number of therapeutic drugs to sites, such as tumors, can be accomplished with this system whereby biotinylated therapeutic drugs can be released at a selected site. It is important, in many instances, to release the drug from the biotin-containing compound in its most active form in the cell. This may be accomplished by introducing one or more cleavable functional groups at the point of attachment of the drug to the biotin-containing compound.

When containing a drug or other active moiety, the biotin-containing compound of the present invention has the structural formula:

$$T_m\text{-C-(L-P-B)}_n \quad (F')$$

wherein C, L, P, B, and n are defined as above, T is the drug or other active moiety, and m ranges between about 1 through 5. The drug may be linked to the cross-linker, C, through a bond that is cleaved at a pre-selected site, such as a tumor.

Another application of the water solubilized, biotin-containing compounds of the present invention is to provide a targeting system that can be used with, for example, boron-10-containing compounds. Targeting of any number of boron-10-containing compounds, such as small molecules or polymers, to pre-selected sites such as tumors, can be accomplished with this system. A preferred example of a biotin/boron-10-containing polymer is one prepared from starburst or cascade dendrimers (see Tomalia, in *Topics in Current Chemistry*, 165, 193–313, 1993, for a discussion of dendrimers) where a discrete number (i.e., 3–32) of biotin moieties are attached to a dendrimer and that entity is conjugated with another entity (e.g., dendrimer) that contains 10–200 boron-10 cage molecules (e.g., closo or nido-borane, carbaborane, or dicarbaborane [see Hawthorne, *Angew Chem. Int Ed.*, Engl. 32, 950–984, (1993); Morin, *Tetrahedron* 50, 12521–12569, (1994)] are conjugated. The resulting multi-biotin-containing compound would be used with pre-localized monoclonal antibody/biotin binding proteins to localize boron-10 to selected sites, such as tumors, for subsequent neutron irradiation in a therapeutic protocol.

Trimeric and other multimeric biotin-containing compounds of the present invention can be prepared for the cross-linking of biotin-binding proteins (e.g., streptavidin and avidin). One application for polymerization of biotin-binding proteins is clearance of the antibody-biotin binding protein, or non-bound biotin-biding protein from the blood of patients which have had tumor sites targeted with monoclonal antibodies conjugated with biotin-binding proteins.

In all multi-biotin compounds the minimum distance between any two biotin moieties (carboxylate carbonyls) must be 18 Å (preferably >19 Å). For biotin trimers and tetramers it is a requirement that the distance between any two biotin moieties not exceed 60 Å. For multi-biotin compounds that have 5–32 biotin in them, it is preferable that the distance between any two biotin moieties not exceed 60 Å (but not a requirement). For multibiotin compounds with 32 or more biotin moieties, it is preferable that the majority (at least 50%) of the biotin moieties have less than 60 Å between any two biotins. (This latter case is made for biotin multimers that are supported on a large array (polymer?), where a single multiple biotin moiety in one location has biotin moieties with less than 60 Å between them, but the distance between biotins on any two separate multiple biotin moieties exceeds 60 Å.) By keeping the distance between biotin moieties of less than 60 Å, the biotins of the biotin multimer cannot reach around to the other face of the avidin or steptavidin and fill all four sites with one molecule.

The greatest through-bond distance between any two biotins in the trimer (e.g., structure 15) is 43.5 Å and the greatest through-bond distance between two biotins in the nonamer (e.g., structure 21) is 55.8 Å. The distances do not increase very much if one couples two trimers or two nonamers with a phenyl ring to obtain molecules with 6 or 19 biotin moieties. The following Note on Structures/Distances: The structures below show the linking atoms between any two biotin carboxylcarbonyl atoms in a linearized form. Two trimers can be attached to a dicarboxylbenzene moiety to obtain a molecule with 6 biotins and two nonamers can be attached to a dicarboxyl-benzene moiety to obtain a molecule with 18 biotins. The distance between biotin carbonyls was obtained from 3D structures that were energy and structural minimized, however, this was not done in a rigorous manner so the values should not be considered exact.

Illustrative trimeric biotin-containing compounds, in accordance with the invention, are illustrated in structures 23–26. In these compounds, the biotin moieties are a distance from one another that permits two (2) of the biotin moieties to bind with one tetrameric biotin binding molecule (e.g., avidin), while the third biotin moiety will be free to bind with a separate avidin because it does not have a linker of sufficient length to bind at a third site on the same avidin molecule. The distance between each biotin moiety in the trimeric biotin-containing compound is preferably from about 20 to about 55 Å.

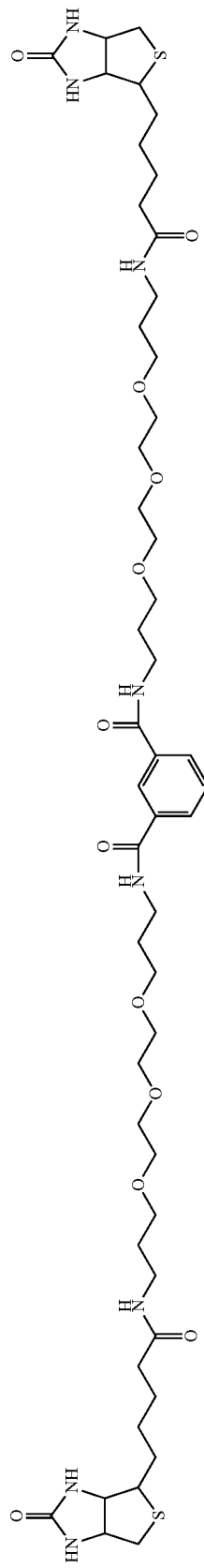
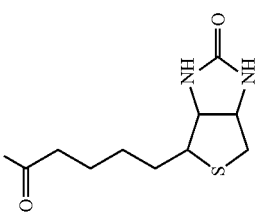

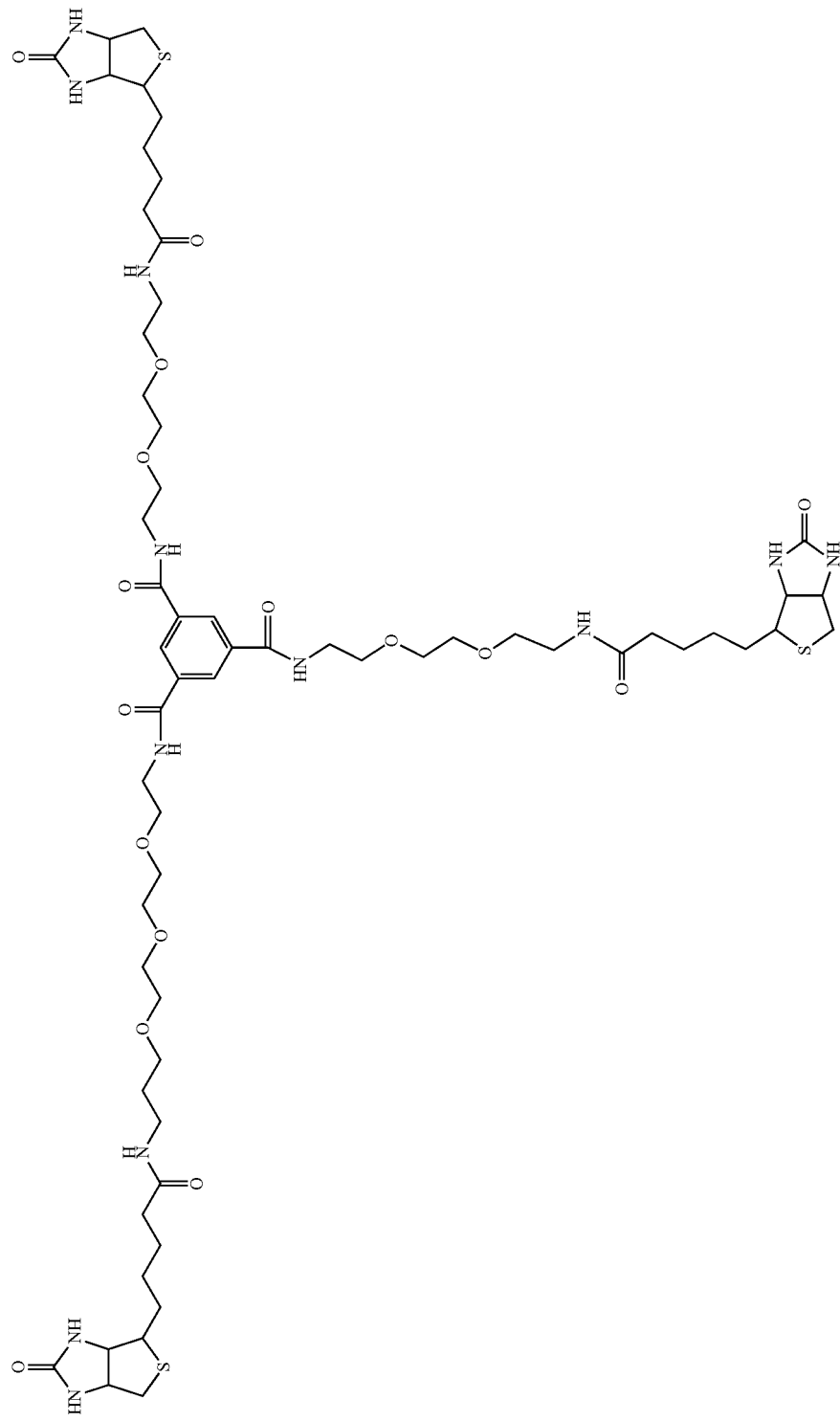

-continued
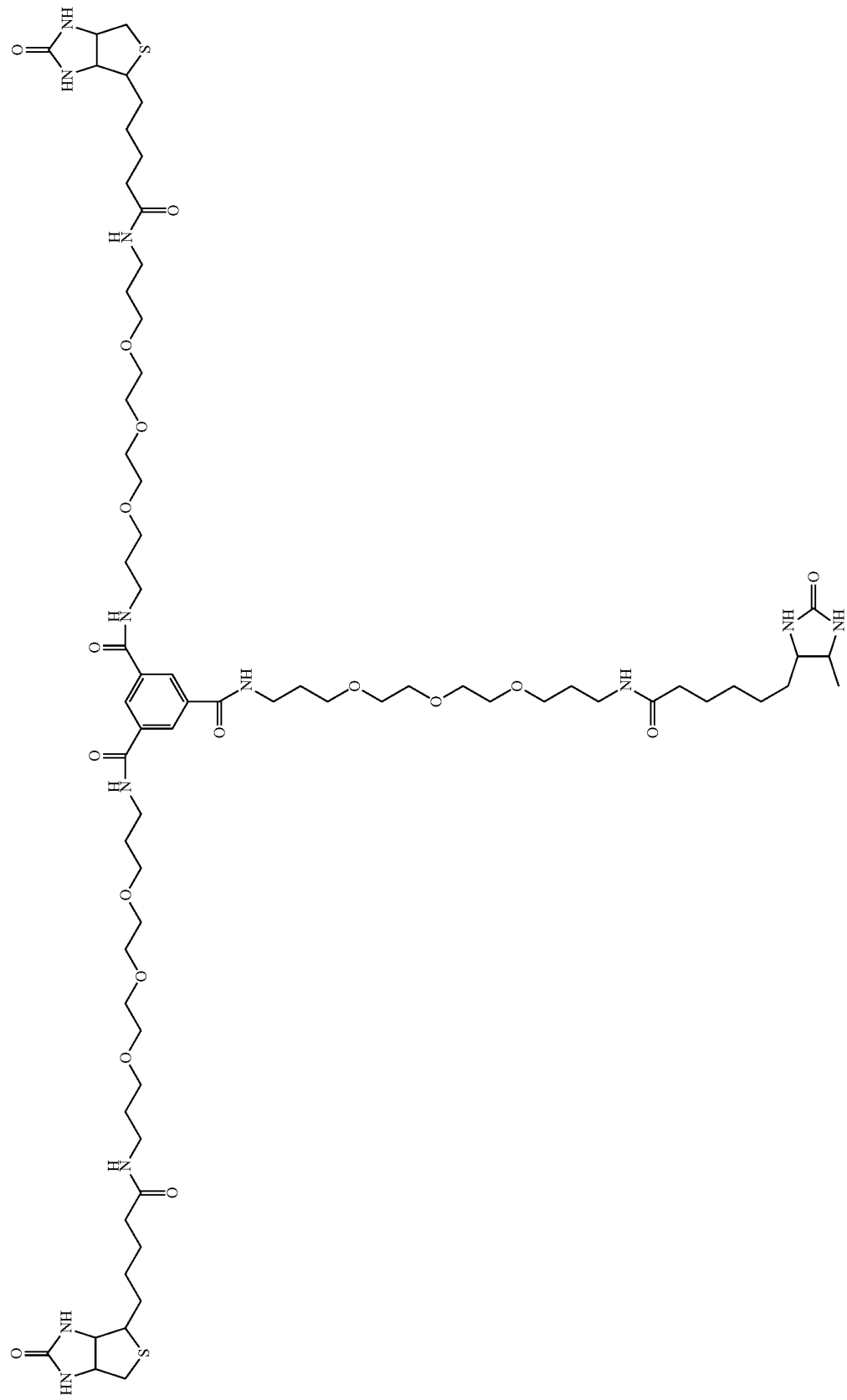

In structure 25, one biotin moiety is the weaker binding desthiobiotin, and this can result in preparing polymers, which are unstable. However, unstable polymers also can be cleared from the blood, which is desirable under some circumstances. Biotin trimer 26 has two desthiobiotin moieties. In this example, four of the trimeric biotin molecules can combine with one (tetrameric) avidin or streptavidin molecule. This permits more (total of 8) desthiobiotin moieties to be carried by the molecule, and can lead to branching in the polymers formed. Biotin multimers having three (3) or more biotin moieties, therefore, are useful for amplification of signals in diagnostic and therapeutic systems.

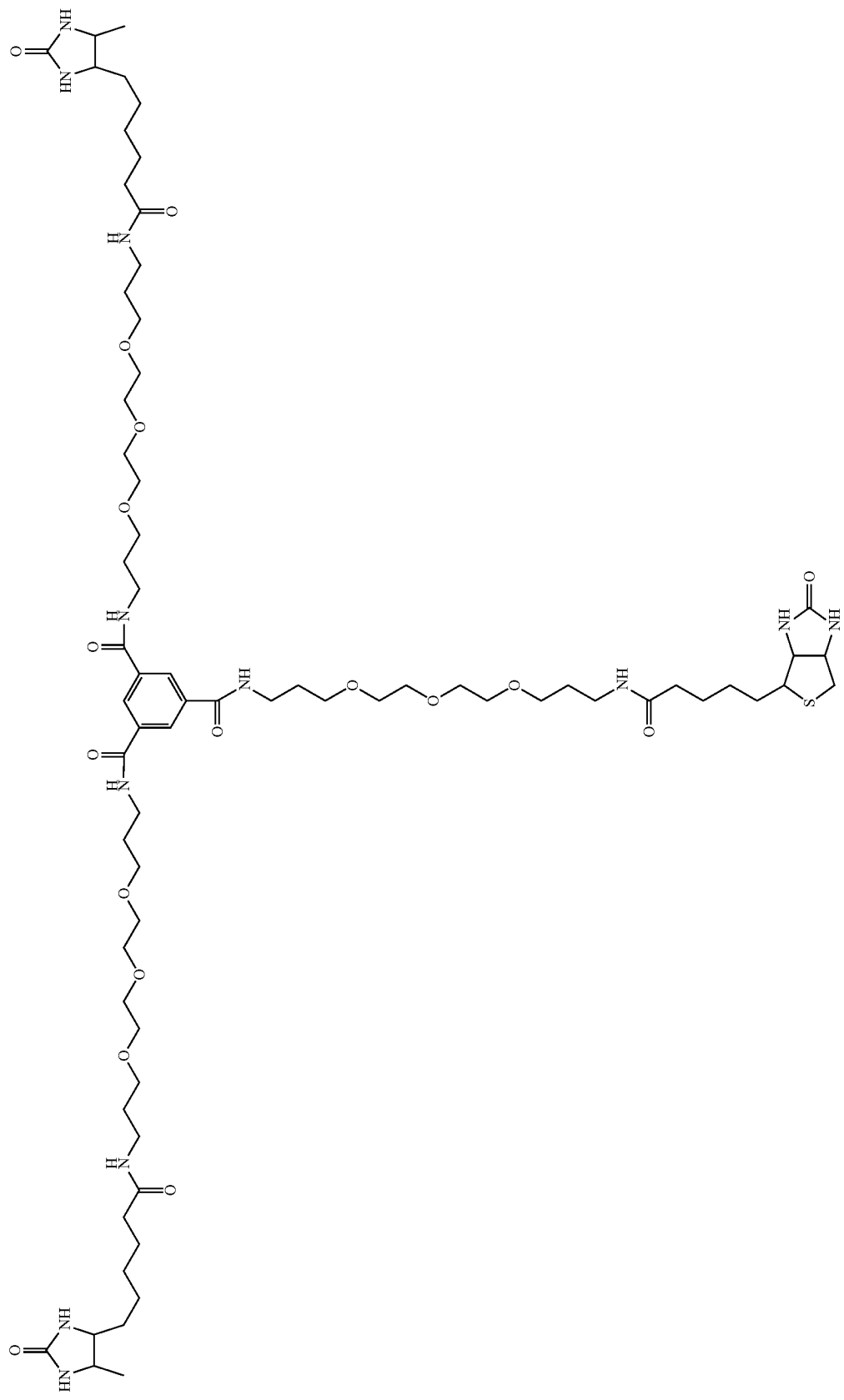

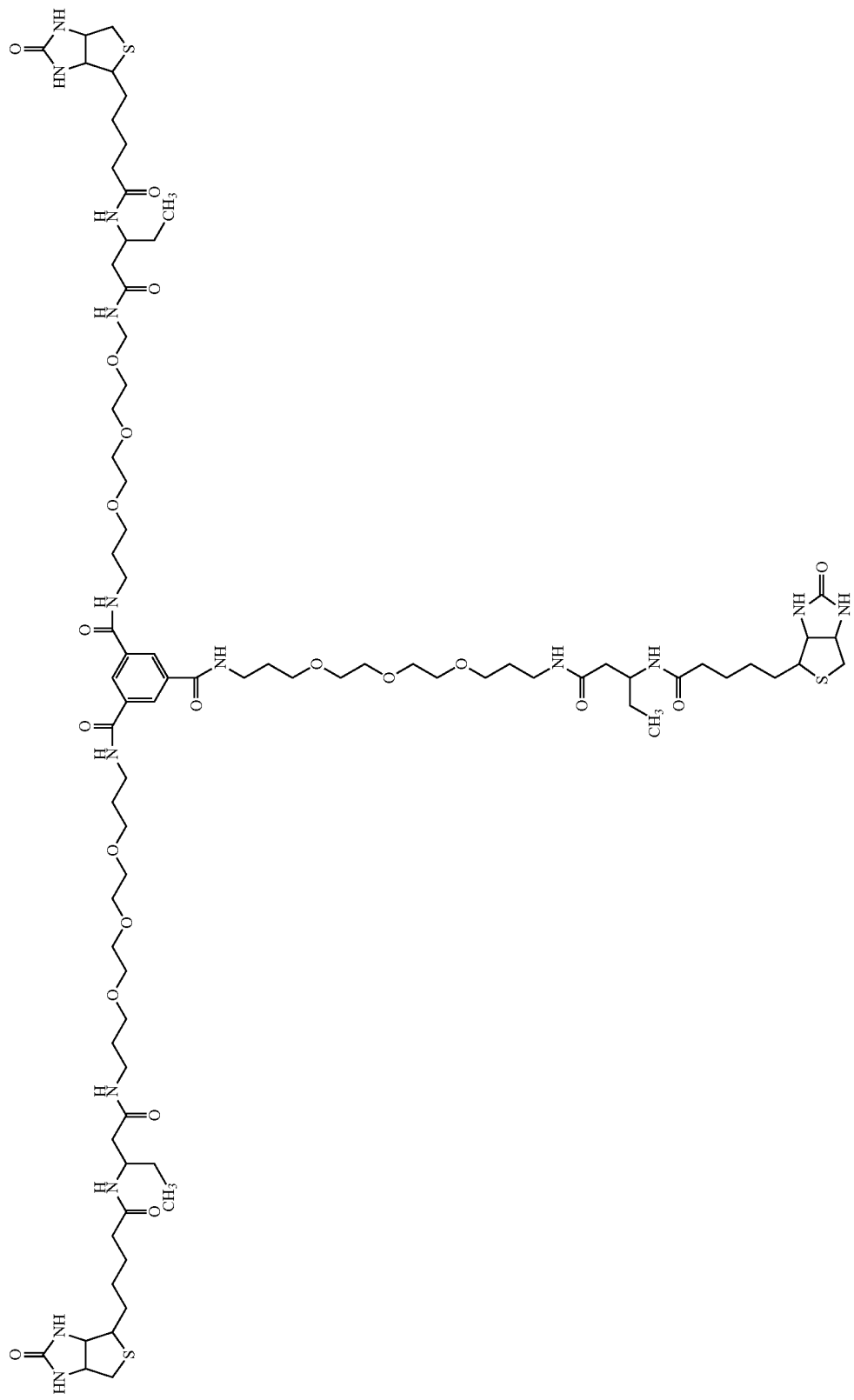

A preferred group of compounds in accordance with the invention use starburst and cascade dendrimers as the cross-linking moiety, C. For example, the reaction of the terminal amine of the starburst dendrimer (e.g., generation 2, available from commercial sources) with a biotinylation reagent, such as structure 27 (see Example 4), produces a compound, which has up to 16 biotin molecules attached. Further dendrimers useful in the present invention are set forth below.

The multimeric biotin-containing compounds, wherein a starburst or cascade dendrimer is used as the crosslinking agent, also may comprise other functional moieties. An important application of these compounds is to increase the amount of radioactivity, photoactive moiety, or drug at a pre-selected site, such as a tumor, by introducing new biotin sites to which biotin-binding proteins can bind. Thus, methods for amplifying the number of sites for binding biotin-binding proteins at a pre-selected target, such as a tumor, would involve multiple alternating administrations of a multi-biotin-containing compound wherein the cross-linker is a starburst dendrimer and a protein, such as avidin or streptavidin. A functional reporter moiety, such as a targeting agent, diagnostic agent, therapeutic agent, or the like, may be linked to the biotin-containing compound or binding protein compound. When this is accomplished in a set of steps, an amplification of the amount of sites available at the tumor is obtained, since, upon each avidin or streptavidin binding to the site, additional biotin binding sites are provided. This amplification can also be accomplished in vitro to improve the detection of desired samples.

INDUSTRIAL APPLICABILITY

The multi-biotin-containing compounds according to the invention can be produced as discrete compounds that have many applications. Specific embodiments of the invention comprise multi-biotin-containing compounds attached to a carrier molecule or a targeting (receptor binding) molecule. For example, a biotinylated starburst dendrimer can be attached to a cancer cell targeting protein, such as a monoclonal antibody, either for in vitro assays, or for in vivo diagnostic or therapeutic applications. Attachment of a multi-biotin moiety to a receptor, in effect, can amplify the number of receptors as multiple streptavidin or avidin moieties can be attached to the multi-biotin-containing compound. The concept of amplification of binding sites is one aspect of the present invention.

The medical and scientific communities are constantly searching for improved diagnostic and therapeutic reagents. The present invention provides advancement in the chemistry of biotin/avidin technology. For example, if a multi-biotin-containing compound according to the invention is used in cancer cell detection through the use of an antibody, amplification is simplified as fewer steps are required. The therapeutic or diagnostic moiety (chromophore, radionuclide, enzyme, etc.) can be attached to the streptavidin or avidin, or it may be introduced via the multi-biotin-containing compound.

While the invention has been described with reference to a preferred embodiment, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In this application all units are in the metric system and all amounts and percentages are by weight, unless otherwise expressly indicated. Also, all citations referred herein are expressly incorporated herein by reference. The following Examples demonstrate methods for synthesizing and using the compounds according to the invention. The Examples are provided by way of illustration, and not by way of limitation.

EXAMPLE 1

Method for Synthesizing an Activated Ester of a Biotin Moiety

The following Example sets forth a methodology for preparing a tetrafluorophenyl (TFP) ester of a biotin moiety that is subsequently reacted with a water-soluble linker moiety and then a cross-linker of at least tri-functionality to produce a biotin-containing compound according to the invention. Other methods for preparing activated esters generally known in the field can be used to prepare biotin activated esters containing any number of phenolic and other hydroxyl (e.g., N-hydroxysuccinimide) groups.

Preparation of Biotin Tetrafluorophenyl Ester

Biotin (10 g, 40.9 mmol) was dissolved in 200 mL warm (70° C.) DMF under an argon atmosphere. The solution was allowed to cool to ambient temperature and 10 mL (82 mmol) triethylamine was added, followed by the addition of 16 g (61 mmol) of 2,3,5,6-tetrafluorophenyl trifluoroacetate. The reaction was stirred at room temperature for 30 min and solvent was removed under vacuum. The product was triturated in 100 mL ether and then filtered. The reaction scheme is shown below. The isolated product was dried under vacuum to yield 14 g (83%) of biotin TFP ester as a colorless solid, mp=185–187° C. $^1$H NMR (DMSO-$d_6$, δ): 1.4–1.8 (m, 6H), 2.5 (m, 1H), 2.6–2.9 (m, 3H), 3.1 (m, 1H), 4.2 (m, 1H), 6.4 (d, 2H), 7.9 (m, 1H); 1R (KBr, cm$^{-1}$) 3250, 2915, 1790, 1710, 1520, 1520, 1480, 1090.

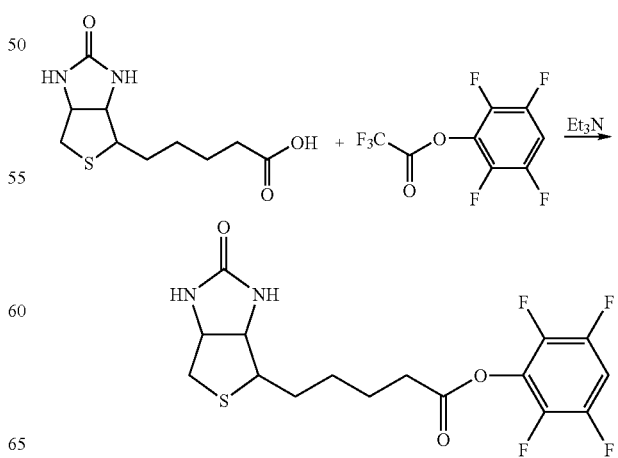

EXAMPLE 2

Method for Preparation of a Water-soluble Biotinylation Reagent

This Example sets forth a general methodology for preparing a biotin moiety linked to a water-soluble linker moiety. In the example, a diamino-ether linker is used. Ether linkers containing terminal functionalities such as, an amine and a carboxylate; an amine and an alcohol; an alcohol and a carboxylate; and two alcohols, can also be prepared using the method described. The general method can also be used when the linker contains polyhydroxyl groups if the terminal functionalities are two amines, or are an amine and a carboxylate.

Preparation of a Biotin Compound Containing a Trioxo-Amide Linker with an Amine Terminus The TFP ester of biotin (5 g, 12.8 mmol) (Example 1) was dissolved in 200 mL anhydrous DMF. In another flask containing 28 g (128 mmol) 4,7,10-trioxa-1,13-tridecanediamine was added 4 mL of triethylamine. Both the flasks were cooled to 0–5° C. by ice water. The TFP ester of biotin was added, dropwise, to the trioxatridecanediamine solution over the period of 1 hour. The mixture was stirred at room temperature for 30 minutes and the solvent was removed under vacuum. The resulting oil was triturated in 500 mL ether and was stirred for 30 minutes. The solid was filtered. The solid product was dissolved in methanol:ethyl acetate (8:2) and loaded on silica column. The column was eluted with methanol:ethyl acetate (8:2). Fractions containing product were collected and the solvent was removed under vacuum. The isolated product was dried under vacuum to yield 4.5 g (79%) of desired product as a colorless solid, mp=104–106° C. $^1$H NMR (MeOH, δ): 1.46 (m, 2H), 1.6–1.8 (m, 9H), 2.2 (t, 2H), 2.7 (d, 1H), 2.75–2.9 (m, 3H), 3.2–3.3 (m, 5H), 3.5–3.6 (m, 14H); 4.3 (m, 1H), 4.5 (m, 1H), 1R (KBr, cm$^{-1}$) 3280, 2910, 2850, 1690, 1640, 1110, 940.

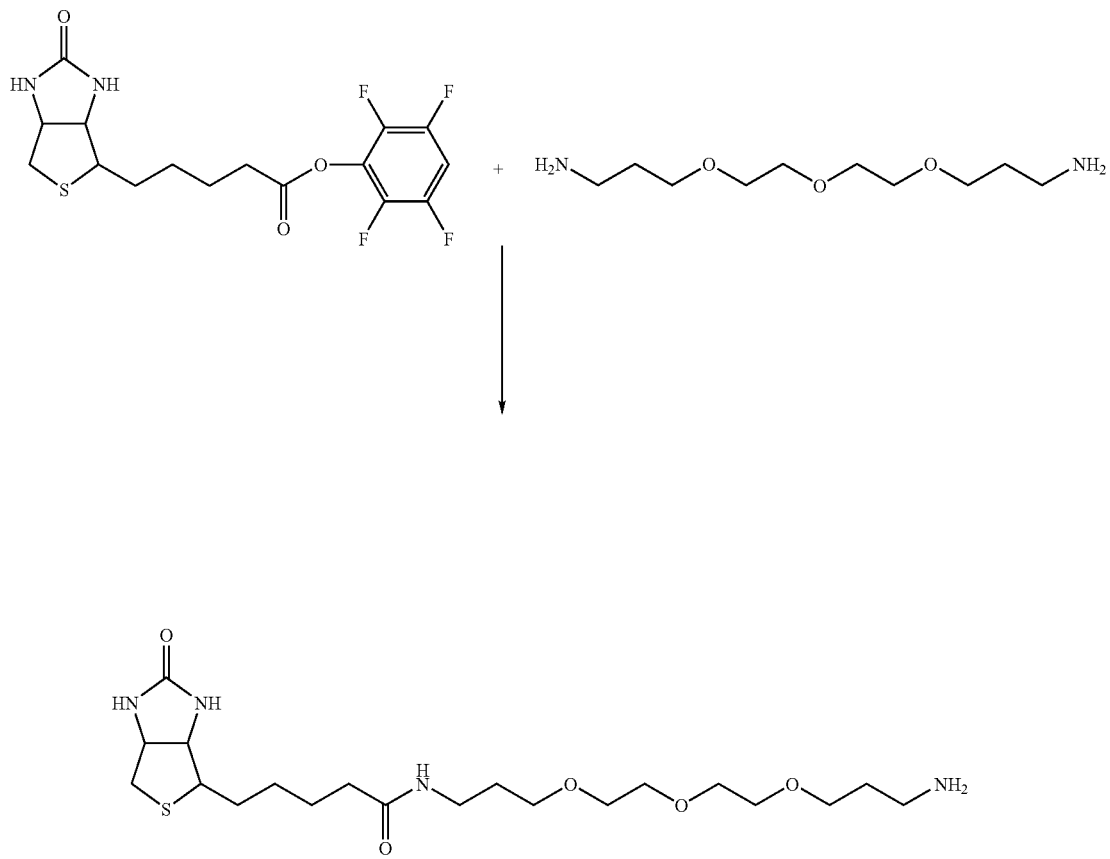

EXAMPLE 3

Reacting an Activated Ester of Biotin with a Diamino-linker that has One Amine Protected This Example sets forth a general methodology for preparing a biotin/water-soluble linker adduct wherein one amine group was protected, i.e., a diamino-ether linker was protected as a t-Boc derivative prior to addition to the biotin activated ester. Any number of amine protecting groups can be utilized in this reaction. The primary purpose of the reaction method, as opposed to Example 2, is to be able to react one equivalent of diamino linker molecule with one equivalent of the biotin active ester. The reaction scheme is set forth below.

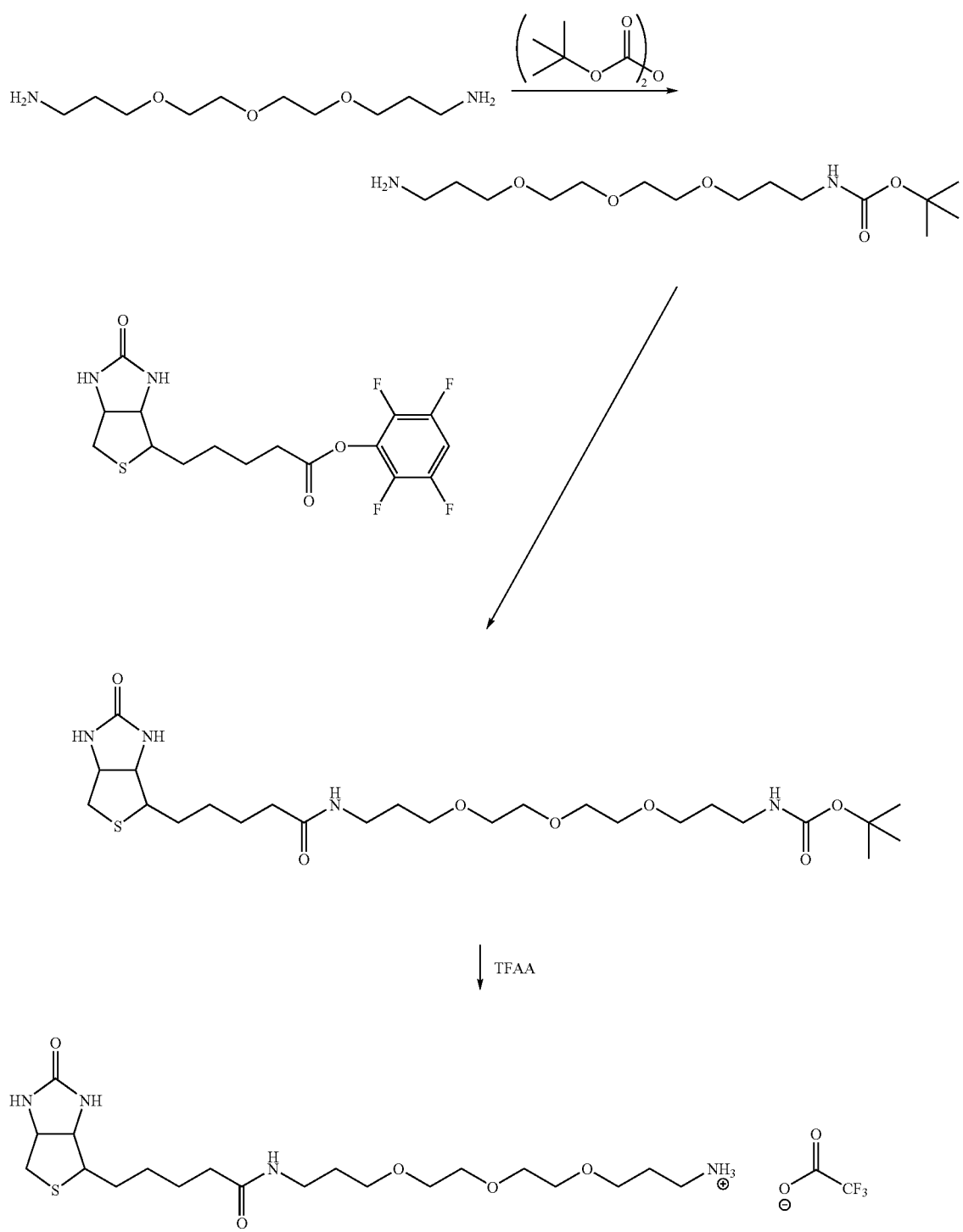

Reaction Step 1: Preparation of N-Boc-4,7,10-trioxatridecane-13-amine

To a solution of 151.40 g (687.25 mmol) of 4,7,10-trioxa-1,13-tridecaneamine in 700 mL CHCl$_3$ was added 6.00 g (27.5 mmol) of di-tert-butyl dicarbonate in 100 mL CHCl$_3$ with stirring at ambient temperature over 30 minutes. The mixture was stirred for 12 hours, washed with water (8×100 mL), dried over anhydrous Na$_2$SO$_4$, and concentrated under reduced pressure to yield 8.23 g (25.7 mmol) of the desired product as a clear oil: $^1$H NMR(CDCl$_3$, δ): 5.18 (s, 1H, CONH), 3.55 (m, 12H —OCH$_2$), 3.20 (m, 2H CH$_2$NHCO), 2.68 (t, 2H CH$_2$NH$_2$), 1.73 (m, 4H), 1.41 (s, 9H).

Reaction Step 2: Preparation of N-(13-N-Boc-4,7,10-trioxatridecanyl)biotinamide To a solution containing 1.00 g (2.54 mmol) of 2,3,5,6-tetrafluorophenol ester of biotin in 100 mL CH$_3$CN at 55° C. was added 0.80 g (2.49 mmol) of N-Boc-4,7,10-trioxa-13-tridecaneamine in 25 mL CH$_3$CN. The mixture was allowed to cool to ambient temperature and then stirred for 10 hours. The solvent was evaporated under reduced pressure and the residue was re-dissolved in 200 mL EtOAc. The EtOAc solution was washed with (2×100 mL) 10% solution of NaHCO$_3$, (2×50 mL) water, dried over anhydrous Na$_2$SO$_4$, and concentrated to yield the desired product as a tacky solid. $^1$H NMR (CDCl$_3$, δ): 6.71 (s, NH, 1H), 6.53 (s, NH, 1H), 5.89 (s, NH, 1H), 5.06 (s, NH, 1H), 4.47 (m, 1H), 4.27 (m, 1H), 3.57 (m, 12H), 3.30 (m, 2H), 3.17 (m, 2H), 3.11 (m, 1H), 2.87 (dd, J=12.8, 4.5 Hz, 1H), 2.71 (d, J=12.8 Hz, 1H), 2.15 (t, 2H), 1.72 (m, 10H), 1.40 (s, 9H).

Reaction Step 3: Preparation of 13-N-Biotinamide-4,7,10-trioxatridecaneamine trifluoroacetic acid salt N-Boc-trioxa-biotinamide, 1.25 g (2.28 mmol), was dissolved in 10 mL trifluoroacetic acid and stirred for 30 min at ambient temperature. Excess trifluoroacetic acid was evaporated under reduced pressure to yield 1.24 g (2.17 mmol) of the desired trifluoroacetate salt as an oil: $^1$H NMR (CD$_3$OD, δ): 4.25 (m, 1H), 4.13 (m, 1H), 3.35 (m, 10H), 3.32 (m, 2H), 2.97 (m, 4H), 2.81 (m, 2H), 2.65 (dd, J=12.8, 4.8 Hz), 2.63 (d, J=12.8 Hz), 1.93 (m, 2H); 1.64 (m, 2H), 1.48 (m, 4H), 1.37 (m, 2H), 1.18 (m, 2H).

EXAMPLE 4

Method of Preparing a Carboxy Derivative of a Water-Soluble, Biotinidase-Stabilized Biotinylation Reagent This Example sets forth a general methodology for preparing a biotin/water-soluble linker adduct comprising an ω terminal carboxylate. The method described can be applied in a general way to prepare various biotin/water-soluble linker adducts. In the reaction described, an amine and ester-terminated ether linker are used. It should be recognized, however, that reagents wherein the linker has other combinations of groups (e.g., amines, carboxylates, thiols, and alcohols at the termini) also can be used to advantage in this method.

The reaction scheme for this Example is set forth below.

Where: R = H
R = Tosyl (Step 1)

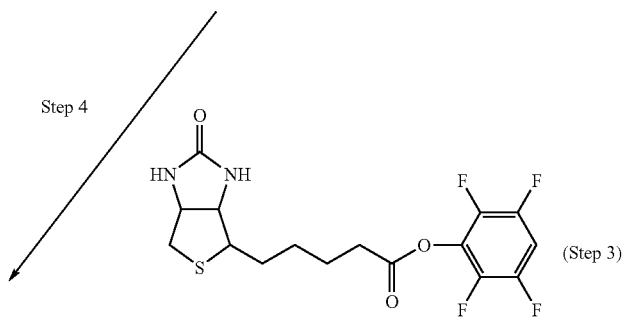

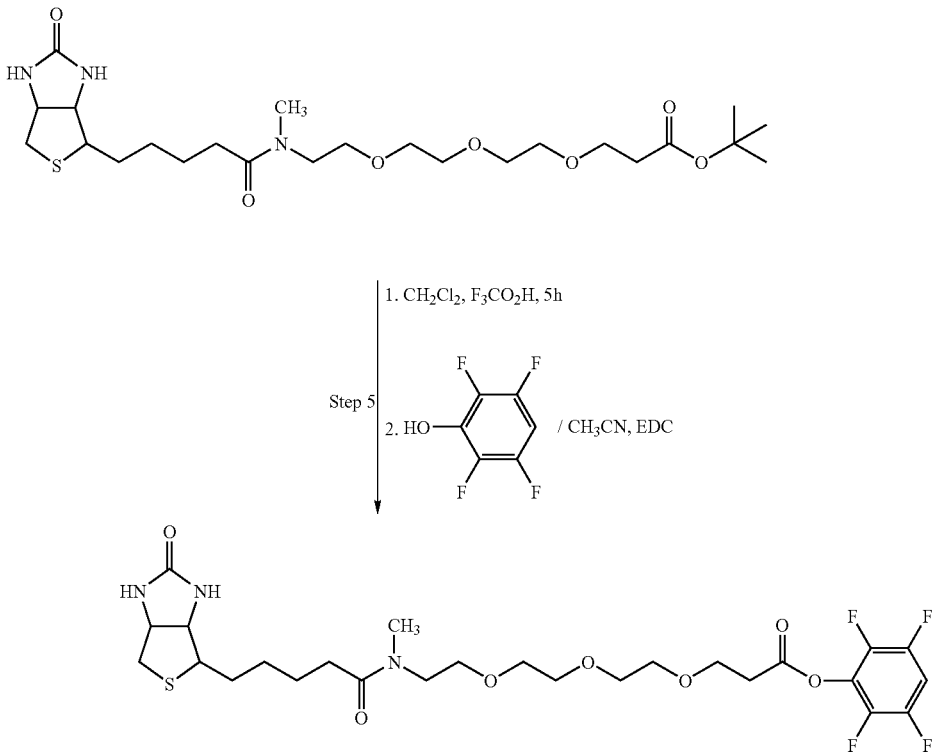

Reaction Step 1:
13-O-p-Tosyl-4,7,10,13-tetraoxadodecanoic Acid tert-Butyl Ester To a solution of 12-hydroxy-4,7,10-trioxadodecanoic acid t-butyl ester (15 g, 54 mmol) in 100 mL pyridine at 0–5° C. was added p-toluenesulfonyl chloride (20.6 g, 108 mmol). The reaction mixture was stirred at 0° C. for 4 hours, poured into an ice/water bath and the aqueous layer was extracted with $CH_2Cl_2$ (3×125 mL). The combined organic layers were washed with 2% HOAc and $H_2O$, and then dried over anhydrous $Na_2SO_4$. The solvent was removed under vacuum to yield a colorless oil. The oil was dried under vacuum to yield 22 g (96%) of the desired product. $^{1H}$ NMR (CDCl3) δ 1.42 (s, 9H), 2.48 (s, 3H), 2.5 (t, 2H), 3.5–3.8 (m, 13H), 4.2 (m, 2H), 7.3 (d, 2H), 7.8 (d, 2H). IR (Nujol, $cm^{-1}$) 3420, 1720, 1630, 1590, 1450, 1360, 1250, 920. HRMS calculated for $C_{20}H_{32}O_8SNa$ (M+Na) is 455.1716; found 455.1707.

Reaction Step 2:
12-N-Methylamino-4,7,10-trioxadodecanoic Acid tert-Butyl Ester A 2 M solution of methylamine in THF (176 mL, 352 mmol) was added to a solution of 13-O-p-tosyl-4,7,10,13-tetradecanoic acid tert-butyl ester (11 g, 25.3 mmol) in THF (10 mL). The reaction mixture was stirred at room temperature for 40 hours. The solvent then was removed under the vacuum. The residue was extracted with chloroform (3×100 mL). The combined chloroform extracts were washed with (2×50 mL) $H_2O$, dried over anhydrous $Na_2SO_4$, and the $CHCl_3$ was removed under vacuum. The product was loaded on a silica column. The column first was eluted with ethyl acetate, and then with varying percentages of ethyl acetate: methanol until 100% MeOH was eluted. The fractions containing product were reduced in volume and the isolated product was dried under vacuum to yield 3 g (40%) of the desired product as an oil. $^1$H NMR (CDCl$_3$) δ 1.4 (s, 9H), 2.38 (s, 3H), 2.42 (t, 2H), 2.7 (m, 2H), 3.5–3.8 (m, 13H). IR Nujol, $cm^{-1}$) 3320, 1720, 1550, 1450, 1360, 1250, 1100, 940. HRMS calculated for $C_{14}H_{30}NO_5$ (M+H)$^+$ is 292.2124; found 292.2116.

Reaction Step 3: Biotin tetrafluorbphenyl ester

This compound was prepared by reaction of biotin with 2,3,5,6-tetrafluorophenyl trifluoroacetate as described in Example 1.

Reaction Step 4: 12-N-Biotinyl-(N-methyl)amino-4,7,10-trioxadodecanoic Acid tert-Butyl Ester $Et_3N$ (60 μL, 0.412 mmol) was added to a solution of 12-N-methylamino-4,7,10-trioxadodecanoic acid tert-butyl ester (0.12 g, 0.412 mmol) in 25 mL of DMF followed by addition of biotin TFP ester (0.161 g, 0.412 mmol). The reaction mixture was stirred at room temperature for four (4) hours and the solvent was removed under vacuum. The residue was extracted with $CHCl_3$ (300 mL). The $CHCl_3$ solution was washed with saturated aqueous $NaHCO_3$ (3×25 mL), then $H_2O$ (2×25 mL), and dried over anhydrous $Na_2SO_4$. The $CHCl_3$ was removed under vacuum to yield 0.21 g (98%) of the product as an oil. $^1$H NMR (CDCl$_3$) δ 1.4 (s, 10H), 1.6–1.8 (m, 4H), 2.3 (t, J=4.25 Hz, 3.9 Hz, 1H), 2.4 (t, J=3.75 Hz, 3.6 Hz, 1H), 2.5 (t, J=3.5 Hz, 3.4 Hz, 2H), 2.8 (d, J=6.75 Hz, 1H), 2.9–3.0 (m, 4H), 3.1 (s, 2H), 3.2 (bs, 1H), 3.45–3.7 (m, 13H), 4.35 (s, 1H), 4.55 (s, 1H), 5.7 (d, J=7.5 Hz, 1H), 6.1 (d, J=10.5 Hz, 1H). IR Nujol, $cm^{-1}$)

3260, 3060, 1780, 1690, 1520, 1480, 1260, 1080, 930. HRMS calculated for $C_{24}H_{44}N_3O_7S$ (M+H)$^+$ is 518.2900; found 518.2923.

Reaction Step 5: 12-N-Biotinyl-(N-methyl)amino-4, 7,10-trioxadodecanoic Acid Tetrafluorophenyl Ester $CF_3CO_2H$ (1 mL) was added to a solution of 12-N-biotinyl-(N-methyl)amino-4,7,10-trioxadodecanoic acid tert-butyl ester (0.21 g, 0., 406 mmol) in 10 mL $CH_2Cl_2$. This mixture was stirred at room temperature for 5 hours. The mixture was reduced in volume under vacuum and the residue acid intermediate was dissolved in 20 mL of $CH_3CN$. Tetrafluorophenol (0.083 g, 0.5 mmol) was added, followed by EDC (0.096 g, 0.5 mmol). The reaction mixture was stirred at room temperature for 16 hours and the solvent was removed under vacuum. The residue was extracted with $CHCl_3$ (300 mL), washed with saturated aqueous $NaHCO_3$ (3×25 mL), then $H_2O$ (2×25 mL), and dried over anhydrous $Na_2SO_4$. The solvent was removed under vacuum to yield 0.243 g (93%) of the product as an oil. $^1$H NMR (CDCl$_3$) δ 1.4 (s, 2H), 1.5–1.7 (m, 4H), 2.3 (m, 2H), 2.65 (d, J=6.25 Hz, 1H), 2.8–2.9 (m, 4H), 3.0 (s, 2H), 3.4–3.6 (m, 13H), 3.8 (s, 2H), 4.35 (s, 1H), 4.45 (s, 1H), 6.0 (d, J=8.25 Hz, 1H), 6.3 (d, J=6.75 Hz, 1H0, 6.95 (m, 1H). IR Nujol, cm$^{-1}$) 3260, 3060, 1780, 1690, 1520, 1480, 1260, 1080, 930. HRMS calculated for $C_{26}H_{35}N_3O_7F_4S$ (M+H)$^+$ is 610.2210; found 610.2216.

EXAMPLE 5

Method for Preparing a Multi-Biotin-Containing-Compound with a 35 Atom Distance Between the Biotin Carboxylates

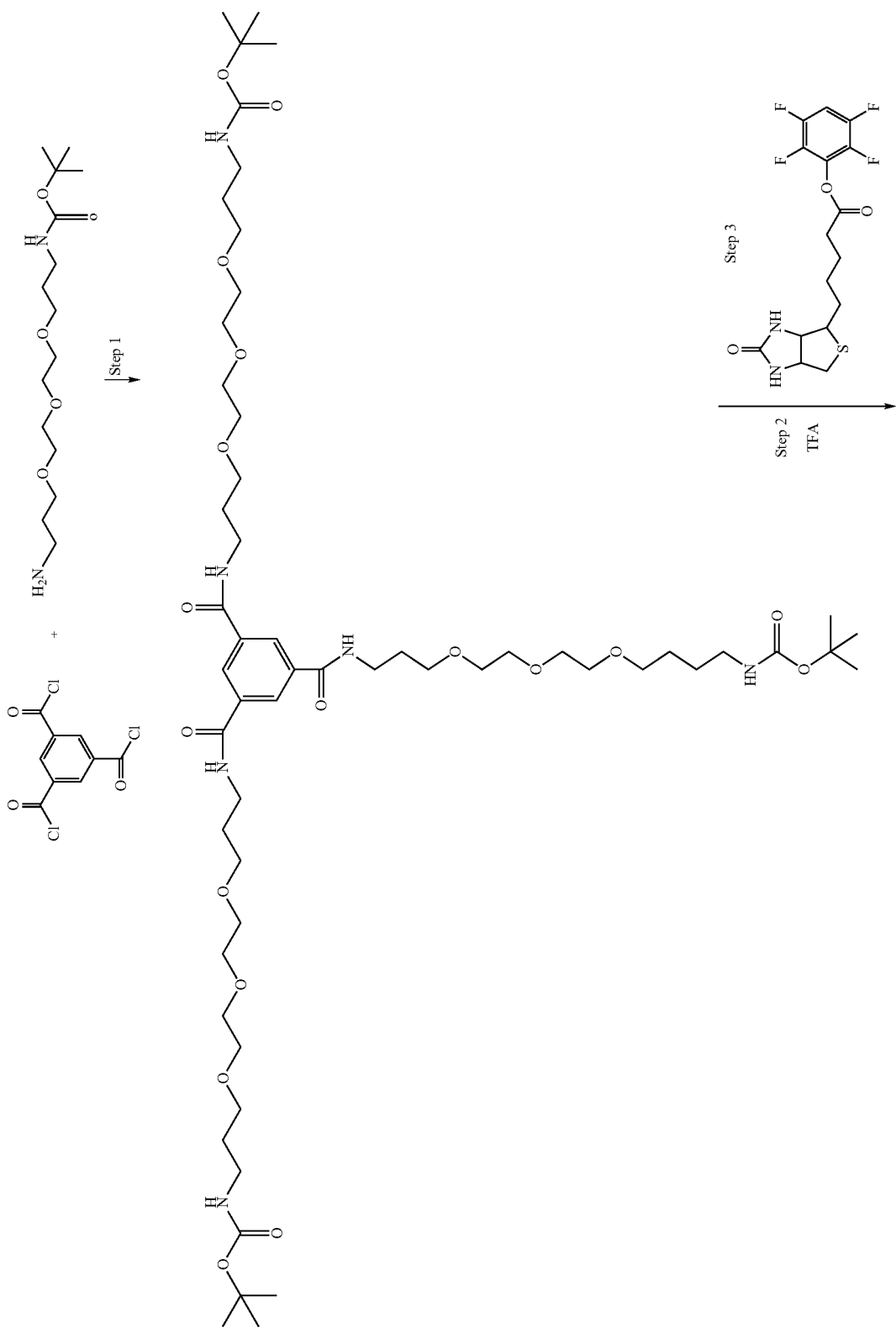

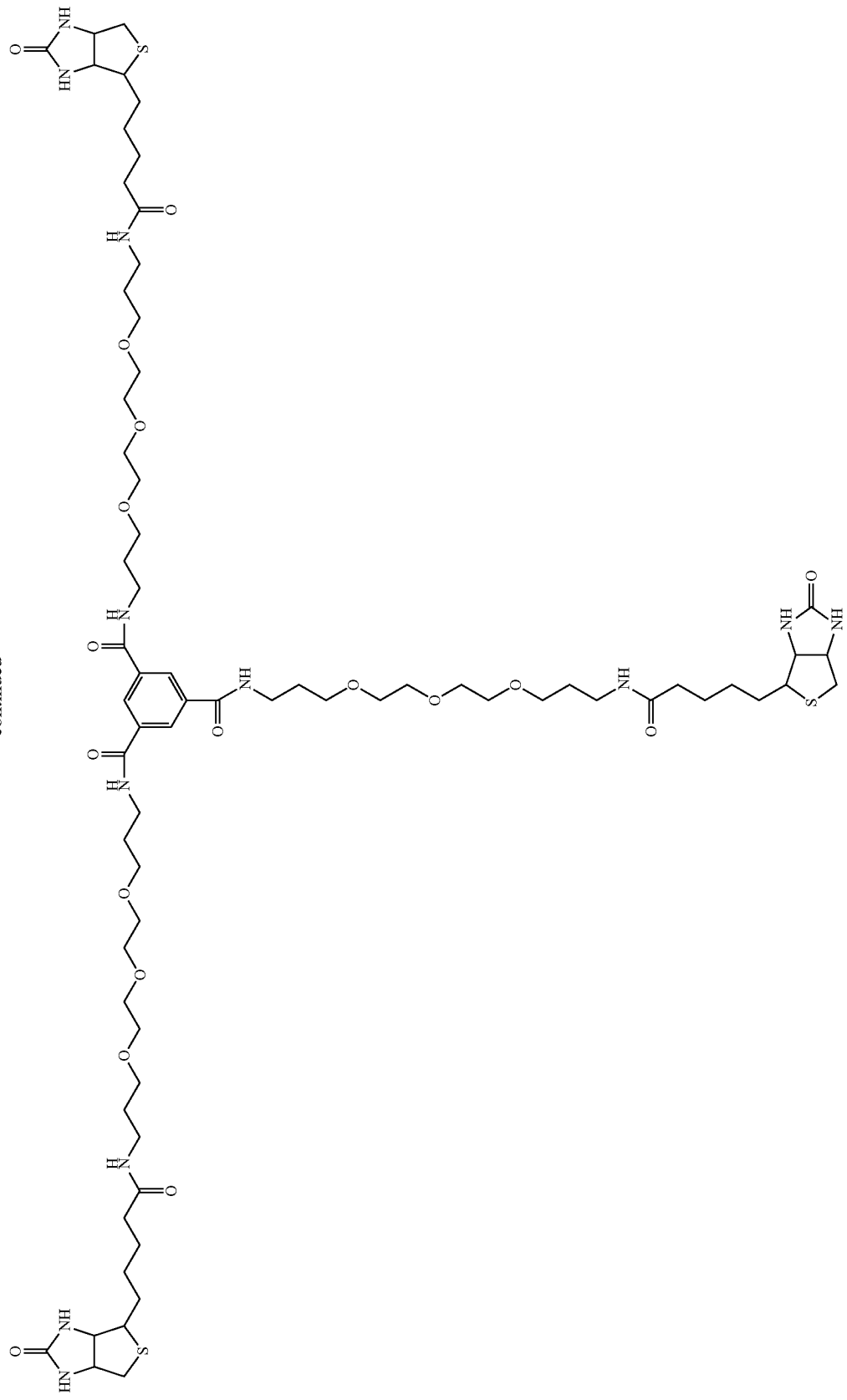

Reaction Step 1. Preparation of N,N',N''-tris-(13-N-BOC-4,7,10-trioxatridecanyl) benzene-1,3,5-tricarboxyamide To a solution of benzene-1,3,5-tricarbonyl trichloride (0.28 g, 1.05 mmol) in 10 mL of $CH_2Cl_2$ at 0° C. was added 0.96 g (2.99 mmol) of 13-N-Boc-4,7,10-trioxatridecaneamine (see Example 3) and 1.45 g (14.34 mmol) triethylamine in 5 mL $CH_2Cl_2$. That mixture was stirred under argon for 10 hours at ambient temperature and the volatile materials were removed under reduced pressure. The residue was redissolved in 150 mL $CH_2Cl_2$, washed with 20 mL of water, dried over anhydrous $Na_2SO_4$ and evaporated to give 0.94 g (83%) the desired biotin trimer as a tacky solid. $^1H$ NMR ($CDCl_3$, δ) 8.38 (s, 3H), 7.64 (s, ArCONH, 3H), 5.16 (s, Boc-NH, 3H), 3.62 (m, 30H), 3.55 (m, 6H), 3.46 (m, 6H), 1.89 (m, 6H), 1.67 (m, 6H), 1.41 (s, 27H).

Reaction Step 2: N,N',N''-tris-(13-amino-4,7,10-trioxatridecanyl)benzene-1,3,5-tricarboxamide trifluoroacetic acid salt The N-Boc protected triamide (0.25 g, 0.23 mmol) was dissolved in 5 nL trifluoroacetic acid at ambient temperature and stirred for 30 minutes. Excess trifluoroacetic acid was evaporated under reduced pressure to yield 0.26 g (0.22 mmol) of the trifluoroacetic acid salt as an oil. $^1H$ NMR ($CD_3OD$) δ 8.47 (s, 3H), 3.64 (m, 36H), 3.60 (m, 6H), 3.14 (m, 6H), 1.94 (m, 12H).

Reaction Step 3: N,N',N''-tris(13-N-Biotinamide-4,7,10-trioxatridecanyl)benzene-1,3,5-tricarboxamide To 0.19 g (0.18 mmol) of the tris trifluoroacetate salt in 3 mL DMF was added 1 mL (7.17 mmol) triethylamine, followed by 0.24 g (0.61 mmol) of biotin tetrafluorophenol ester in 2 mL DMF. The solvents were evaporated under reduced pressure and the residue was washed with 2 mL water, 2 mL of a 10% solution of $NaHCO_3$, 2 mL water, then 2 mL acetone. The residue was crystallized from methanol/acetone to give 0.04 g (11%) as colorless crystals. mp=106–108° C.; $^1H$ NMR($CD_3OD$, δ) 8.44 (s, 3H), 4.49 (m, 3H), 4.31 (m, 3H), 3.60 (m, 36H), 3.23 (m, 12H), 2.91 (m, 3H), 2.71 (d, J=12.7 Hz), 2.15 (m, 12H), 1.91 (m, 6H), 1.65 (m, 12H), 1.40 (m, 6H), MS (FAB+): mass calculated for $C_{69}H_{114}N_{12}O_{18}S_3$ is 1495; found m/z isotope cluster at 1496–1499 (M+H).

EXAMPLE 6

Method for Preparing a Water-soluble Biotin Trimer with a 25 Atom Distance Between the Biotin Carboxylates

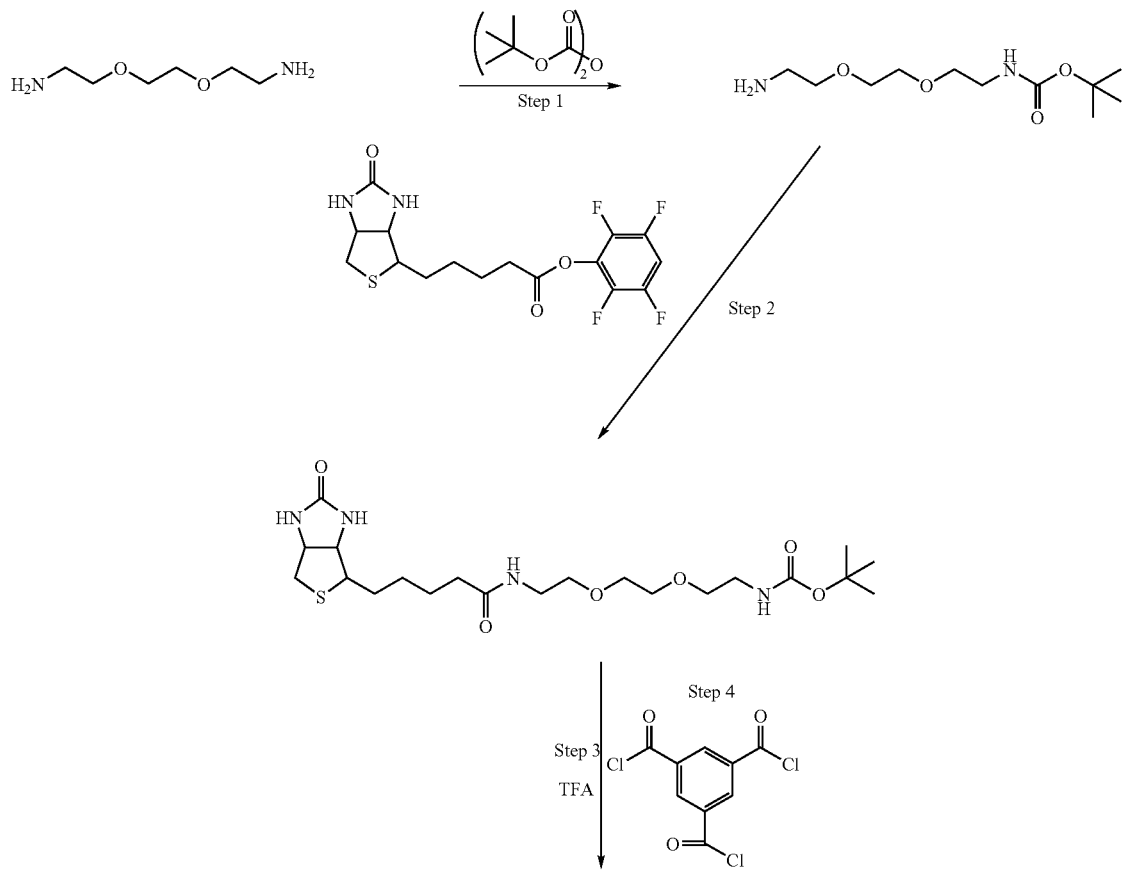

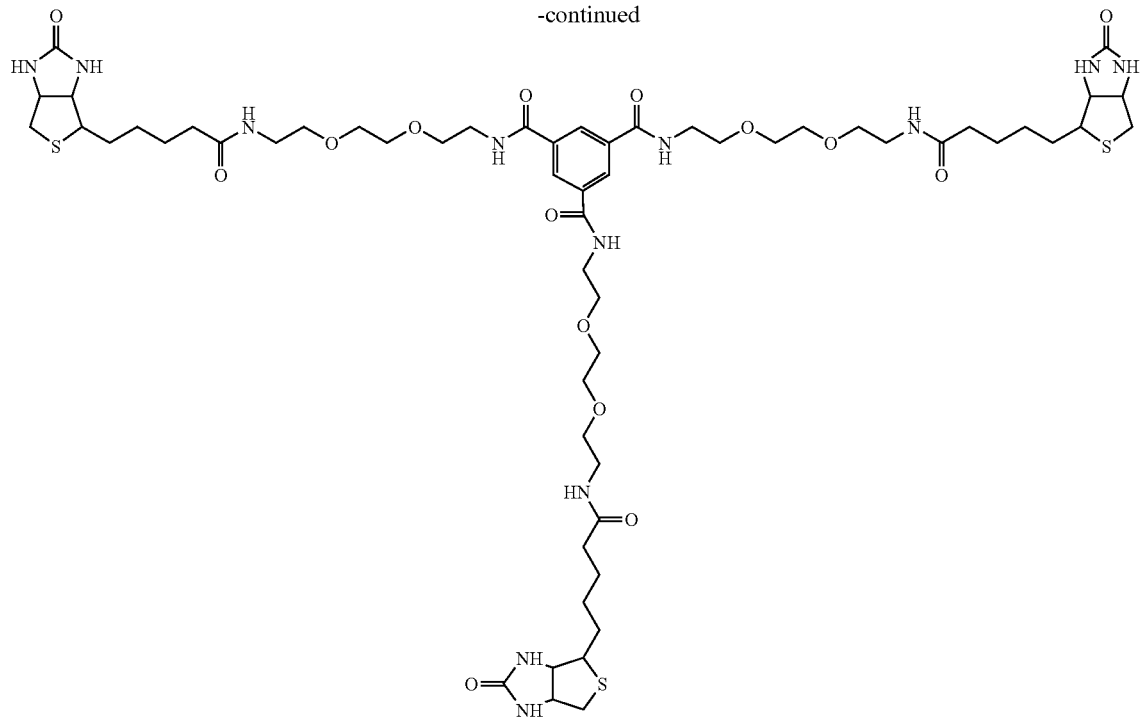

Reaction Step 1: Preparation of 8-N-Boc-3,6-dioxaoctaneamine

To a solution of 163 g (1100 mmol) of 3,6-dioxa-1,8-octanediamine in 700 mL CHCl$_3$ was added 8.00 g (36.65 mmol) of di-tert-butyl dicarbonate in 100 mL CHCl$_3$ with stirring at ambient temperature over 30 minutes. The mixture was stirred for 12 hours, washed with (8×100 mL) water, dried over anhydrous Na$_2$SO$_4$, and concentrated under reduced pressure to yield 8.62 g (85%) of the desired product as a colorless oil. $^1$H NMR (CDCl$_3$, δ) 5.40 (s, 1H, CONH), 3.63 (m, 4H, —OCH$_2$), 3.54 (m, 4H, OCH$_2$), 3.32 (m, 2H, CH$_2$NHCO), 2.87 (t, 2H, CH$_2$NH$_2$), 1.46 (s, 9H), 1.40 (s, 1H, NH$_2$).

Reaction Step 2. Preparation of N-(8-N-Boc-3,6-dioxaoctanyl)biotinamide

To a solution containing 1.00 g (2.54 mmol) 2,3,5,6-tetrafluorophenol ester of biotin in 100 mL CH$_3$CN at 55° C. was added 0.62 g (2.50 mmol) N-Boc-4,7,10-13-trioxa-13-tridecaneamine in 20 mL CH$_3$CN. The mixture was allowed to cool to ambient temperature and then stirred for 8 hours. The solvent was evaporated under reduced pressure and the residue was redissolved in 150 mL EtOAc. The EtOAc solution was washed with (2×75 mL) 10% aqueous NaHCO$_3$ and (2×75 mL) water, dried over anhydrous Na$_2$SO$_4$, and concentrated to yield 1.03 g (87%) as a colorless solid. mp=99–101° C.; $^1$H NMR (CDCl$_3$) δ 6.83 (s, NH, 2H), 6.05 (s, NH, 1H), 5.21 (s, NH, 1H), 4.48 (m, 1H), 4.29 (m, 1H), 3.60 (m, 4H), 3.53 (m, 4H), 3.43 (m, 2H), 3.29 (m, 2H), 3.12 (m, 1H) 2.88 (dd, J=12.8, 4.8 Hz, 1H), 2.73 (d, J=12.8 Hz, 1H), 2.21 (t, 2H), 1.68 (m, 4H), 1.43 (s, 11, t-Butyl and CH$_2$).

Reaction Step 3. Preparation of 8-N-Biotinamide-3,6-dioxaoctaneamine trifluoroacetic acid salt The N-Boc-trioxabiotinamide (1.03 g, 2.17 mmol) was dissolved in 10 mL trifluoroacetic acid and stirred for 30 minutes at ambient temperature. Excess trifluoroacetic acid was evaporated under reduced pressure to yield 0.96 g (90%) of the desired product as an oil. $^1$H NMR (CD$_3$OD) δ 4.10 (m, 1H), 3.90 (m, 1H), 3.28 (m, 4H), 3.24 (m, 4H), 3.14 (m, 2H), 2.95 (m, 2H), 2.79 (m, 1H), 2.51 (dd, J=12.8, 4.8 Hz), 2.29 (d, J=12.8 Hz), 1.81 (t, 2H), 1.25 (m, 4H), 1.02 (m, 2H).

Reaction Step 4. Preparation of N,N',N"-tris(8-N-Boc-3,6-dioxaoctanyl)benzene-1,3,5-tricarboxamide To a solution containing 0.28 g (1.05 mmol) of benzene-1,3,5-tricarbonyl trichloride in 10 mL CH$_2$Cl$_2$ at 0° C. was added 0.74 g (2.98 mmol) 8-N-Boc-3,6-dioxaoctaneamine and 0.70 g (6.91 mmol) triethylamine in 5 mL CH$_2$Cl$_2$. The reaction mixture was stirred under argon for 10 hours at ambient temperature and the volatile material was evaporated under reduced pressure. The residue was redissolved in 150 mL CH$_2$Cl$_2$, washed with 20 mL water, dried over anhydrous Na$_2$SO$_4$, and evaporated to yield 0.82 g (87%) of the desired product as a tacky solid. $^1$H NMR (CDCl$_3$) δ 8.33 (s, 3H), 7.67 (s, ArCONH, 3H), 5.45 (s, Boc-NH, 3H), 3.65 (m, 24H), 3.53 (m, 6H), 3.26 (m, 6H), 1.39 (s, 27H).

EXAMPLE 7

Streptavidin Cross-Linking with Biotin Compounds

This experiment was designed to test streptavidin cross-linking with biotin monomer, biotin dimers comprising water-soluble linkers, and biotin moiety trimers comprising water-soluble linkers. Each of the biotin dimers and trimers used experimentally was water-soluble. That is, each biotin compound had a water solubility in excess of 0.2 mg/mL at neutral pH and ambient temperature. The biotin dimers used herein are structures 28, 29, and 30. The trimers used herein are structures 23 (page 26), 24 (page 26), and 31. The biotin monomer used herein is the N-[13-(p-iodobenzamido)4,7,10-trioxatridacanyl]biotinamide.

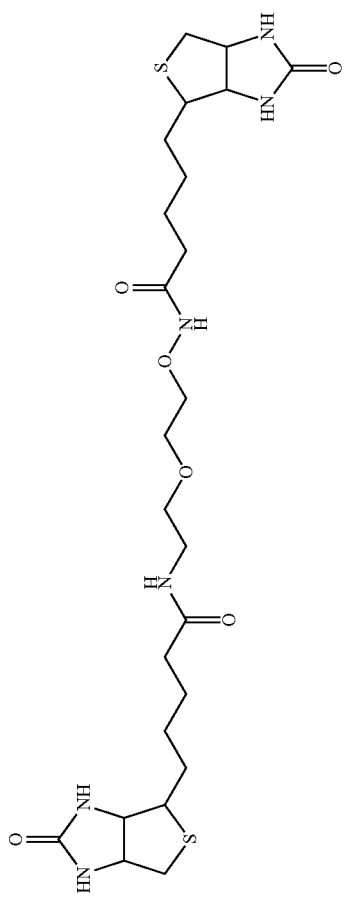
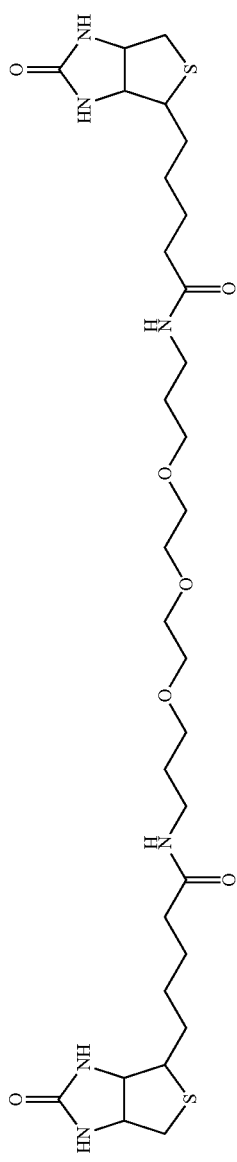
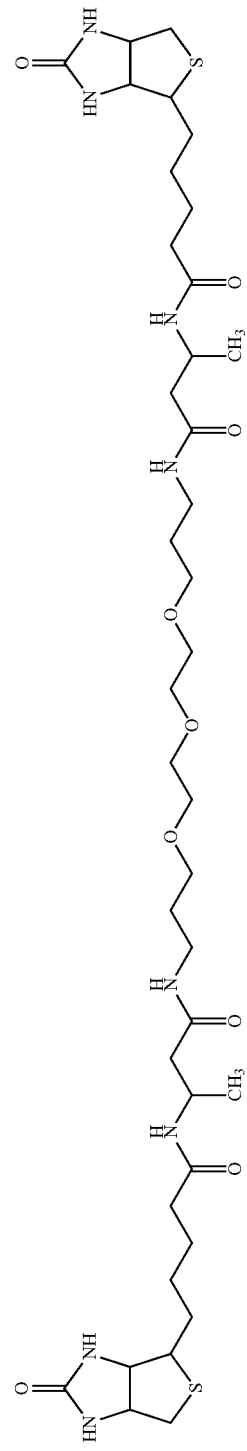

-continued
31
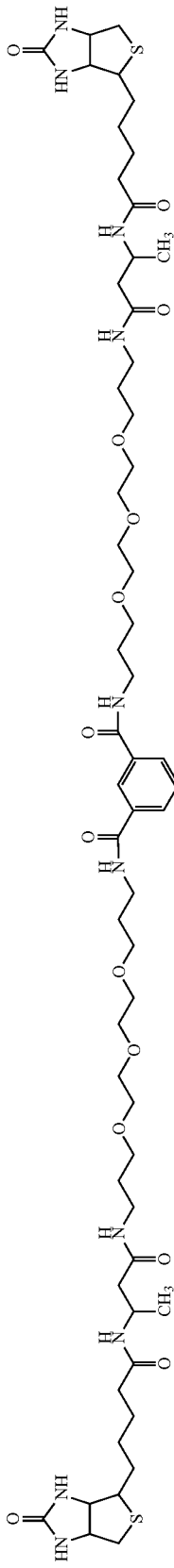
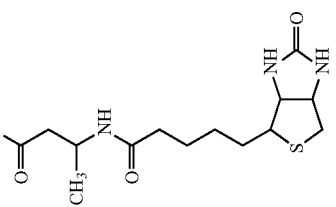

A Reacti-Bind Streptavidin Coated Polystyrene Strip Place (Pierce) was washed with 100 mM PBS prior to use. To lane one (12-wells) was added 100 μL PBS. To lanes 2–7 were added 100 pmol of biotin dimer or biotin trimer to be tested in 100 μL PBS. Lane 8 was treated in the same manner with 100 pmol of biotin monomer. The plate then was incubated at 37° C. with shaking for 10 minutes. All the wells then were emptied and rinsed with 100 μL PBS. The PBS was removed and 25 pmol of $^{125}$I labeled streptavidin (specific activity of 1 μCi/ug) in 100 μL PBS was added to each well. The plate then was incubated with shaking for another 10 minutes. The streptavidin was removed and all the wells were washed with 100 μL PBS.

After removal of the PBS, the first 3 wells of each lane were again filled with 100 μL PBS. The remaining wells were then filled with 100 μL of their respective biotin dimer or biotin trimer as in the first step. The plate then was incubated again for 10 minutes and all wells were rinsed with PBS as before.

Another 100 μL of the radiolabeled streptavidin then was added to all of the wells and 100 μL PBS was added to the first 6 wells of each lane. The remaining 6 wells in each lane were filled with 100 μL of their respective dimer or trimer and again incubated for 10 minutes at 37° C. After removing the liquid in all the wells and washing with PBS, 100 μL of the radiolabeled streptavidin was again added to each well followed by incubation. The streptavidin was removed and the wells washed with PBS.

The first 9 wells in each lane were then filled with 100 μL PBS and the remaining 3 wells in each lane were filled with 100 μL of their respective dimer or trimer. After incubating and washing, 100 μL of radiolabeled streptavidin was again added to each well. After incubating for 10 minutes, each well was washed with 100 μL of PBS and all liquid removed. The wells then were separated and placed in a gamma counter. The amount of activity remaining in each well was determined as a percentage of the highest initial streptavidin binding.

FIG. 1 illustrates the percentage streptavidin binding of the biotin monomer and the dimers and trimers as a function of sequential biotin compound additions. Each of the biotin trimers used demonstrated increased streptavidin binding with each sequential biotin trimer addition. Neither the biotin monomer nor any of the biotin dimers tested demonstrated appreciable increases in streptavidin binding with sequential biotin compound additions.

This experimental data demonstrates that biotin trimers of the present invention can be used successfully to provide amplification of binding sites for complimentary binding moieties, such as streptavidin. The water solubility of such biotin trimers and multimers is particularly important for in vivo applications.

The following examples set forth a general methodology for preparing the biotin/water-soluble reagents, which then are reacted with a cross-linker of at least tri-functionality. For example, the TFP ester is prepared by esterification of the biotin-trioxaamido-glycolate with tetrafluorophenol. Under the same reaction conditions, any number of activated esters can be prepared by substitution of different phenols, or other alcohols (e.g., N-hydroxysuccinimide).

EXAMPLE 8

Method for Preparing a Water-soluble Biotinylation Reagent that is Reactive with Amines Biotin-4,7,10-trioxa-1,13-tridecanediamine (1 g, 2.24 mmol) was added to a dry flask and dissolved in anhydrous $CH_3CN$/DMF (100/25 mL). To this solution was added 0.4 mL (2.9 mmol) triethylamine, followed by 0.31 g (2.7 mmol) diglycolic anhydride. The reaction was stirred at room temperature for 1 hour, and the solvent was removed under vacuum. The product was triturated in 100 mL ether and filtered. The resultant filtrate was dried under vacuum to yield 1.26 g (99%) of desired product as a colorless solid, mp 117–119° C.; $^1$H NMR($CDCl_3$, δ): 1.3–1.7 (m, 10H), 2.1 (t, 2H), 2.7 (d, 1H), 2.8 (dd, 1H), 3.1 (m, 1H), 3.2–3.3 (m, 4H), 3.4–3.55 (m, 13H); 3.99 (s, 2H), 4.07 (s, 2H), 4.28 (m, 1H), 4.43 (m, 1H), 5.9 (s, 1H), 6.8 (m, 2H), 7.4 (t, 1H).

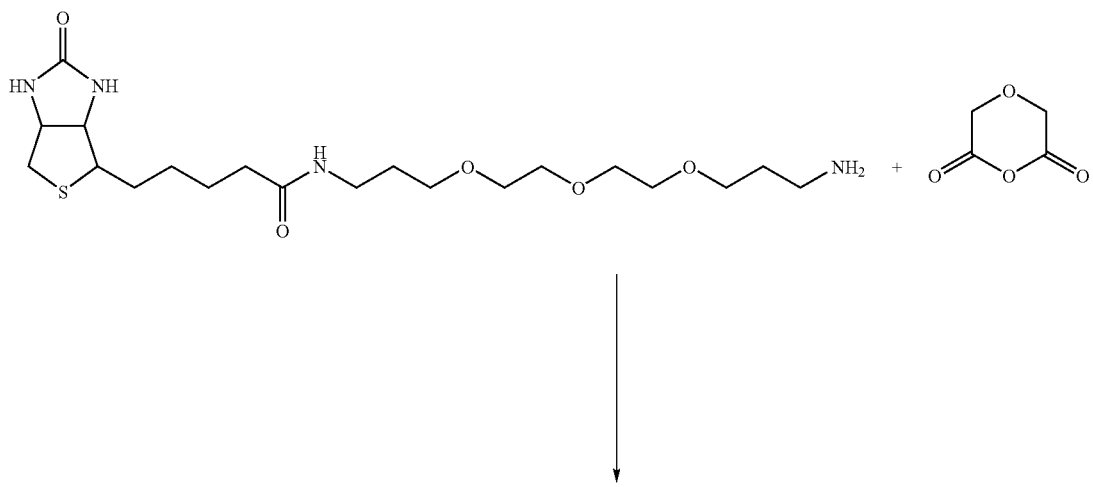

-continued

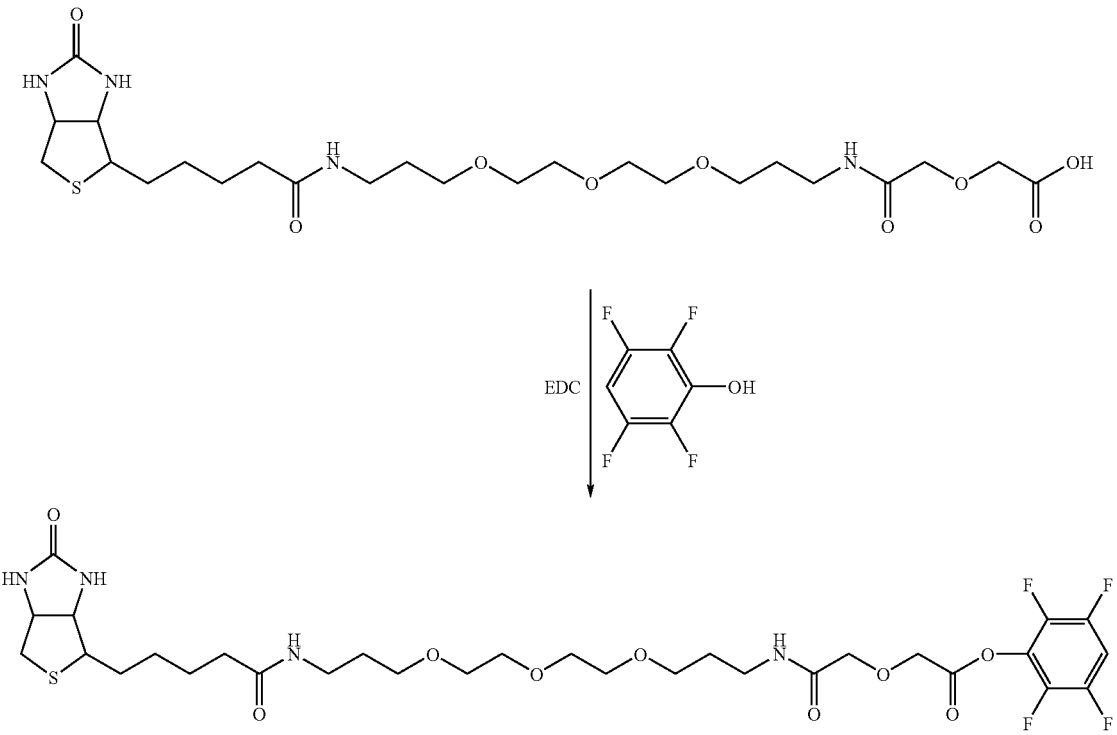

The biotin-4,7,10-trioxa-1,13-tridecanediamine-diglycolic carboxylate (1.0 g, 1.78 mmol) thus prepared, then was placed in a dry flask and dissolved in anhydrous $CH_3CN$/DMF (75/25 mL). Tetrafluorophenol (2.13 mmol, 0.353 g) was added to the solution followed by 0.41 g (2.13 mmol) of EDC. The reaction mixture was stirred at room temperature for 1 hour (followed by HPLC), and the solvents were removed under vacuum. The residue was extracted with 200 mL chloroform, washed with (2×25 mL) saturated sodium bicarbonate solution, then with (2×50 mL) water. The chloroform solution was dried over anhydrous sodium sulfate and the chloroform removed under vacuum. The product was tritrated in 100 mL ether and was filtered. The filtrate was dried under vacuum to yield 0.8 g (63%) of desired product as a solid. $^1H$ NMR($CDCl_3$, δ) 1.3–1.8 (m, 10H), 2.1 (t, 2H), 2.7 (d, 1H), 2.8 (dd, 1H), 3.1 (m, 1H), 3.2–3.6 (m, 15H), 3.8 (t, 2H), 4.08 (s, 1H), 4.27 (m, 3H), 4.4 (m, 2H), 5.7 (s, 1H), 6.4 (s, 1H), 6.5 (m, 1H), 7.0 (m, 1H).

EXAMPLE 9

Method for Preparing a Water-soluble Biotinylation Regent that is Reactive with Sulfhydryls or Amines Biotin-4,7,10-trioxa-1,13-tridecanediamine (1.0 g, 2.2 mmol) was dissolved in 12 mL of saturated aqueous sodium bicarbonate and cooled with ice water. N-methoxycarbonyl-maleimide (4.5 mmol, 0.696 g) was added and the reaction stirred at 0° C. for 10 minutes. A 50 mL quantity of water was added to the reaction and the stirring was continued at room temperature for an additional 15 minutes. The solution was extracted with (4×100 mL) chloroform. The combined chloroform extracts were washed with (2×50 mL) water, dried over anhydrous sodium sulfate, and chloroform removed under vacuum. The product was triturated in 100 mL ether and filtered. The isolated product was dried under vacuum to yield 0.57 g (49%) of the compound 18 as a colorless solid; mp=112–114° C.; $^1H$ NMR (MeOH, δ): 1.46 (m, 2H), 1.6–1.8 (m, 9H), 2.2 (t, 2H), 2.7 (d, 1H), 2.9 (dd, 1H), 3.2–3.3 (m, 4H), 3.5–3.6 (m, 15H), 4.3 (m, 1H), 4.5 (m, 1H), 6.8 (s, 2H); IR (KBr, $cm^{-1}$): 3280, 2910, 2850, 1760, 1690, 1640, 1110, 940; HRMS: calculated for $C_{24}H_{38}N_4O_7S$ (M+H) is 527.2539, found 527.2526.

EXAMPLE 10

Method for Preparing a Water-soluble Biotinylation Reagent that is Reactive with Aldehydes, Ketones, and Oxidized Carbohydrates A solution of 0.5 g of biotin-trioxamido-glycolate TFP ester in 50 mL anhydrous THF was added dropwise to a solution containing 5 mL anhydrous hydrazine in THF at 0° C. After the addition was complete, the reaction solution was allowed to come to room temperature over a 1-hour period. The THF and excess hydrazine were removed under vacuum. The residue was triturated with 100 mL ether and the product (compound 20) collected by filtration.

EXAMPLE 11

Biotinidase Resistant Biotinylation Reagent

This experiment was conducted to examine the stability of water solubilized, radioiodinated biotin derivatives toward biotinidase degradation in mouse and human serum. Control and Experimental derivatives were synthesized to conduct the study. The biotin derivatives synthesized contained: 1) the biotin moiety; 2) a water solubilizing linker moiety; 3) p-iodobenzoate or p-tri-n-butylstannylbenzoate moiety; and 4) the experimental compounds containing N-methyl or α-methyl moiety to block biotinidase activity. The water-soluble linker moiety, 4,7,10-trioxa-1,13-tridecanediamine, was included in the biotin derivatives to improve their water solubility and it also functioned as a 17 Å spacer between the biotin and the benzoyl moieties. Thus, the compounds that were designed to be stable to biotinidase incorporated N-methyl and a-methyl moieties adjacent to the biotin carboxylate group. To measure the biotinidase resistance of the radioiodinated experimental compounds, each was incubated in mouse or human serum at 37° C. for 2 hours. Excess streptavidin then was added to bind with the biotin. The solutions then were filtered through a size exclusion centrifugation membrane. Radioactivity that passed through the membrane represented biotinidase that had cleaved the molecule. The results indicated that the biotin derivatives, which had no functional group for blocking the biotinidase, were rapidly degraded by the enzyme. The biotin derivatives containing the N-methyl-biotinamide functionalities were found to be slightly more stable to biotinidase degradation than the α-methyl biotinamide functionality and significantly more stable than the unprotected control biotin compound.

Other biotinidase blocking groups, such as α-amino acids, can be used in the present invention. Further, the biotin amide can be reduced to an amine. In addition, the pentanoic acid side chain in biotin can be shortened or lengthened. Thus, compounds such as norbiotinamine, homobiotinamine, and their isothiocyanto derivatives can be used to prepare biotin-containing compounds that are resistant to biotinidase activity.

EXAMPLE 12

Biotinylated Starburst Dendrimers

In this experiment, a series of biotinylated starburst dendrimers (BSBDs) were prepared and evaluated in vitro and in vivo. Starburst dendrimers (SBD) of increasing sizes are given the terminology of "generations" as they are built up from "shells". The generations (abbreviated G) used were 0 (G=0; 4 terminal amines); 1 (G=1; 8 terminal amines); 2 (G=2; 16 terminal amines); 3 (G=3; 32 terminal amines); and 4 (G=4; 64 terminal amines). SBD nomenclature and chemistries are provided in a publication by Tomalia and Durst, "Genealogically Directed Synthesis: Starburst/Cascade Dendrimers and Hyperbranched Structures", *Topics in Current Chem.*, 165, 193–313 (1993).

Five (5) SBDs were biotinylated with 12-N-Biotinyl-(N-methyl) amino-4,7,10-trioxado-decanoic acid tetrafluorophenyl ester 27 (prepared in Example 4) (BTDT). BTDT is a useful biotinylation reagent as it has a low molecular weight (e.g., 445 g/mol for the conjugated moiety), and contains water solubilizing ether functionalities and a N-methyl functionality for stabilization against biotinidase cleavage. The SBDs (G=0, 1, 2, 3 and 4) were obtained as 10–20% by weight solutions in methanol. After removing the methanol under vacuum, the SBDs were reacted with an excess of BTDT 14 in dimethylformamide at room temperature. The crude products were purified by silica gel column chromatography. Mass spectra data confirmed the identify of the compounds prepared. All the SBDs were full perbiotinylated except G=4 (64 terminal amines). From the mass spectra, it appeared that G=4 only added 51 biotin moieties and not the predicted 64. It is likely that longer reaction times and/or elevated reaction temperatures could add more biotin moieties to G=4.

The BSBDs were radioiodinated so that their in vivo distribution could be evaluated. Radioiodination was accomplished by reacting sub-stoichiometric quantities of the amine reactive p-[$^{125}$I] iodobenzoate NHS ester with the SBD prior to reaction with the BTDT. The low stoichiometric quantity of the NHS ester was used to assure that only one iodobenzoate was incorporated in the radiolabeled polybiotin compounds.

Once the BSBDs had been prepared, an assessment of the number of radiolabeled streptavidin molecules ([$^{125}$I]SAv) that bound each of the BSBDs was made. To accomplish this, an assay was used in which unlabeled BSBDs were bound with immobilized streptavidin (SAv) in polystyrene wells (similar to Example 7), then radioiodinated SAv was bound to the exposed biotin moieties. In the studies, the pmol quantity of [$^{125}$I]SAv bound after saturating the biotin binding sites with unlabeled BSBDs was measured. Those values, shown graphically in FIG. 2 were obtained directly from the radioactivity measurements and the specific activity of the added [$^{125}$I]SAv. However, to obtain an estimate of the average number [$^{125}$I]SAv molecules bound with each BSBD (after one addition), an assumption had to be made. That assumption was that the pmol quantities required for 1 equivalent of [$^{125}$I]SAv binding was equal to the amount of [$^{125}$I]SAv bound with the biotin tetramer (G=0). The rationale for using this assumption was that the value obtained (3.6±0.2 pmol) was very close to that previously obtained for biotin trimers (see Example 7) in the same assay system, and it seems most likely that G=0 would bind with 1 molecule of [$^{125}$I]SAv after binding with immobilized SAv. If one uses the 3.6 pmol value for each equivalent of [$^{125}$I]SAv bound, the number of equivalents of [$^{125}$I]SAv bound with the BSBDs can be readily estimated. By definition, BSBD (G=0), which has four (4) biotin moieties, bound with one equivalent of [$^{125}$I]SAv and one equivalent of polymer bound SAv. In the BSBD (G=1), the number of biotin moieties is 8. If two of the biotin moieties on BSBD (G=1) are bound to the immobilized SAv, it might be estimated that 3 additional [$^{125}$I]SAv molecules could bind (assuming 2 biotin moieties bound each SAv molecule). Instead, a doubling was seen, binding 2 equivalents of [$^{125}$I]SAv. Similarly, with the BSBD (G=2), which has 16 total biotin moieties, 4 equivalents of [$^{125}$I]SAv bound in addition to binding with SAv on the plate. No additional increase in the number of [$^{125}$I]SAv molecules bound were found with BSBD (G=3; 32 biotin moieties) or BSBD (G=4; up to 64 biotin moieties when perbiotinylated).

The smaller number of [$^{125}$I]SAv molecules bound to the SAv-coated plates than had been predicted, based on the number of biotin moieties (pairs) available, might be the result of steric hindrance. This same explanation may account for the lack of increased binding observed for G=3 and G=4 over that observed for the smaller BSBDs. However, one cannot rule out the possibility that, as the BSBD molecules get larger, fewer of them bind with the immobilized SAv. Fewer molecules of the larger BSBDs might bind if: 1) more than one immobilized SAv bound with each BSBD molecule, and/or 2) if steric hindrance from the bound BSBD molecules precluded binding of more [$^{125}$I] SAv molecules. Another consideration is that after reaching a certain size, more than 2 biotin moieties might bind with each SAv molecule. Through computer modeling, it was estimated that it would take a linker of >6 Å length (biotin carbonyl carbon to second biotin carbonyl carbon) to bind at opposite faces of SAv. The estimated bond distances between any two biotin moieties in the SBDs G=1–4 appear to be adequate for more than 2 biotin moieties to bind with a single SAv molecule. Irrespective of the explanation for the results obtained, there appears to be no advantages for use of BSBDs larger than generation 2 (G=2).

Even though a smaller number of SAv molecules were attached to the immobilized BSBDs than might be predicted, substantial amplification of the amount of radioactivity bound to the SAv coated plates was obtained. From Example 7, it was known that in a single addition, cross-linking with biotin trimers in the same assay system resulted in 4–6 pmol of [$^{125}$I]SAv bound per well. Further, it was demonstrated that a doubling of that quantity (10–12 pmol) of [$^{125}$I]SAv was obtained in 4 alternating cycles of reagent additions. However, much larger quantities (16–30 pmol) of [$^{125}$I]SAv were bound when biotinylated SBDs (G=2, 3, or 4) were used. Indeed, with one addition of the biotin multimers (G=2, 3, or 4), there was a 300% increase of [$^{125}$I]SAv bound over that of a single addition of the biotin trimers and a 40+% greater quantity bound than obtained previously with four alternating administrations of the biotin trimers. These results support the potential for amplification of tumor targeting of radioactivity using the biotin multimers according to the invention and radiolabeled SAv.

As the ultimate goal is to use the BSBDs for in vivo application to tumor pretargeting of radionuclides for cancer therapy, it is important to evaluate the in vivo distribution and pharmacokinetics of the BSBDs. Example 7 demonstrates biotin trimers cross-linked SAv in the coated wells, but did not investigate in vivo distribution. Therefore, radiolabeled biotin trimers as carriers of radionuclides were included in the following in vivo evaluation. The BSBD, which has 15 biotin moieties (G=2), appeared to be the best candidate for in vivo amplification of binding sites, but the intermediate size of BSBD (G=1) made its in vivo distribution of interest as well. Although it is envisioned that the perbiotinylated SBDs (G=1 or 2) will not be radiolabeled for in vivo use, it was necessary to radiolabel them to assess their biodistribution. It was assumed that these radioiodinated versions of the biotinylated dendrimers would have a distribution similar to the perbiotinylated SBDs.

In this investigation, it was determined that it would be adequate to obtain comparative information about the tissue distribution of the three BSBDs (G=0, 1, and 2) in athymic mice at one time point (e.g., 4 hours post injection).

A generalized reaction of starburst dendrimers (SBD) with [$^{125}$I]PIB NHS ester and biotinylation reagent 27 is set forth below:

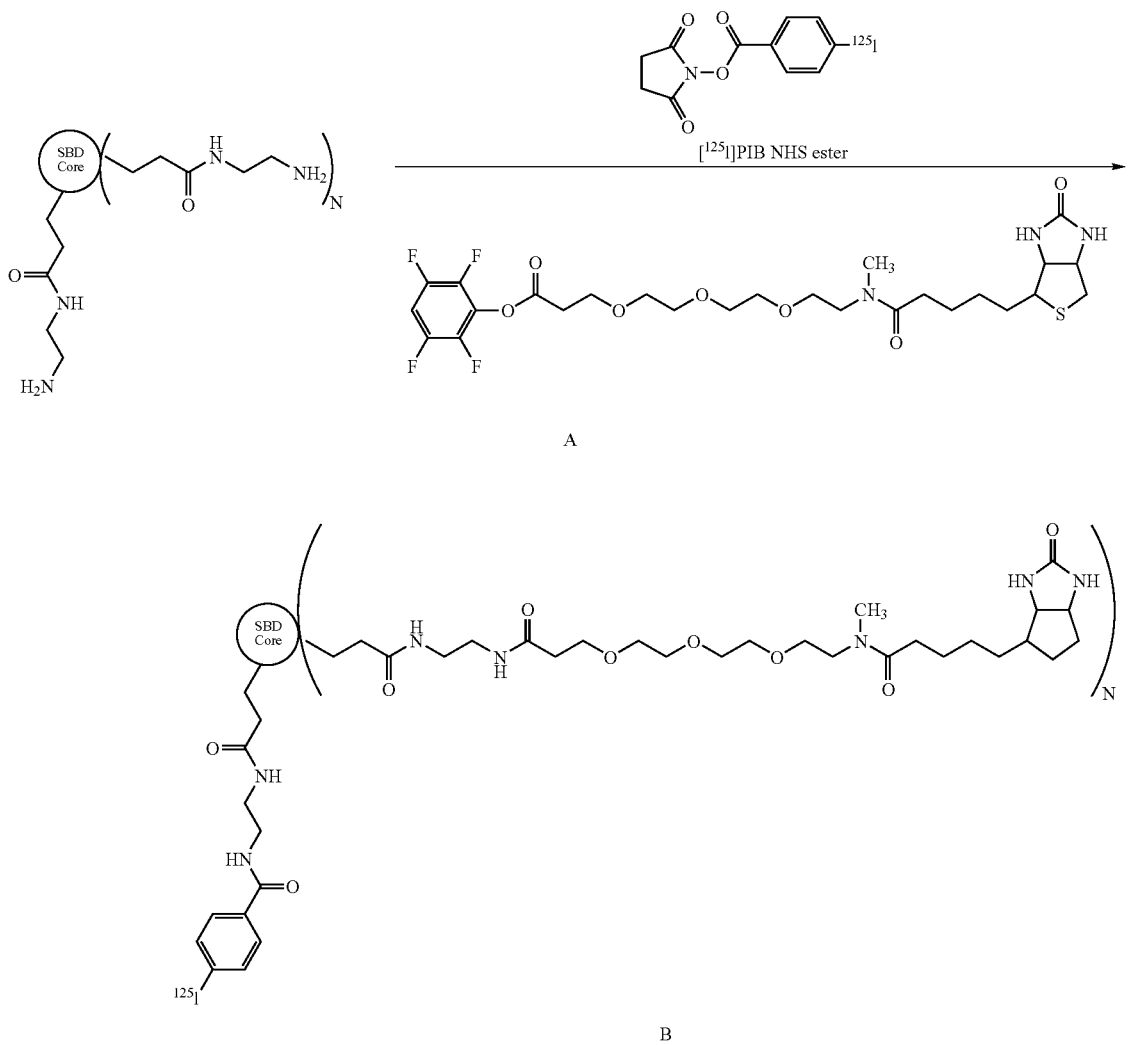

TABLE 1

| Starting Dendrimer[a] A | MW (amu) | Reaction time (days) | Biotin moieties[b] N | Product B | MW[c] (amu) | Radiochemical yield (%) |
|---|---|---|---|---|---|---|
| 32; SBD, G = 0 | 517 | 3 | 3 | [$^{125}$I]35 | 2077 | 54 |
| 33; SBD, G = 1 | 1430 | 3 | 7 | [$^{125}$I]36 | 4765 | 28 |
| 34; SBD, G = 2 | 3256 | 3 | 15 | [$^{125}$I]37 | 10140 | 40 |

[a]The starburst dendrimer core for each generation (G) is composed of the previous generation, except the terminal primary amines are substituted with two of the groups shown in parentheses in structure A.
[b]This is the maximum number that can be attached under normal conjugation reaction conditions.
[c]The molecular weight has been calculated with the predominant iodine nuclide, iodine-127.

The results of the investigation are shown in Table 2.

TABLE 2

Distribution of Radioactivity for [$^{125}$I]BSBDs in Athymic Mice[a]

| TISSUES | [$^{125}$I]35[b] | [$^{125}$I]36[c] | [$^{125}$I]37[d] |
|---|---|---|---|
| Blood | 0.20 ± 0.04 | 0.13 ± 0.02 | 0.20 ± 0.03 |
| Muscle | 0.04 ± 0.00 | 0.04 ± 0.00 | 0.08 ± 0.03 |
| Lung | 0.26 ± 0.05 | 0.18 ± 0.01 | 0.62 ± 0.19 |
| Kidney | 8.28 ± 2.92 | 16.95 ± 2.82 | 47.64 ± 7.08 |
| Spleen | 0.26 ± 0.11 | 0.20 ± 0.04 | 0.70 ± 0.07 |
| Liver | 1.50 ± 0.10 | 1.79 ± 0.22 | 7.06 ± 1.23 |
| Intestine | 3.77 ± 3.65 | 0.74 ± 0.66 | 1.34 ± 1.93 |
| Urine[e] | 33.39 ± 36.85 | 9.70 ± 10.25 | 0.43 ± 0.09 |
| Stomach | 0.25 ± 0.08 | 0.14 ± 0.03 | 0.47 ± 0.11 |

[a]Values shown are average % injected dose/gram ± standard deviation; sacrifice was 4 h post injection; data were obtained for n = 5 mice per group; average animal weight, 24.61 ± 2.28 g; all injections were made in approximately 100 mL of 0.9% sterile saline.
[b]Injectate for each animal had 10 mCi/284 mg of [125I]35.
[c]Injectate for each animal had 10 mCi/70 mg of [125I]36.
[d]Injectate for each animal had 10 mCi/59 mg of[125I]37.
[e]Urine was collected by syringe bladder tap after sacrifice.

Interestingly, the concentrations of radiolabeled BSBDs in blood at 4 hours post injection are nearly the same. Differences in distribution between radiolabeled BSBDs are minor except for the kidney and liver concentrations. In previous distributions of radioiodinated biotin monomers in mice, blood clearance was similar at 4 hours to that found for G=0, but quite high intestine concentrations were observed (unreported results).

EXAMPLE 13

Altering the Charge of Multi-Biotin Containing Compounds

From the experiments presented above using the SBDs as the crosslinking agent (C), it was noted that the multi-biotin-containing compounds acquired a net overall charge. The net charge that occurs naturally may be desired in certain applications, but it may also be problematic. Therefore, alteration in the charge of the molecule may be desired. Alteration of the charge is readily achieved by preparing the multibiotin molecules using biotin conjugates, preferentially certain biotin-amino acid conjugates. For example, two biotin-aspartate derivatives (40 and 41) can be formed from the reaction of the appropriately protected aspartic acid as shown below.

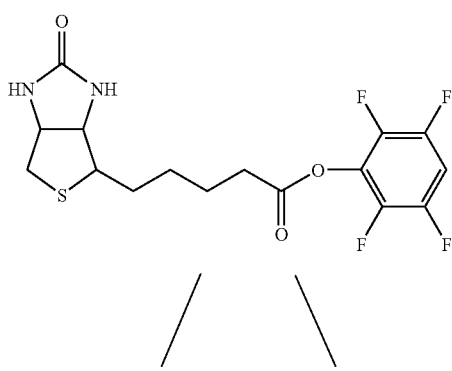

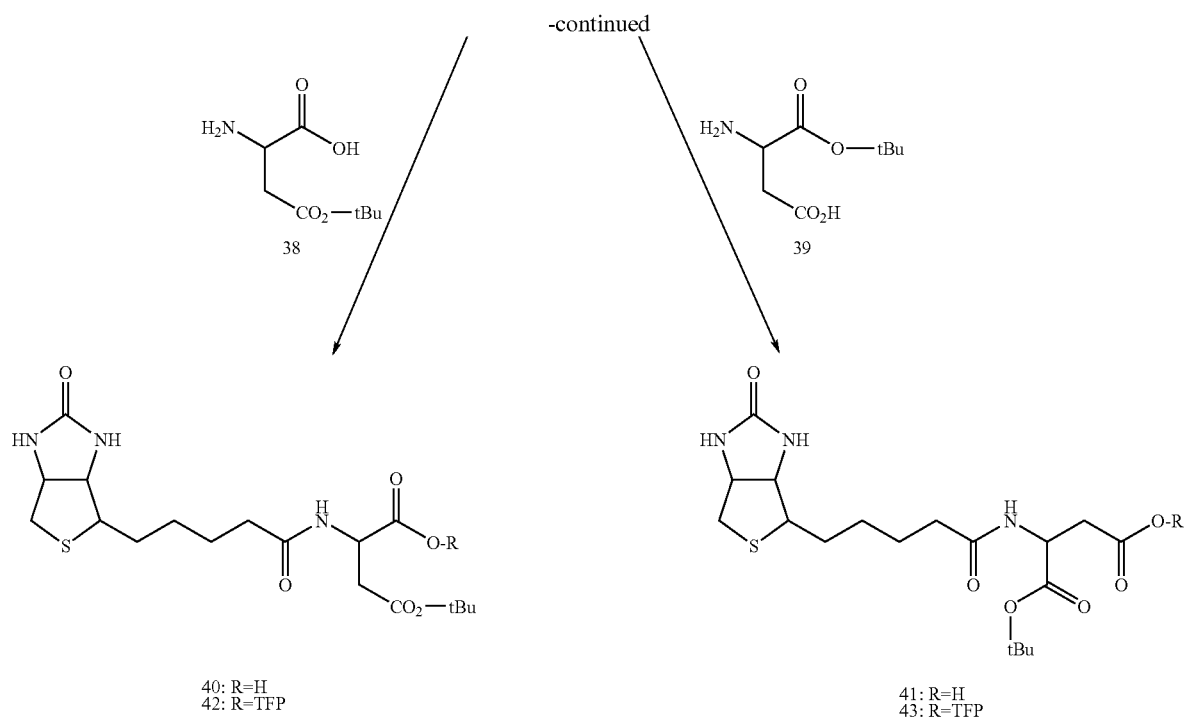

The aspartate tert-butyl esters 38 and 39 were purchased from a number of commercial sources. Reaction of 38 or 39 with the tetrafluorophenyl (TFP) ester of biotin, provided adducts 40 and 41, respectively, in high yields. The TFP esters of 40 and 41 were readily prepared using tetrafluorophenyl trifluoroacetate to give biotin-aspartate conjugates 42 and 43. Either of these compounds can be reacted with amine (or polyamine) containing compounds (e.g., SBDs) to form multi-biotin-containing compounds. Treatment with trifluoroacetic acid cleaved the t-Bu esters to form free carboxylates. While this reaction yields useful biotin-dendrimer compounds, the preferred biotin-dendrimer compounds contain a water solubilizing linker moiety between the core dendrimer and the biotin derivative. Thus, as a preferred example, the synthesis of a biotin-aspartate derivative, which also contains a trioxtridecane linker and an isothiocyanate moiety for reaction with amines, is depicted below.

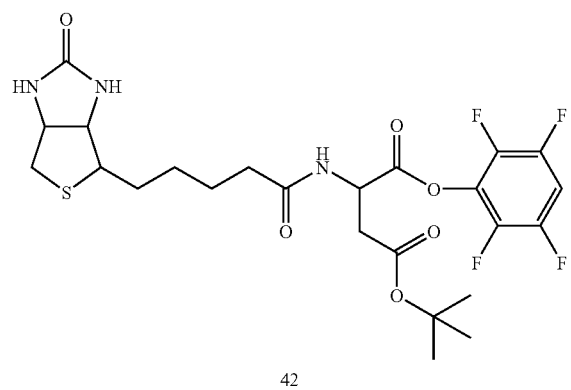

42

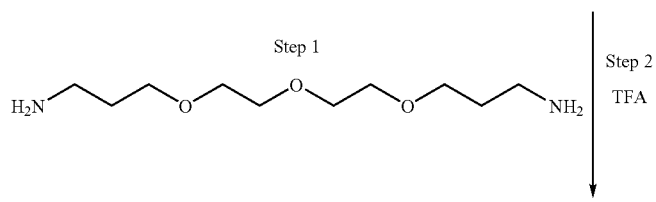

-continued

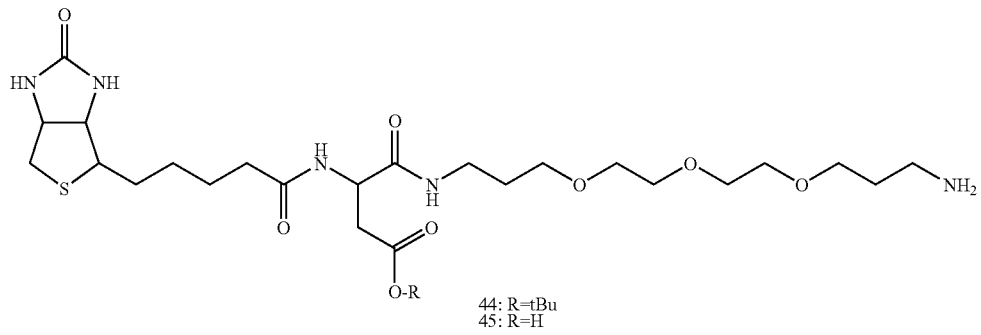

44: R=tBu
45: R=H

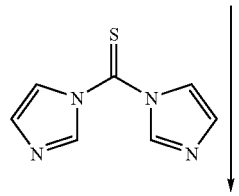

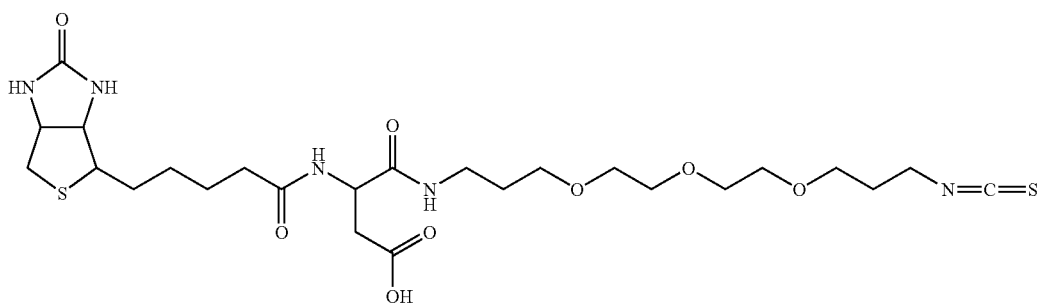

46

Reaction of biotin-aspartate TFP ester 42 with trioxatridecanediamine yielded the adduct 44. The t-butyl ether was cleaved from 44 with trifluoroacetic acid (TFA) and the amine functionality was converted to an isothiocyanate group with diimidazolethiocarbonyl, to yield the desired biotinylation reagent 46. The same chemistry works with the other biotin-aspartate TFP ester described above.

Under physiological conditions (e.g., pH 7) the aspartate carboxylates deprotonate to yield a negative charged species. These anionic biotin derivatives then were reacted with a starburst dendrimer, generation 2 (SBD, 2), which has 16 reactive amino groups. After addition of 16 biotin moieties (see Example 12), the net charge on the resulting biotinylated dendrimer was +14. It is believed that this high positive charge causes these compounds to be accumulated/retained in the kidney (see Table 2). Reaction of starburst dendrimer, generation 2, with, for example, with biotin aspartate derivative 46, provides the starburst dendrimer 47 that is shown below. Under physiologic conditions, this multibiotin compound has a net charge of −2.

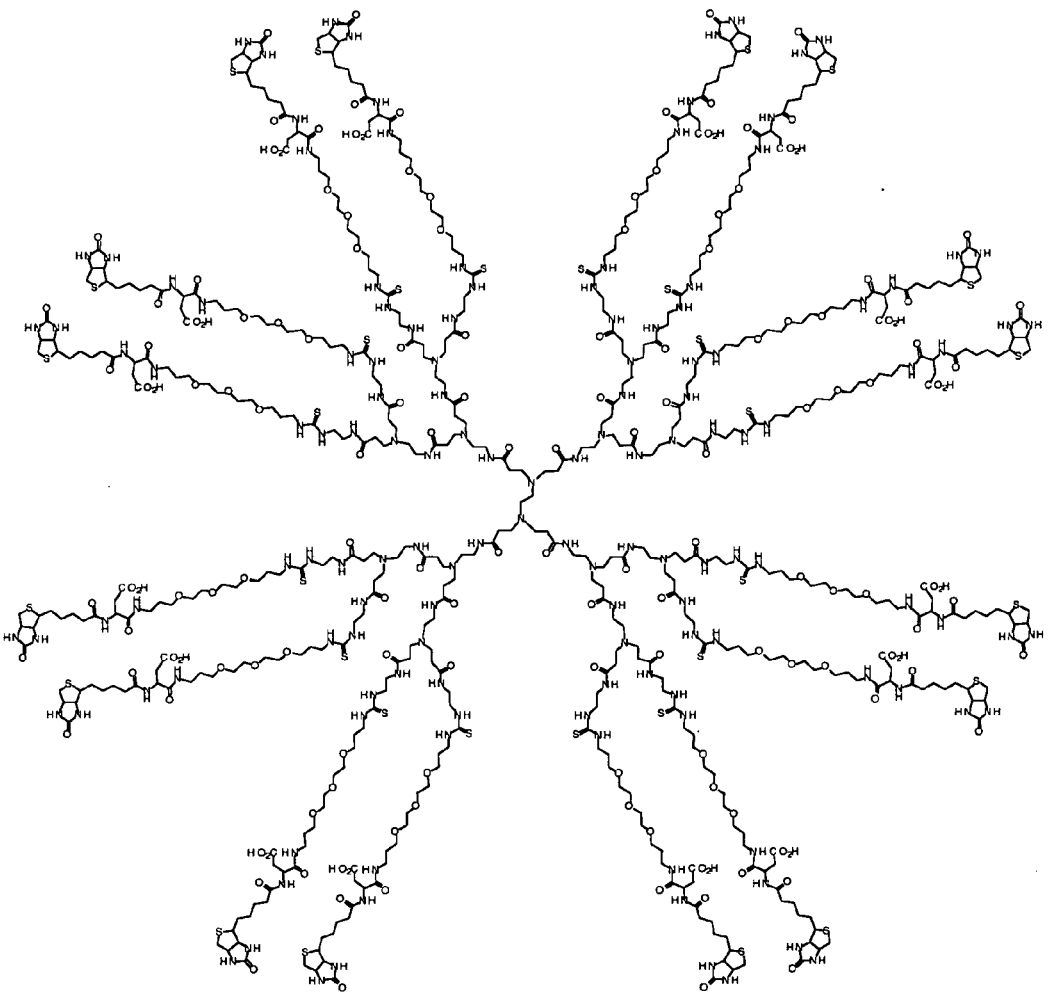
47

The foregoing depicts biotin derivatives with added negative charges to multi-biotin-containing compounds. Negatively charged cross-linkers (C) (e.g., polycarboxylates) may require the addition of positively charged biotin derivatives to provide more favorable characteristics to the final biotin-containing compound. In such examples, addition of an appropriately protected lysine to biotin to form an adduct will achieve the desired effect. An example of the synthesis of a biotin-lysine adduct, 48 is provided below.

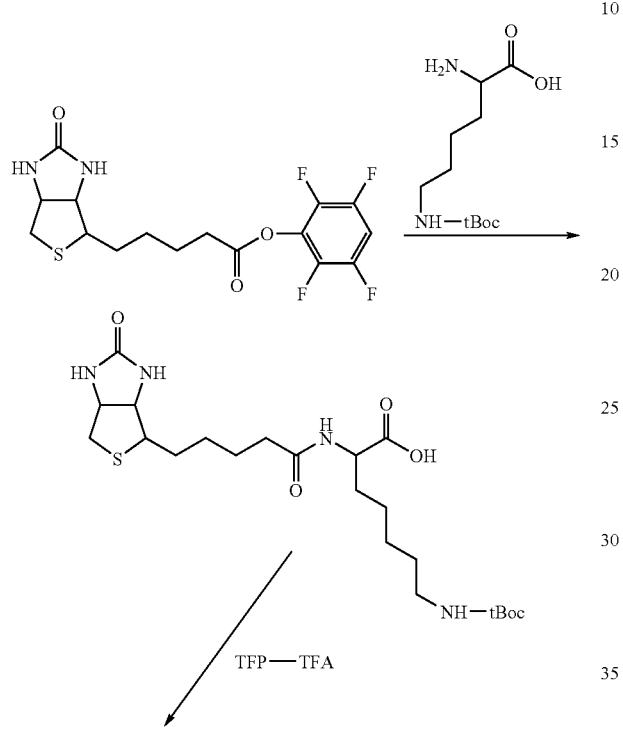

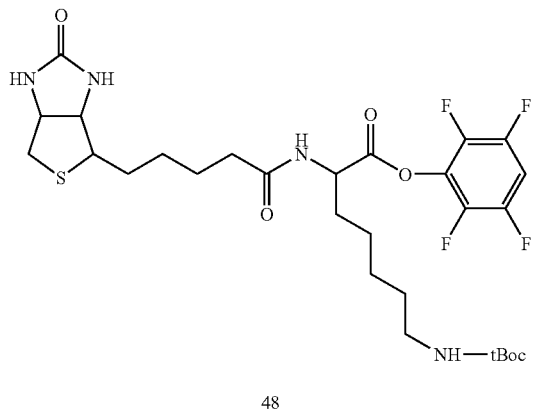

48

This compound can be conjugated with chemical entities bearing amines or a linker, such as 4,7,10-trioxa-1,13-tridecanediamine, and added before the reaction with the cross-linker. The t-Boc protecting group can be removed with TFA. The resulting free amine will have a positive charge at physiologic conditions. The net charge of the multibiotin containing compound according to the invention is dependent on the number of biotin-lysine adducts added in addition to the other charged moieties present. The addition of charged species generally improves the water solubility of multi-biotin-containing compounds; however, alteration of charges on the species may not be desired. Therefore, in certain circumstances, it may be desirable to increase the aqueous solubility of biotin multimers by the addition of another, non-charged species. This can be achieved by preparation of a biotin-serine adduct as shown below.

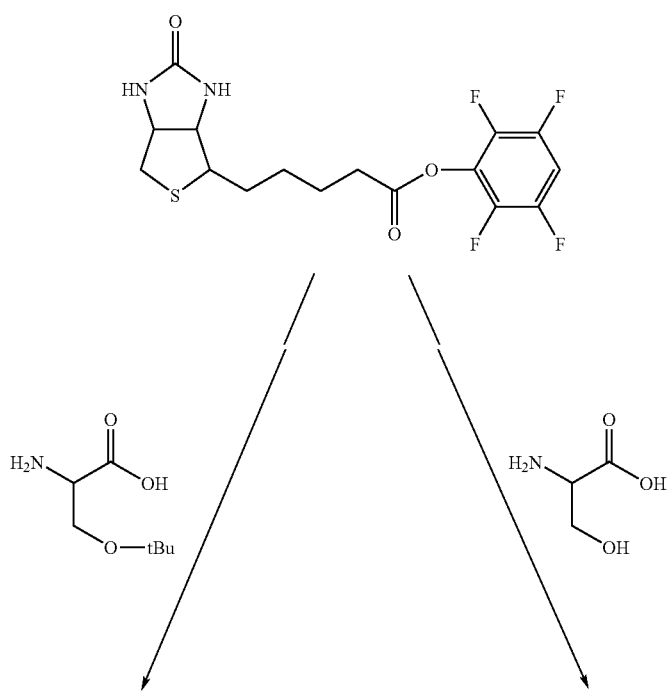

-continued

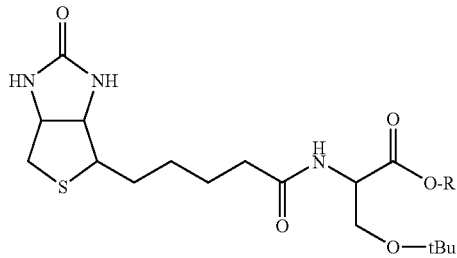

49: R=H
50: R=TFP

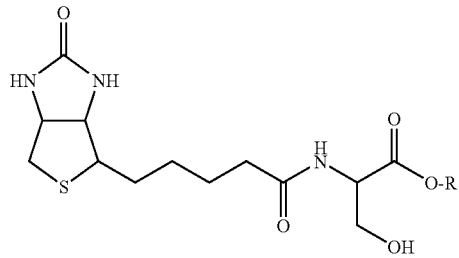

51: R=H
52: R=TFP

Two (2) biotin-serine adducts can be prepared, one with a t-Bu ether functionality, 49, and the other with a free hydroxyl moiety, 51. The tetrafluorophenyl esters, 50 and 52, can be prepared readily using tetrafluorophenyl trifluoroacetate (TFP-TFA). Choice of these derivatives will be dependent on the specific requirements of subsequent reactions. As in other multibiotin-containing compounds in accordance with the invention, a linker moiety is added prior to the addition to the cross-linker with at least tri-functionality.

An important aspect of the present invention relates to the placement of an a-amino acid between the biotin moiety (B) and the water-soluble linker moiety to act as a biotinidase protective group (P). The bulky amino acid groups alpha to the biotinamide bond block the action of the enzyme biotinidase. This is very important for in vivo applications of multibiotin-containing compounds in accordance with the invention.

EXAMPLE 14

Mono-Substituted Dendrimers as Cross-Linking Agents

The biotin-containing compounds according to the invention which are provided with a targeting or reporter moiety (e.g., chromophore, radionuclide, etc.) should have only one such moiety attached per molecule. This can be accomplished readily with cascade dendrimers, which are built as branching from one entity (having a protected group for conjugation), but which is not readily produced from starburst dendrimers which are symmetrical. However, methods for preparing polybiotin starburst dendrimers can be achieved by limiting the reagents in a manner that only allows one entity to react with the dendrimer.

Reaction of 12-N-phthalimido-4,7, 10-trixadodecanoate TFP ester with amino terminated dendrimers in 0.5–0.75 molar equivalents provided a monosubstituted dendrimer. As an example, the monosubstituted starburst dendrimer, generation 2, (G=2) was monosubstituted with 12-N-phthalimido-4,7,10-trixadodecanoate TFP ester, then perbiotinylated with the biotinylation reagent, 12-N-biotinyl-(N-methyl)amino-4-7-10-trioxadodecanoic acid TFP ester. The N-phthalimido protected, perbiotinylated dendrimer was obtained in good yield. Subsequent cleavage of the N-phthalimido protection group was attained with hydrazine, and the free amine can be converted to any number of conjugation groups (e.g., isothiocyanate, hydroxylamine or maleimide).

A biotinylated starburst dendrimer (G=2) with N-methyl protection and a maleimide conjugation group of the structural formula:

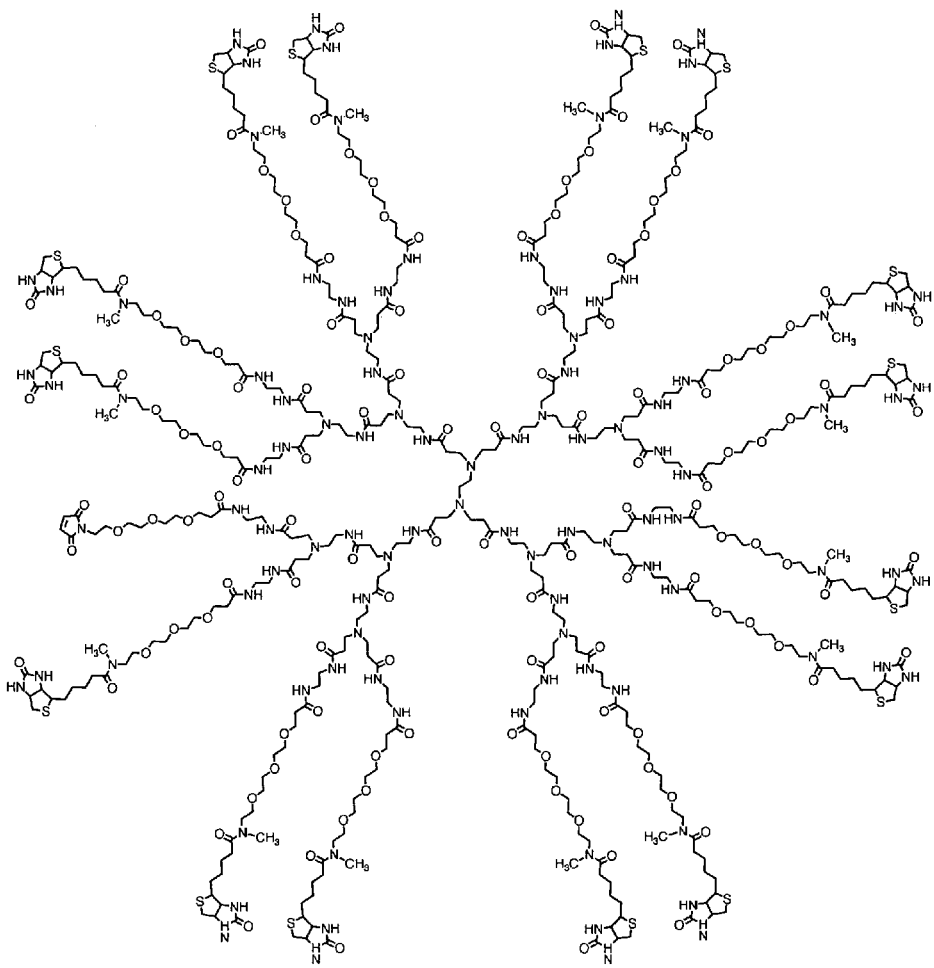

This biotinylated starburst dendrimer (G=2) with N-methyl protection and a maleimide functionality is easily conjugated to a monoclonal antibody (targeting protein) using standard disulfide reduction methods (e.g., dithiothreitol or beta-mercaptoethanol) at room temperature and a pH of 6.5. Similar chemistry is used to provide the monosubstituted N-phthalimido protected starburst dendrimer that has multi-biotin-aspartates (15) conjugated. It is important to note that the net charge on this compound is −1. Minimizing the net charge on perbiotinylated dendrimers conjugated with targeting proteins will minimize the alteration in properties of the targeting protein due to charge. As described previously, the phthalimido protecting group can be removed and the amine can be reacted with another molecule to convert it into a reactive species or it can be directly used to conjugate to another molecule, such as reporter compound (chromophore, radionuclide, etc.).

EXAMPLE 15

Solid Support Preparation

An alternative method to prepare the multi-biotin-containing compounds of the invention uses solid support chemistry methodologies. Thus, an amine reactive form of a Wang Resin can be prepared as described by Brady, et al. in an article entitled: "Discovery and development of the novel potent orally active thrombin inhibitor N-(9-hydroxy-9-fluorenecarboxy)prolyl trans-4-aminocyclohexylmethyl amide (L-372, 460); co-application of structure-based design and rapid multiple analogue synthesis on solid support", *J. Med. Chem.*, 41, 401–406. The amine reactive form of the Wang Resin can be reacted with a large excess of the amine terminated dendrimer to form the adduct as shown below.

83 84
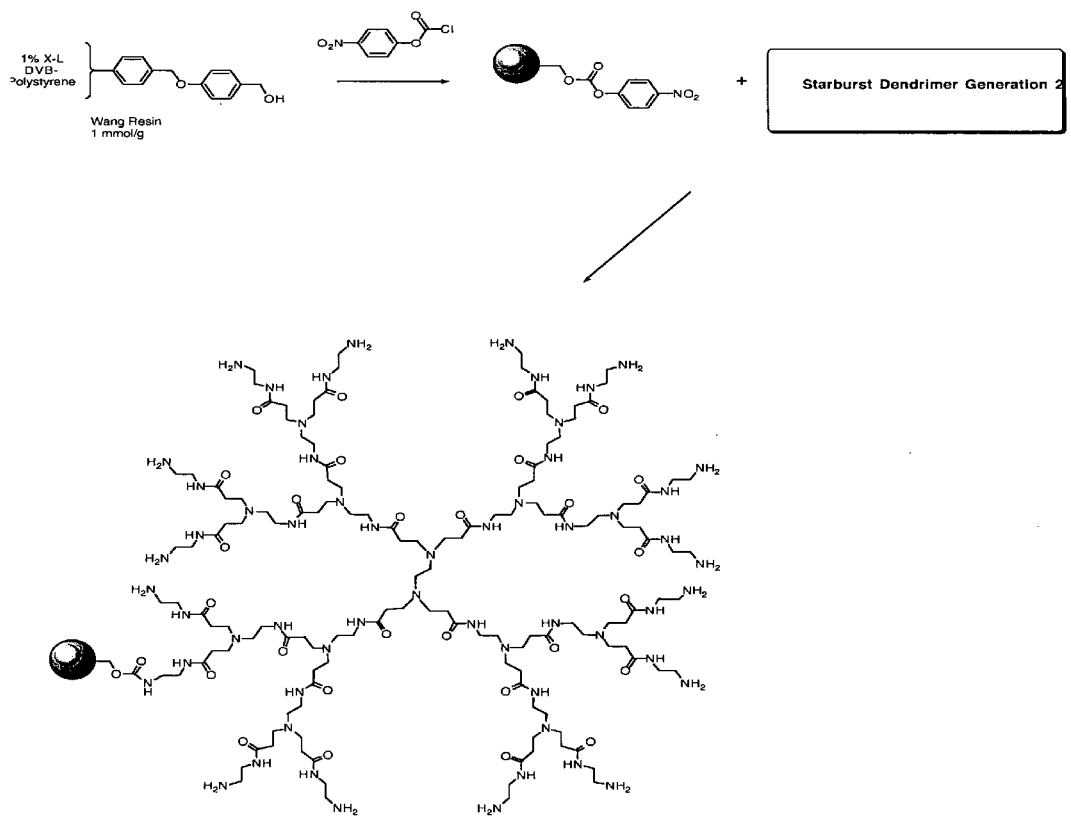

An important aspect of this approach is that separation from the non-reacted dendrimer is facile (filtration and washing) and higher ratios of dendrimer to reactive species can be used as the unreacted dendrimer can be recycled. This latter point allows for only obtaining the monosubstituted dendrimer. Perbiotinylation of the polymer bound dendrimer (e.g., SBD, generation 2) with the biotin aspartate isothiocyanate, 46, is readily accomplished to yield a multi-biotin-containing compound of the structural formula:

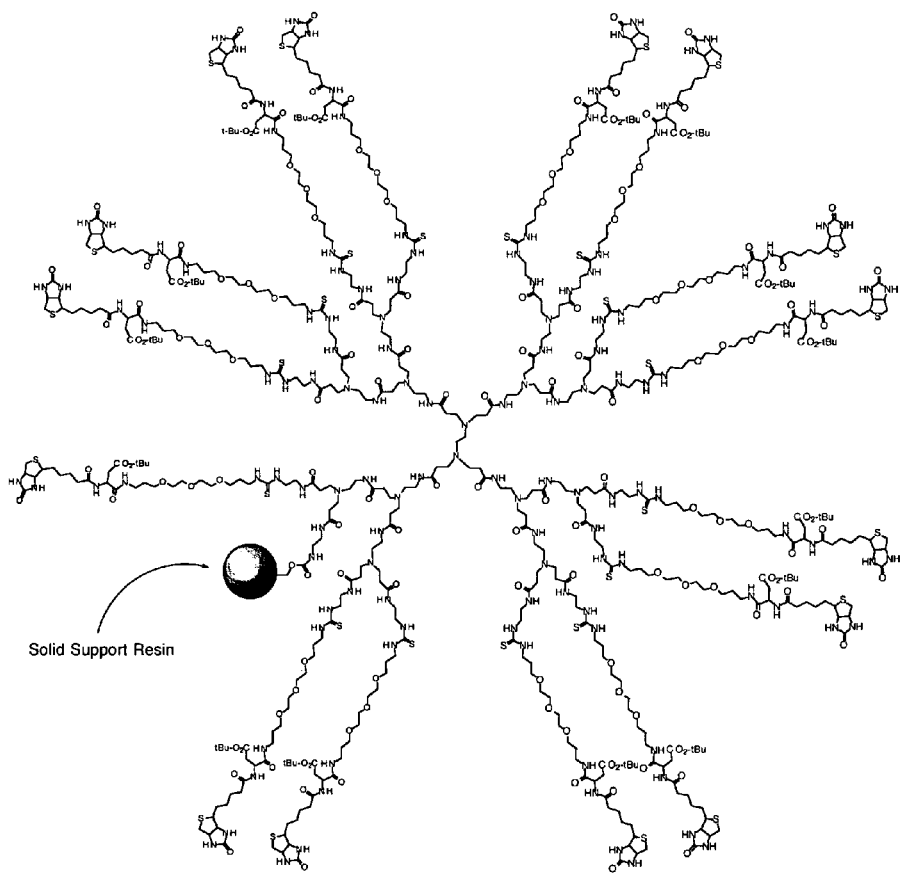

Release from the Wang Resin is accomplished with, for example, trifluoroacetic acid (TFA).

EXAMPLE 16

Detection of Number of Multi-Biotin-Containing Compounds that are Attached to a Targeting Molecule Multi-biotin-containing compounds of the present invention can be conjugated with a variety of carrier or targeting molecules (e.g., antibodies). Based on the structure of the target molecules, reactions will yield a single specific species or a large number of possible reaction products (placed randomly on the molecule). Conjugation with proteins such as monoclonal antibodies is an example where varying numbers of conjugates can be obtained. Use of the standard HABA method for determining the number of biotin moieties present is not applicable as multi-biotin-containing compounds typically have a large number of biotin moieties on each molecule. Therefore, in some multi-biotin-containing compounds that are conjugated to antibodies and the like, it is desirable to have a reporter group attached to the biotin-containing compound. That reporter group may be a radionuclide carrying moiety (e.g., for $^{125}$I) or it may be composed of a chromophoric moiety. The latter is preferred in most examples due to the difficulty in storing and working with radioactive materials.

Addition of a chromophore to the polybiotinylated molecules can be readily attained with the use of solid support synthesis. A preferred method for introducing the chromophore into the multi-biotin-containing compound is to place it between the multi-biotin moiety (e.g., starburst dendrimer) and the conjugation group (group used to attach the targeting molecule). To accomplish this, the chromophore containing compound should be a homo- or heterobifunctional linking reagent. As an example, the fluorescein chromophore can be used and a homobifunctional linking compound containing that chromophore can be prepared as depicted below.

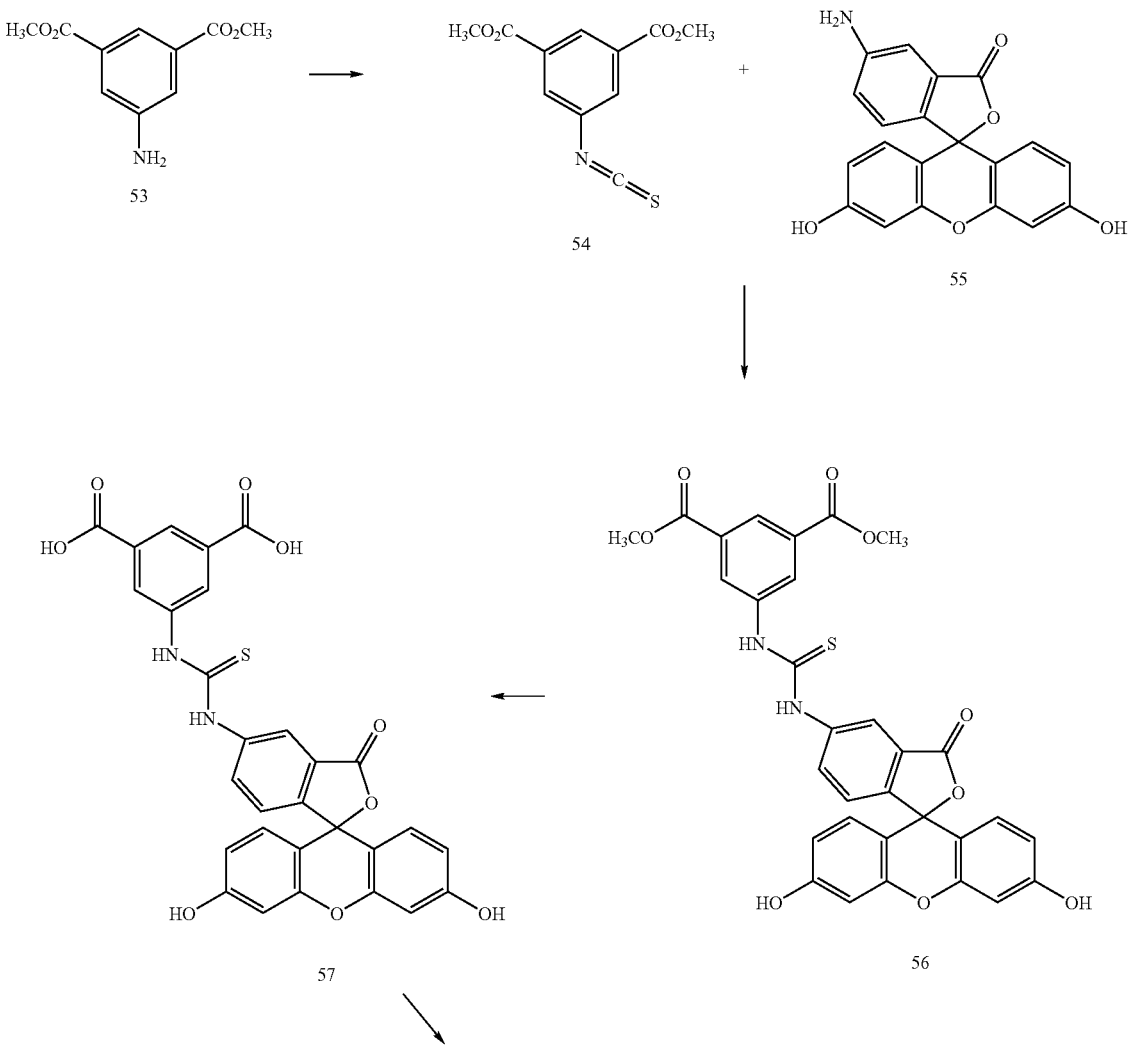

-continued

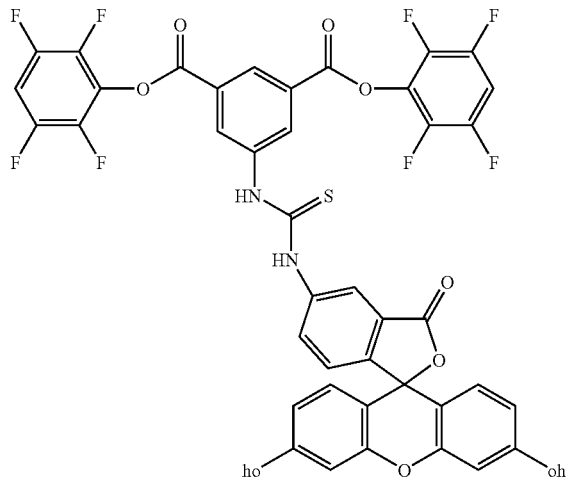

58

Commercially available aminoisophthalate dimethyl ether 53 is converted to the isothiocyanate 54 and that compound is reacted under basic conditions with aminofluorescein (isomer 1) 55 to give the adduct 56. Following this reaction, the methyl esters are removed and TFP esters are formed to make the desired fluorescein containing homobifunctional linking reagent 58. Other bifunctional cross-linking reagents containing alternate chromophores can be prepared in a similar manner.

Incorporation of a chromophore (or fluorophore) into the multi-biotin-containing compounds can be accomplished in a step-wise manner using solid support synthesis. The same methods for preparing the multi-biotin dendrimer, as previously described in Example 15, can be applied. As an example, the homobifunctional cross-linking reagent 58, which contains fluorescein, can be conjugated to a Wang Resin. After activation, reaction with an excess of 4,7,10-trioxa-1,13-tridecanediamine will provide free amines for conjugation of 58. To assure that only one amine reacts with 58, a large excess is used in the conjugation reaction to form polymer supported compound 60. Importantly, the excess quantities of the trioxatridecanediamine and 58 are readily recovered to be used in other reactions. This reaction scheme is set forth below:

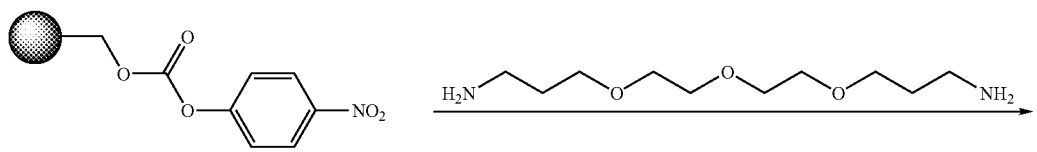

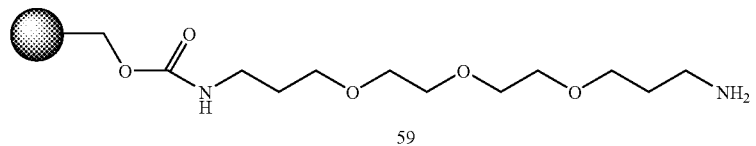
59
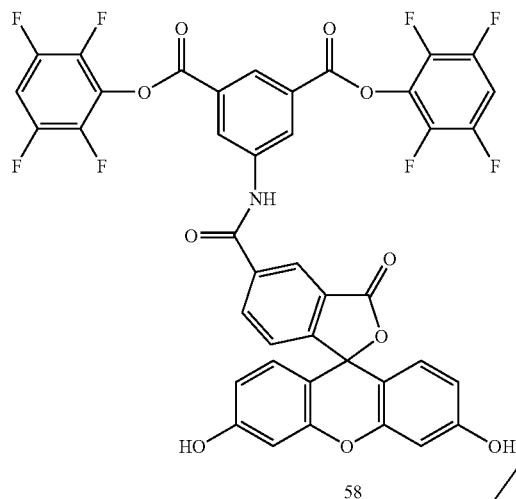
58
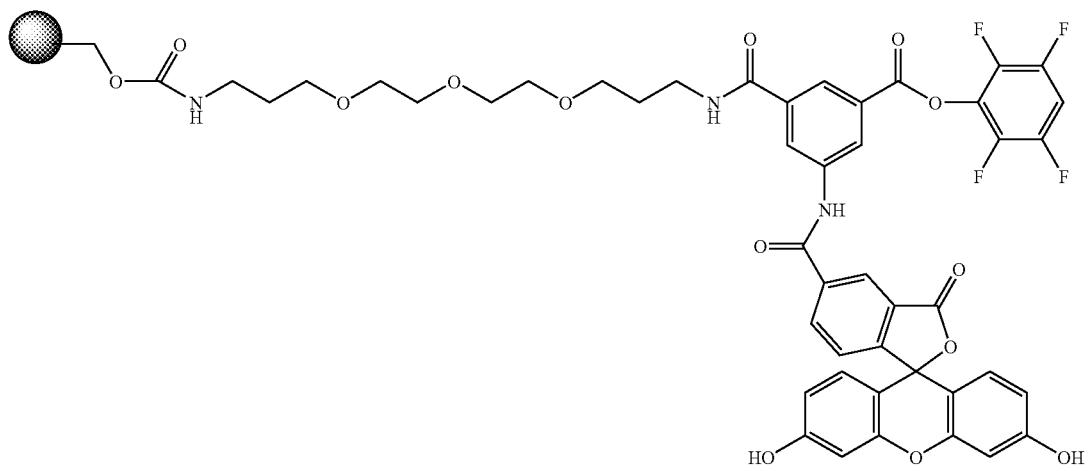
60
Conjugation of polymer supported 60 with a polyamine (e.g., starburst dendrimer, generation 2) to give the adduct 61 can be achieved as depicted below.

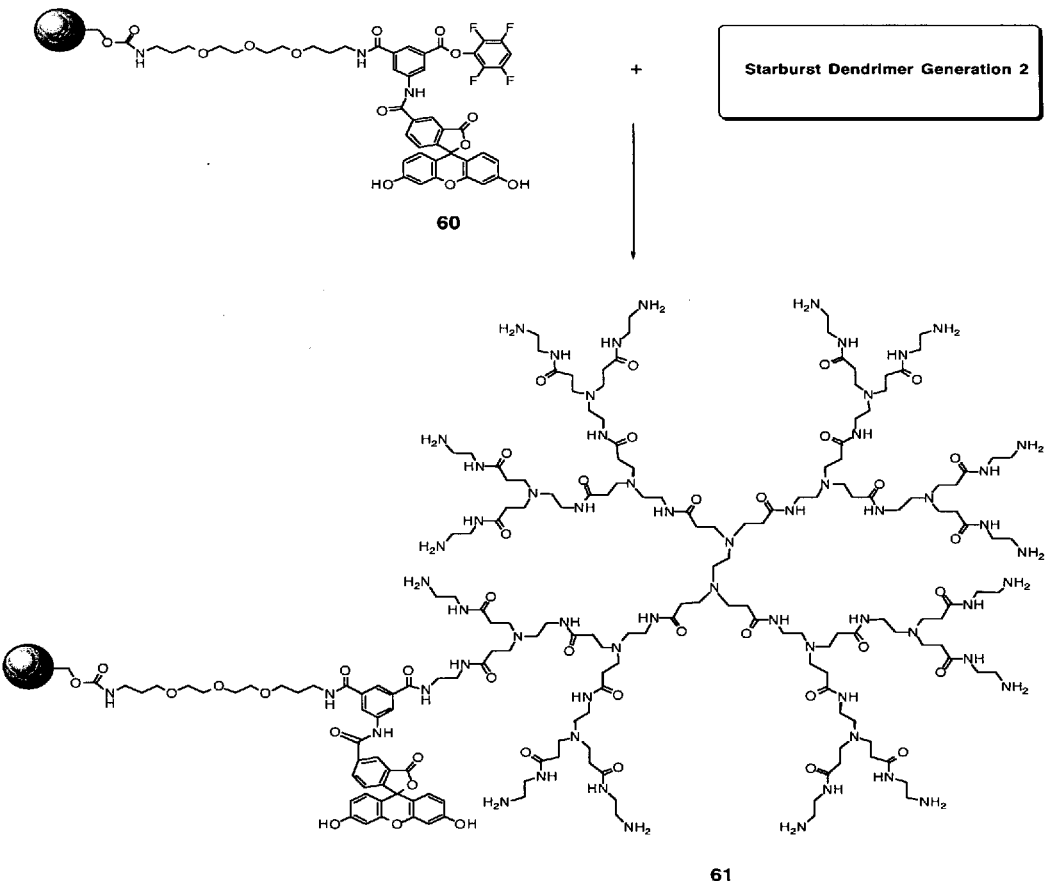

Perbiotinylation with the biotin-aspartate isothiocyanate derivative 46, can be readily accomplished to yield the t-Bu ester protected polymer supported compound 62, shown below. Cleavage of the perbiotinylated compound and cleavage of the t-Bu esters is accomplished simultaneously using TFA.

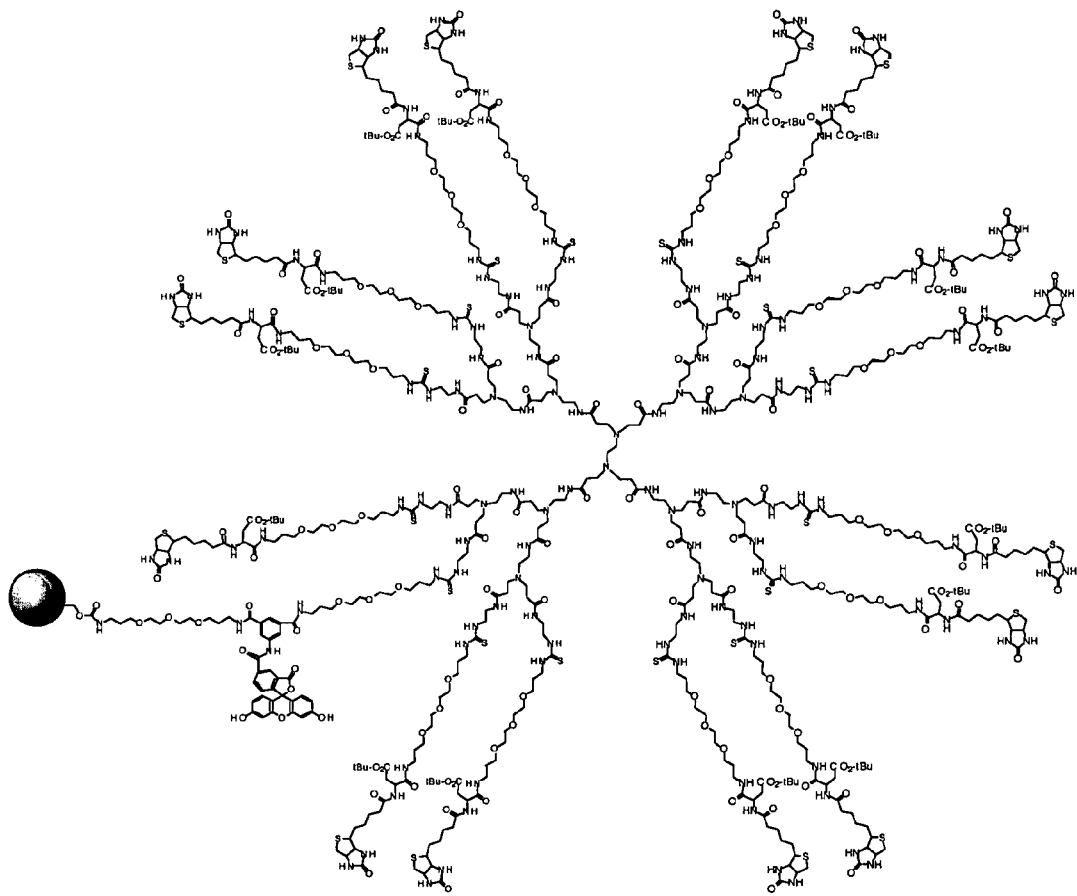
62

Once obtained free of resin, the resulting amine can be converted to a conjugation moiety, such as the isothiocyanate, 63, as shown below, or it may be conjugated directly to another molecule.

103 104
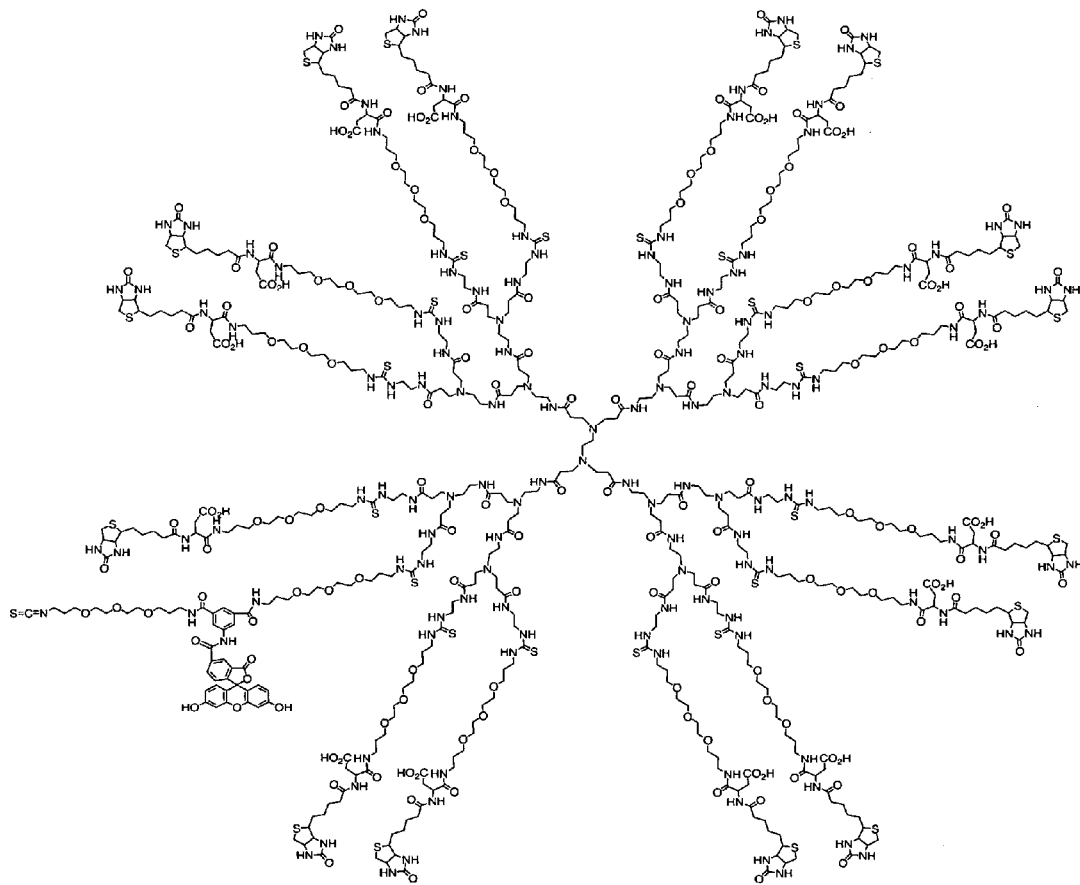
63

General Experimental Detail for Examples 17–21:

All reactions were monitored by HPLC. Compound purity was assessed on a HPLC system that contained a Hewlett-Packard quaternary 1050 gradient pump, a variable wavelength UV detector (254 nm), and a Varex ELSD MKIII evaporative light-scattering detector. Analysis of the HPLC data was conducted using Hewlett-Packard HPLC ChemStation software. Reversed-phase HPLC chromatography was carried out on an Alltech Altima C-18 column (5 μm, 250×4.5 mm) using a gradient solvent system at a flow rate of 1 mL/min. Solvent A in the gradient was methanol. Solvent B was aqueous 1% HOAc. Starting from 40% A, the initial solvent mixture was held for 2 min, then the gradient was increased linearly to 100% A over the next 10 min, and 100% A was held for 5 min. Retention times ($t_R$) are provided with the experimental for the compounds.

$^1$H NMR spectra were on either a Bruker AC-200 (200 MHz) instrument. Chemical shifts are expressed as ppm using tetramethylsilane as internal standard ($\delta$=0.0 ppm).

For the compounds prepared the NMR spectra were consistent with the structures shown.

Mass spectral data (both low resolution and high resolution) of most compounds prepared were obtained on a PerSeptive Biosystems Mariner Electrospray Time of Flight Mass Spectrometer (ESI-TOF). For analysis, the samples were dissolved in 50/50 MeOH/$H_2O$ and were introduced by an integral syringe infusion pump. Some mass spectral data (low resolution) were obtained on a VG Analytical (Manchester, England) VG-70 SEQ mass spectrometer with associated 11250J Data System. Those mass spectral data were obtained by fast atom bombardment (FAB$^+$) in a matrix of 2-hydroxyethyl disulfide (2HEDS) and polyethylene glycol 300 or 600 containing thioglycolate. High-resolution mass spectral data were used for compound identification.

EXAMPLE 17

Experimental for Compounds Shown in Scheme 1

Scheme 1
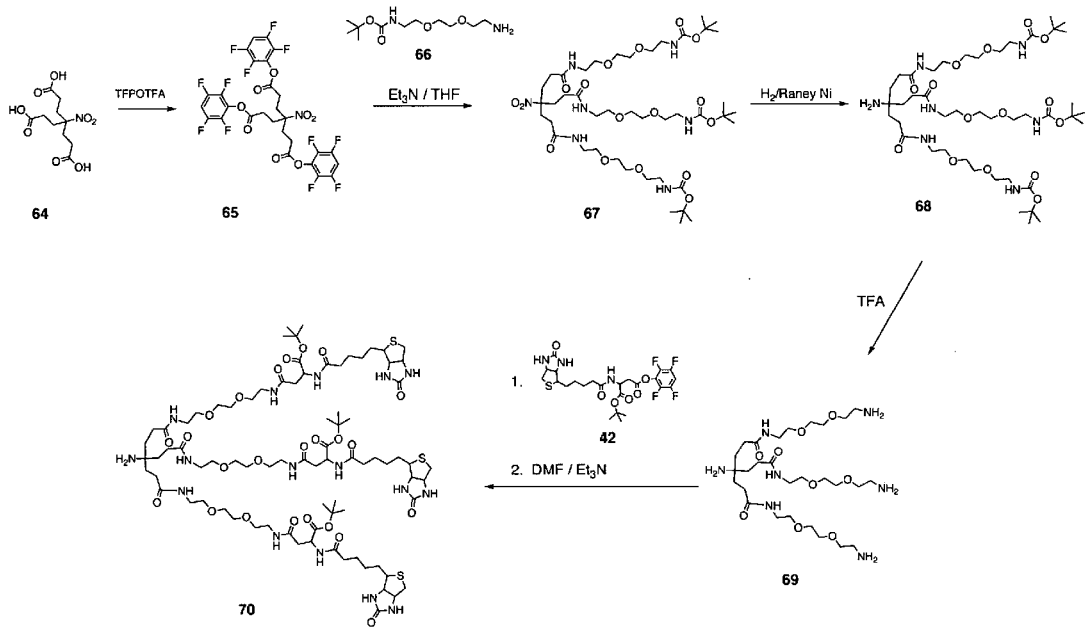

Compound 64

This compound was purchased from Aldrich Chemical Co.

Synthesis of Compound 65

A 5.0 g (18.1 mmol) quantity of nitromethanetripropionic acid, Compound 64, was dissolved in 10 mL of anhydrous DMF under argon atmosphere. The solution was cooled to 0° C. in an ice bath and Et$_3$N (7.29 g, 10.0 mL, 7.22 mmol) was added, followed by 2,3,5,6-tetrafluorophenol trifluoroacetate (18.9 g, 7.22 mmol). The reaction was allowed to warm to room temperature and the mixture was stirred for an additional 30 min. DMF was removed under vacuum. The pale yellow oily residue was stirred with 200 mL of water in an ice bath for 1 h. Filtration collected Compound 65 as a white solid (12.3 g, 17.3 mmol, 96%), m.p. 133.4–134.4° C. $^1$HNMR (CDCl$_3$). HRMS calculated for $C_{28}H_{15}F_{12}NO_8Na$ (M+Na): 744.0504. Found: 744.0518. HPLC: $t_R$=15.1 min.

Synthesis of Compound 66

This compound was prepared as previously described for the preparation of N-Boc-4,7,10-trioxatridecane-13-diamine (page 29, line 10).

Synthesis of Compound 67

A 2.10 g (8.4 mmol) quantity of Compound 66 was dissolved in 50 mL of THF. The solution was cooled to −78° C., and then Compound 65 (2.0 g, 2.8 mmol) was added followed by Et$_3$N (0.85 g, 1.16 mL, 8.4 mmol). The reaction mixture was stirred at −78° C. for 2 h. Then, it was allowed to warm to room temperature gradually while stirring for an additional 16 h. THF was removed under vacuum. The residue was dissolved in 100 mL of EtOAc, washed with 1N HCl (2×50 mL), saturated NaHCO$_3$ (3×50 mL), water (100 mL), and brine (100 mL). The organic phase was dried and concentrated to afford 2.70 g (2.8 mmol, 100%) of 67 as a yellow oily residue. $^1$HNMR(CDCl$_3$). HRMS calculated for $C_{43}H_{83}N_7O_{17}$ (M+H$^+$): 968.5776. Found: 968.5776. HPLC: $t_R$=13.3 min.

Synthesis of Compound 68

Compound 67 (7.85 g, 8.1 mmol) was dissolved in 250 mL of absolute ethanol and a 50% Raney-Ni in water slurry (31.4 g) was added to that solution. The solution was placed on Parr Hydrogenation apparatus and agitated under hydrogen atmosphere (45 psi) overnight. The catalyst was removed by filtration through celite. The solvent was removed under vacuum to afford 6.5 g (7.0 mmol, 86%) of 68 as a pale yellow oil. $^1$HNMR (CDCl$_3$). HRMS calculated for $C_{43}H_{84}N_7O_{15}$ (M+H$^+$): 938.6025 Found: 938.6003. HPLC: $t_R$=10.5 min.

Synthesis of Compound 69

A 1.70 g (1.82 mmol) quantity of Compound 68 was stirred in 5 mL neat TFA for 1 h. The excess TFA was removed under a stream of air, and then the residue was placed under vacuum overnight to afford Compound 69 as a pale yellow oil, which was used for the next reaction without further purification.

Synthesis of Compound 42

This compound was prepared as previously described in *Bioconjugate Chem.* (2000), 11, 569–583.

Synthesis of Compound 70

Compound 65 (1.82 mmol) and Compound 42 (3.07 g, 5.46 mmol) were stirred together in 20 mL of anhydrous DMF. After the reactants dissolved, Et$_3$N (1.10 g, 10.9 mmol) was added to the solution. The mixture was stirred for 30 min while monitoring the reaction by HPLC. After the reaction was complete, the solvent was removed under vacuum to afford a clear pale yellow oily residue. The residue was eluted on a silica gel column (25 cm×4.5 cm) using initially EtOAc/MeOH (50%, 80%), then MeOH to afford Compound 70 (2.207 g, 1.2 mmol, 66.3%) as a colorless oil.

$^1$HNMR(CDCl$_3$). HRMS calculated for $C_{82}H_{141}N_{16}O_{24}S_3$ (M+H$^+$): 1829.9467. Found: 1829.9476. HPLC: $t_R$=9.78 min

EXAMPLE 18

Experimental for Compounds Shown in Scheme 2

Scheme 2
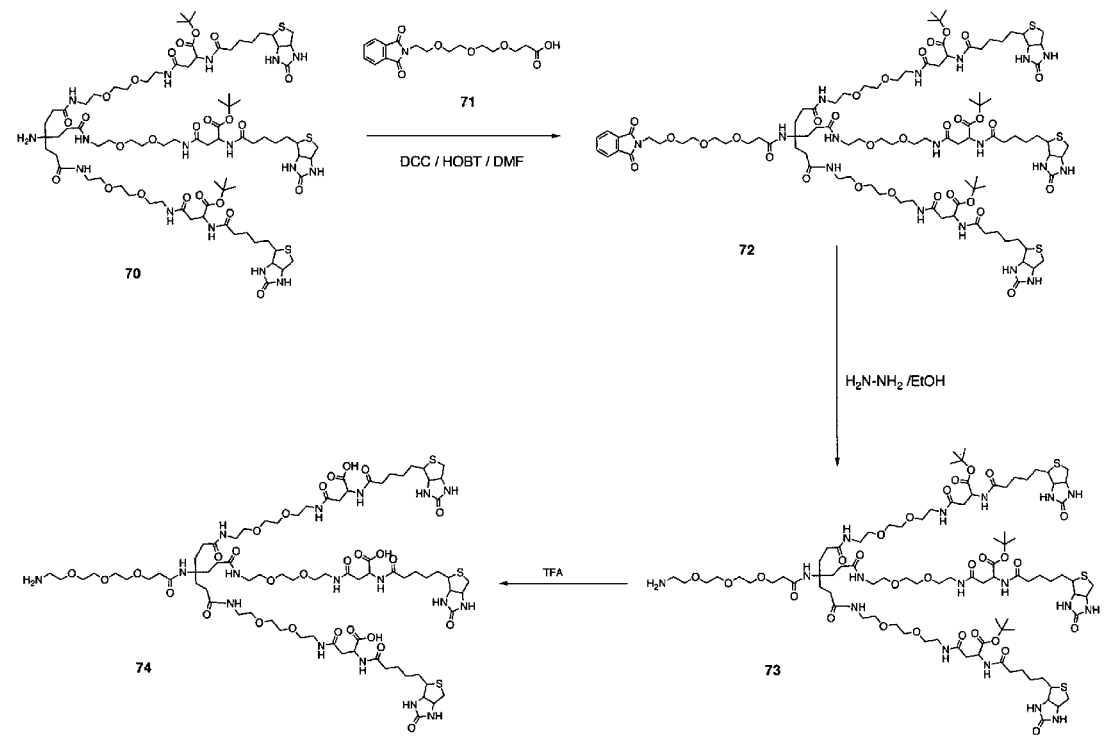

Synthesis of Compound 71

Step a: Sodium (0.10 g, 4.35 mml) was added to a solution of triethyleneglycol (64.0 mL, 0.48 mol) in anhydrous THF (250 mL) at room temperature. tert-Butyl acrylate (24.0 mL, 0.164 mol) was added after the sodium was dissolved. The reaction mixture was stirred at room temperature for 20 h and neutralized with 1.0 N HCl (4 mL). After removal of the solvent, the residue was suspended in brine and extracted with EtOAc (3×70 mL). The combined organic layers were washed with brine and dried over $MgSO_4$. After evaporation of the solvent, the tert-butylacylate adduct (40.23 g, 0.157 mol, 96%) was a colorless oil, which was used directly for the next reaction step without further purification. HPLC: $t_R$=10.2 min.

Step b: The crude product from step a (40.23 g, 0.157 mol) was dissolved in 50 mL pyridine, cooled to 0° C., and Ts-Cl (32.92 g, 0.173 mol) was added slowly. The flask containing the reaction mixture was sealed and placed in a refrigerator at 0° C. for 24 h. The reaction mixture was poured into ice/$H_2O$, and the aqueous layer was extracted with $CH_2C_2$ (3×100 mL). The combined organic layers were washed with 2% HOAc in $H_2O$, and dried over anhydrous $MgSO_4$. The solvent was removed under vacuum to yield the tosylate as colorless oil. The oil was dried under vacuum (52.97 g, mol, 78%). HPLC: $t_R$=13.0 min.

Step c: A 5.0 g (11.6 mmol) tosylate was dissolved in anhydrous DMF (40 mL), and potassium phthalimide (2.78 g, 15.03 mmol) was added. The mixture was heated to 100° C. for 3 h, then allowed to cool to room temperature. The DMF was removed under vacuum to afford a brown oily residue. To the residue was added 150 mL $H_2O$ and the mixture was extracted with EtOAc (3×50 mL). The combined organic layers were washed with brine, dried with $MgSO_4$, and filtered through silica gel (10 cm×2 cm). After evaporation of solvent, the residue was purified by silica gel column chromatography with EtOAc/Hexane (10%, 20%, then 30%). The solvent was removed from fractions containing phthalimide and the residue was washed with 20% EtOAc/Hexane to yield a colorless oil (4.26 g, 10.5 mmol, 90%). HPLC: $t_R$=13.1 min.

Step d: The oil from step c (4.26 g, 0.011 mol) was stirred in neat TFA (5 mL) for 30 min. Excess TFA was removed under a stream of air to afford a colorless oily residue that was purified on a silica gel column (25 cm×2 cm) eluting with EtOAc/hexane (25%, 50%) and EtOAc to yield Compound 71 (1.19 g, 5.7 mmol, 54%) as a colorless oil. HPLC: $t_R$=9.6 min.

Synthesis of Compound 72

A 0.52 g (0.28 mmol) quantity of Compound 70 was stirred with Compound 71 (0.1 g, 5.70 mmol) in 15 mL of anhydrous DMF. DCC (0.07 g, 0.34 mmol) was added to the solution, followed by the addition of catalytic amount of HOBT. The reaction mixture was stirred for 72 h and DMF was removed under vacuum. The residue was purified on a silica gel column (20 cm×2 cm) eluting with EtOAc/hexane (50%, 70%), EtOAc, MeOH/EtOAc (10%, 50%) and MeOH to yield Compound 72 (0.44 g, 83.4%) as a colorless tacky solid. $^1$HNMR($CDCl_3$). LRMS calculated for $C_{99}H_{160}N_{17}O_{30}S_3$ ($M+H^+$): 2163.1 Found: 2163.1. HPLC: $t_R$=12.2 min.

Synthesis of Compound 74

A 0.10 g (0.05 mmol) quantity of Compound 72 was stirred in 1M hydrazine/EtOH solution (1 mL) for 16 h. The mixture appeared thick and cloudy. The solvent was removed under vacuum. A 2 mL quantity of TFA was added and the mixture was stirred for 45 min. The excess TFA was removed under vacuum and the residue was dissolved in 2 mL of MeOH to afford a clear solution. A small amount of $Et_3N$ was added to neutralize the trace amount of TFA remaining, and then the solvent was removed under vacuum. The residue was dissolved in 3 mL of $H_2O$. The resultant white precipitate was removed by filtration. The filtrate was place directly on a Sephadex GP-15 column (45 cm×3 cm) and eluted with $H_2O$. The fractions were monitored by ninhydrin test to detect the free amine of the desired product. Fractions containing the product were combined and the solvent was removed to yield Compound 74 (0.068 g, 78.8%) as colorless tacky solid. $^1$HNMR ($CDCl_3$). LRMS calculated for $C_{79}H_{132}N_{17}O_{28}S_3Na$ ($M-2H^++4Na$): 976.9. Found: 976.9. HPLC: $t_R$=6.56 min.

EXAMPLE 19

Experimental for Compounds Shown in Scheme 3

Scheme 3
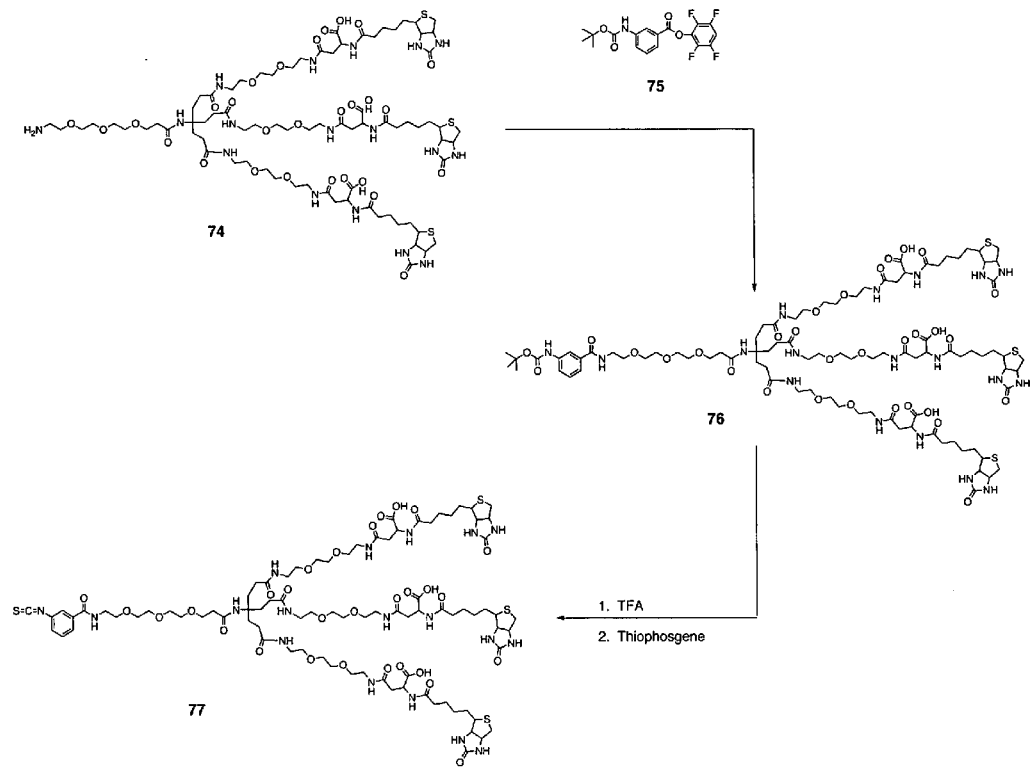

Synthesis of Compound 75

Step A: Di-tert-Butyl carbonate (1.28 g, 58.4 mmol) was added to solution of m-aminobenzoic acid (0.5 g, 36.5 mmol), sodium hydroxide (0.21 g, 51.4 mmol), DMF (10 mL) and water (10 mL) at 0° C. The reaction mixture was allowed to reach ambient temperature while stirring for 16 h. A 6 mL of 1N HCl was added to the solution to bring it to pH 6. The precipitate was collected to yield the tBoc protected aminobenzoic acid (0.5 6 g, 23.6 mmol, 65%) as a white solid. $^1$HNMR (CDCl$_3$). HRMS calculated for $C_{12}H_{19}N_2O_4$ (M+NH$^+$): 255.1345. Found: 255.1356. HPLC: $t_R$=11.9 min.

Step b: A 0.3 g (12.7 mmol) quantity of the solid from step A was dissolved in 10 mL of anhydrous DMF under argon atmosphere. The solution was cooled to 0° C., and Et$_3$N (0.26 g, 25.4 mmol) was added, followed by 2,3,5,6-tetrafluorophenyl trifluoroacetate. The reaction was removed from cooling, and stirred at room temperature for 1.5 h. About half of the DMF was removed under vacuum. The residue was poured into 150 mL of water, and the cloudy mixture was extracted with EtOAc (3×50 mL). The combined organic layers were combined, washed with brine and dried over MgSO$_4$. The EtOAc was removed to afford Compound 75 (0.46 g, 12.1 mmol, 95%) as a yellow-brown greasy solid. $^1$HNMR (CDCl$_3$). HRMS calculated for $C_{18}H_{19}N_2O_4F_4$ (M+NH$^+$): 403.1281. Found: 403.1294. HPLC: $t_R$=5.0 min.

Synthesis of Compound 76

A 0.21 g quantity (0.114 mmol) of Compound 74 was stirred with Compound 75 (0.044 g, 0.114 mmol) in 5 mL of anhydrous DMF. Et$_3$N (0.017 g, 0.172 mmol) was added and the solution was stirred for 2 h. The mixture was then loaded on a gel filtration Sephadex G-15 column (30 cm×2 cm) for purification. The eluted fractions were monitored by UV absorption. The UV absorbing fractions were combined to yield the N-tBoc protected Compound 76 as a colorless tacky solid. $^1$HNMR(CDCl$_3$). LRMS calculated for $C_{91}H_{143}N_{18}O_{31}S_3Na_5$ (M−3H$^+$+5Na): 2194.8. Found: 2194.8. HPLC: $t_R$=10.1 min.

Synthesis of Compound 77

The N-tBoc protected Compound 76 (3.0 mg, 0.0014 mmol) was dissolved in 0.5 mL TFA, and that mixture was stirred for 15 min. The excess TFA was removed under a stream of air. The residue was put under vacuum overnight to afford the free amino compound as a colorless tacky solid. The solid was used directly for the next reaction without further purification. $^1$HNMR(CDCl$_3$). LRMS calculated for $C_{86}H_{135}N_8O_{29}S_3Na_5$ (M−3H$^+$+5Na): 2094.8. Found: 2094.8. HPLC: $t_R$=8.0 min.

The free amino compound (0.0014 mmol) was dissolved in 0.5 mL of water. Thiophosgene (0.81 mg, 0.007 mmol) was dissolved in 0.5 mL of methylene chloride. The two solutions were combined and stirred for 2 h. Excess thiophosgene and solvents were removed under a stream of air, and the residue was placed under vacuum overnight to afford Compound 77 as a white tacky solid. $^1$HNMR (CDCl$_3$). LRMS calculated for $C_{87}H_{130}N_{18}O_{29}S_4Na_8$ (M−6H$^+$+8Na): 2194.8. Found: 2194.8. HPLC: $t_R$=10.8 min.

EXAMPLE 20

Experimental for Compounds Shown in Scheme 4

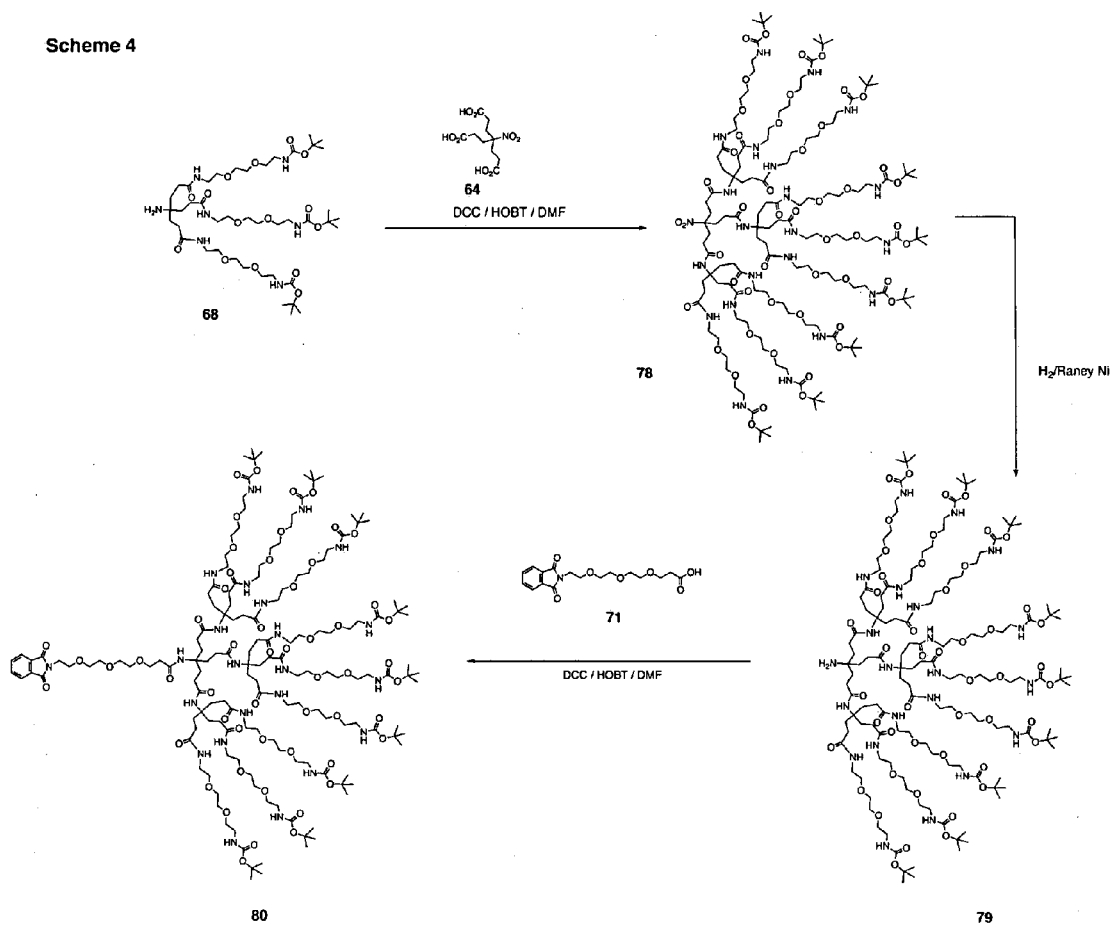
Scheme 4

Synthesis of Compound 78

Compound 64 (0.06 g, 0.22 mmol), 68 (0.67 g, 0.72 mmol) and DCC (0.15 g/0.73 mmol) were stirred in 50 mL of anhydrous DMF. A catalytic amount (6 mg, 0.04 mmol) of HOBT was added and the reaction mixture was stirred for 72 h. The solvent was removed and the residue was purified using preparative TLC (20 cm×20 cm×1 mm), eluting with EtOAc to give Compound 78 (0.67 g, 0.22 mmol, 22%) as pale yellow oil. $^1$HNMR (CDCl$_3$). LRMS calculated for $C_{139}H_{258}N_{22}O_{50}Na_2$ (M+2Na) 3081.8. Found: 3081.8. HPLC: $t_R$=14.9 min.

Synthesis of Compound 79

Compound 78 (0.13 g, 0.044 mmol) was dissolved in 5 mL of absolute ethanol. The solution was mixed with 50% Raney-Ni in a water slurry (0.52 g). The mixture was placed in a Parr Hydrogenation apparatus and was stirred overnight under 40 psi H$_2$. The excess H$_2$ was removed under Ar atmosphere, then the solution was filtered through celite to remove the catalyst. The filtrate was concentrate to afford 79 (0.089 g, 0.03 mmol, 68.3) as an oily residue. $^1$HNMR (CDCl$_3$). LRMS calculated for $C_{139}H_{262}N_{22}O_{48}$ (M+2H$^+$+Na): 3030.0. Found: 3030.0. HPLC: $t_R$=13.0 min.

Synthesis of Compound 80

Compound 79 (0.089 g, 0.030 mmol), 71 (0.010 g, 0.03 mmol) and DCC (0.0088 g, 0.044 mmol) were stirred in 4 mL of anhydrous DMF. A catalytic amount of HOBT (9 mg, 0.07 mmol) was added. The reaction mixture was stirred over a weekend, during which time it became cloudy. The white precipitate was removed by filtration and the solvent was removed from the filtrate by vacuum to afford a pale yellow oily residue. The residue was purified by silica gel column (15 cm×1.5 cm) eluting with EtOAc, MeOH/EtOAc (10%, 50%) and MeOH to afford Compound 80 (0.09 g, 0.027 mmol, 92%) as a colorless tacky oil. $^1$HNMR(CDCl$_3$). LRMS calculated for $C_{156}H_{279}N_{23}O_{54}$Na (M+Na): 3362.0. Found: 3362.0. HPLC: $t_R$=15.0 min.

EXAMPLE 21

Experimental for Compounds Shown in Scheme 5 and 6

The syntheses of Compounds 81–83 follow methods previously described. Brief prophetic descriptions of methods that can be implemented follow.

Scheme 5
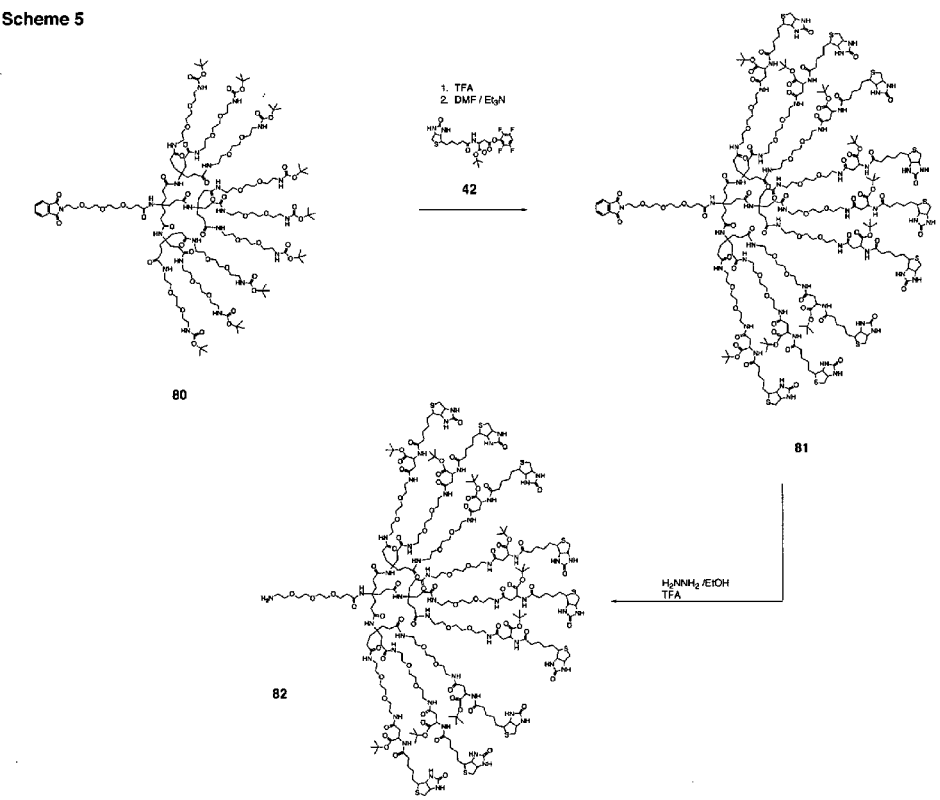

Scheme 6
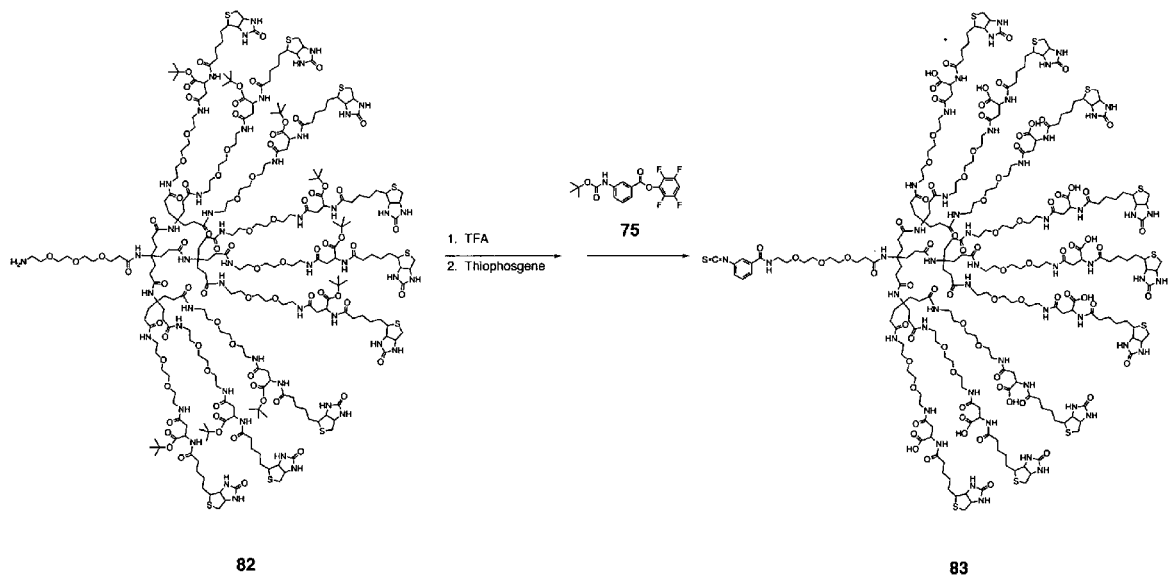

Synthesis of Compound 81

A 0.09 g (0.027 mmol) quantity of Compound 80 can be dissolved in 1 mL TFA and stirred for 30 min. The excess TFA can be removed under a stream of air, and 11 equivalents of Compound 42 added. The reaction mixture can be stirred under Ar at room temperature for 3 days, while monitoring the reaction progress by HPLC. Another 5 equiv. of Compound 42 can be added and the reaction allowed to stir at room temperature for an additional 4 days. The reaction product can be purified by size exclusion chromatography to yield Compound 81 after solvent is removed.

Synthesis of Compound 82

A quantity of Compound 81 can be reacted with hydrazine following the method described for synthesis of Compound 74.

Synthesis of Compound 83

A quantity of Compound 82 can be reacted in TFA for 30 min at room temperature. After the excess TFA is removed under a stream of air, the residue can be dissolved in anhydrous DMF and 1 equivalent of Compound 75 added. The reaction mixture can be stirred at room temperature for 24 h, monitoring progress by HPLC. Following this, the DMF can be removed under vacuum and the residue is dissolved in TFA. The TFA solution can be stirred at room temperature for 30 min and the excess TFA removed under a stream of air. The residue can be dissolved in $H_2O$, and a solution of thiophosgene in methylene chloride added. After stirring for 2 h at room temperature, the excess thiophosgene and solvents can be removed under a stream of air. The isothiocyanate 83 may be used without further purification, except when it is to be stored. Purification can be achieved under neutral conditions using a size exclusion column or filtration apparatus.

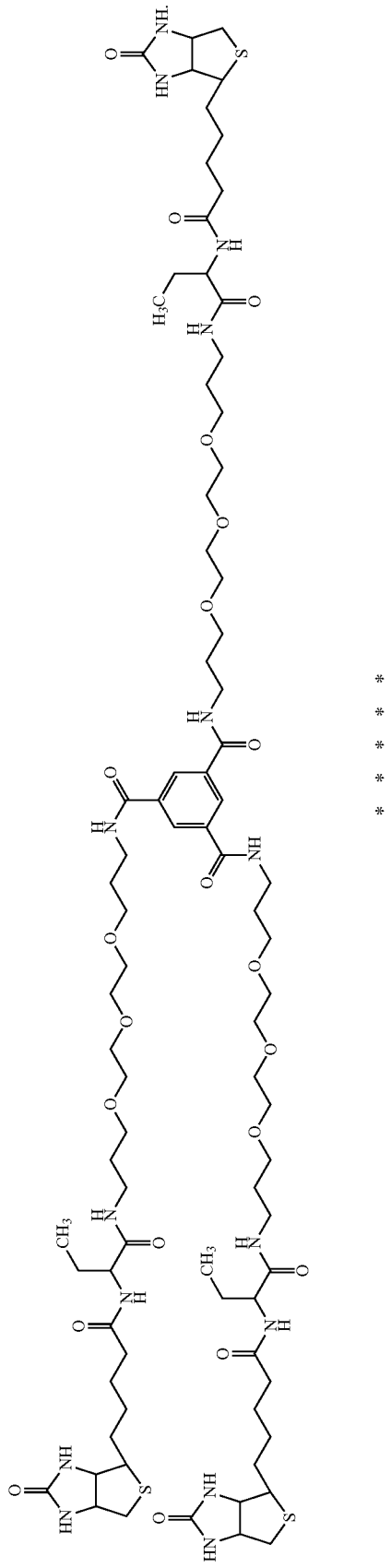

We claim:

1. A composition of matter, which comprises a discrete biotin-containing compound of the general structural formula:

$$C-(L-P-B)_n$$

wherein,
- C is a multifunctional cross-linking moiety having discrete size and containing n substituents, which are reactive, or can be made reactive, with L;
- L is a water-soluble linker moiety of discrete size containing 6 to 50 atoms in length and is one or more of alkyl, heteroalkyl, aryl, and heteroaryl linker moieties containing one or more of ethers, hydroxyls, amines, thioethers, thiols, esters, maleimides, iodoacetamides, hydroxyl amines, acyl hydrazines, carboxylic acids, polyphosphoric acids, phenols, sulfonic acids, iodoacetamides, aldehydes, nitrophenylazides, polylysines, ammoniums, amides, ketones, decaboranes, dodedaboranes, boranes, closo-carboranes, or nido-carboranes;
- P is a biotinidase protective group that blocks biotinidase activity and is one or more of α-amino acids, N-methyl moieties, α-alkyl moieties, or aryl moieties;
- B is selected from biotin moieties; and
- n ranges from 3 to 64;

wherein said composition of matter is selected from the group consisting essentially of:

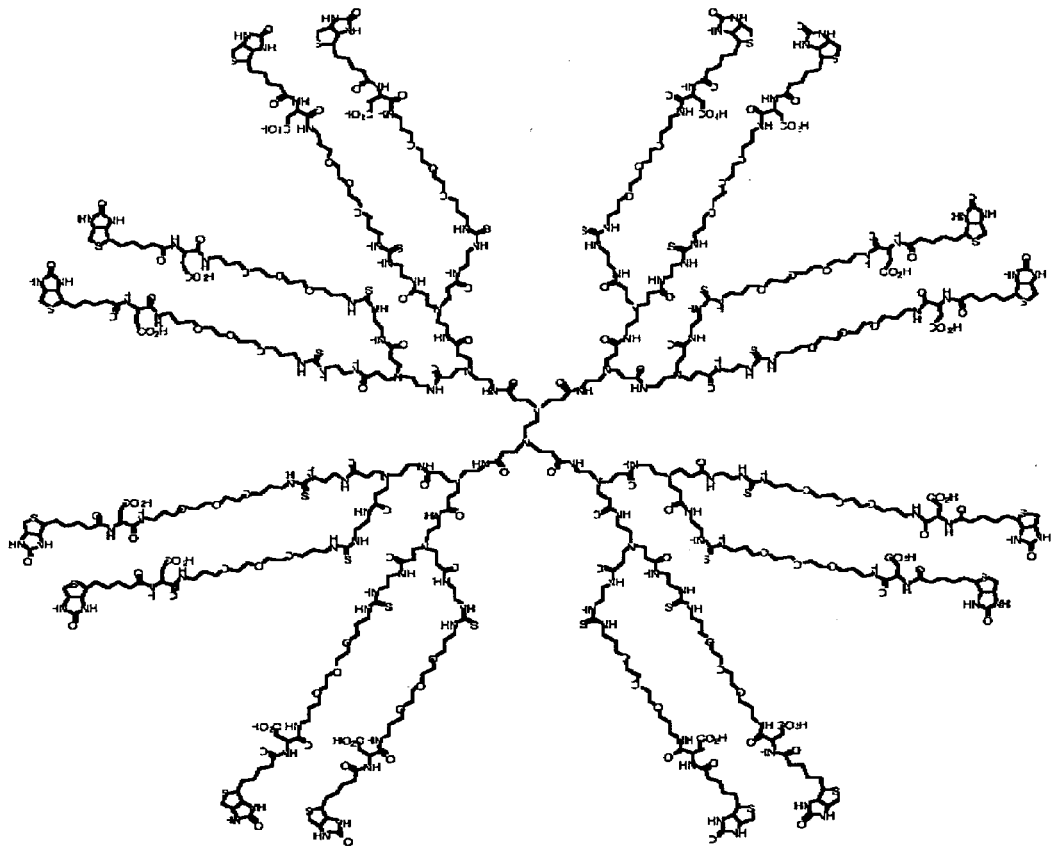

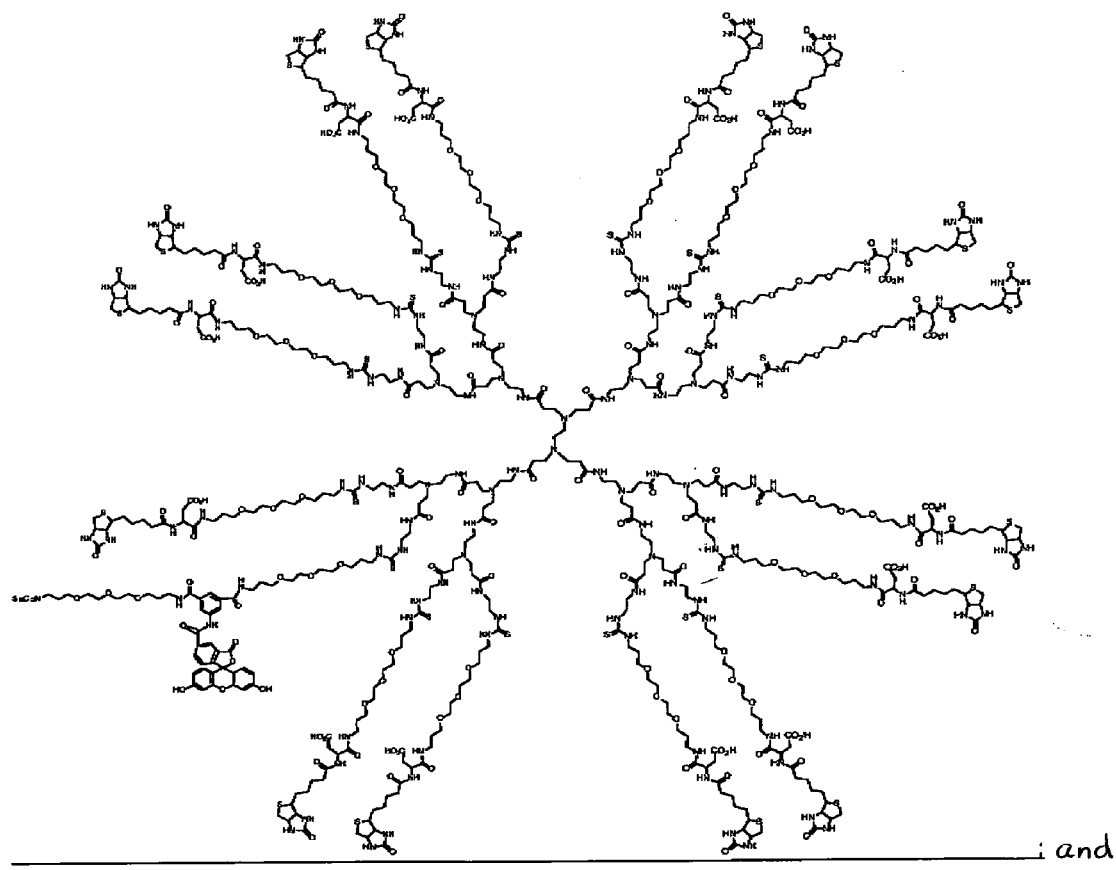
; and

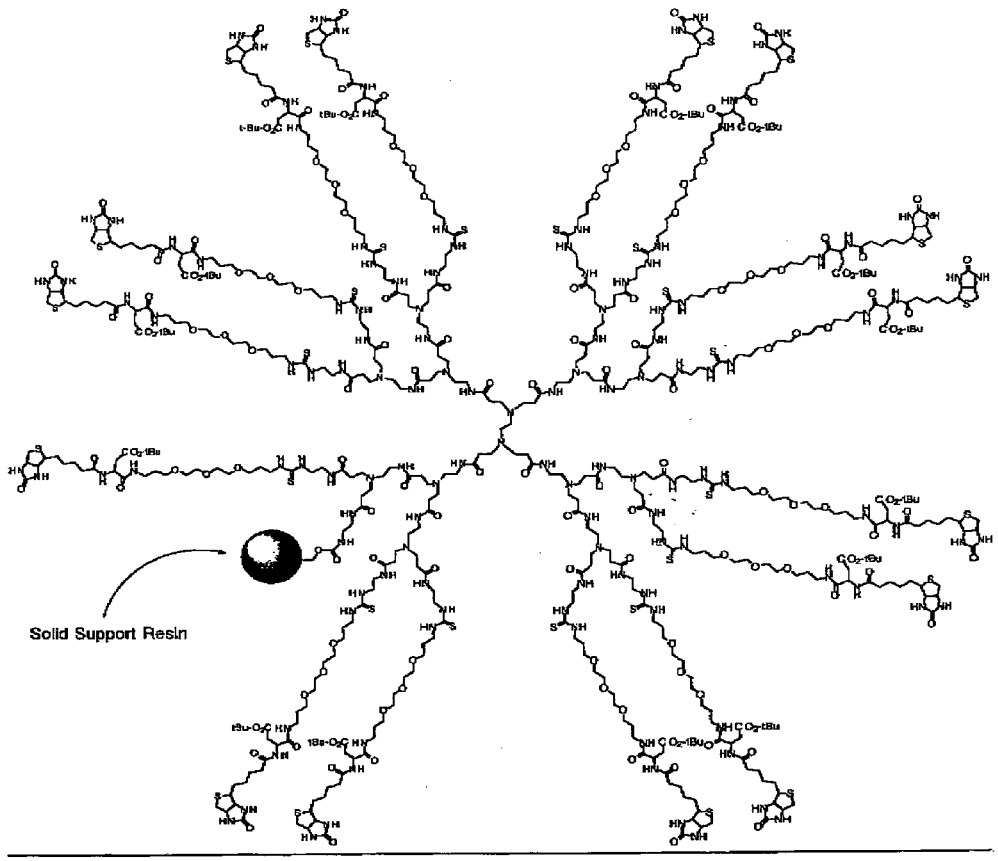

2. A composition of matter, which comprises a discrete biotin-containing compound of the general structural formula:

C-(L-B)$_n$:

wherein
C is a multifunctional cross-linking moiety having discrete size and containing n substituents, which are reactive, or can be made reactive, with L;
L is a water-soluble linker moiety of discrete size containing 6 to 50 atoms in length and is one or more of alkyl, heteroalkyl, aryl, and heteroaryl linker moieties containing ethers, hydroxyls, amines, thioethers, thiols, esters, maleimides, iodoacetamides, hydroxylamines, acyl hydrazines, carboxylic acids, polyphosphoric acids, phenols, sulfonic acids, iodoacetamides, aldehydes, nitrophenylazides, polylysines, ammoniums, amides, ketones, decaboranes, dodedaboranes, boranes, closo- and nido-carboranes;
B is selected from biotin moieties; and
n ranges from 3 to 64;

wherein said composition of matter is selected from the group consisting essential of:

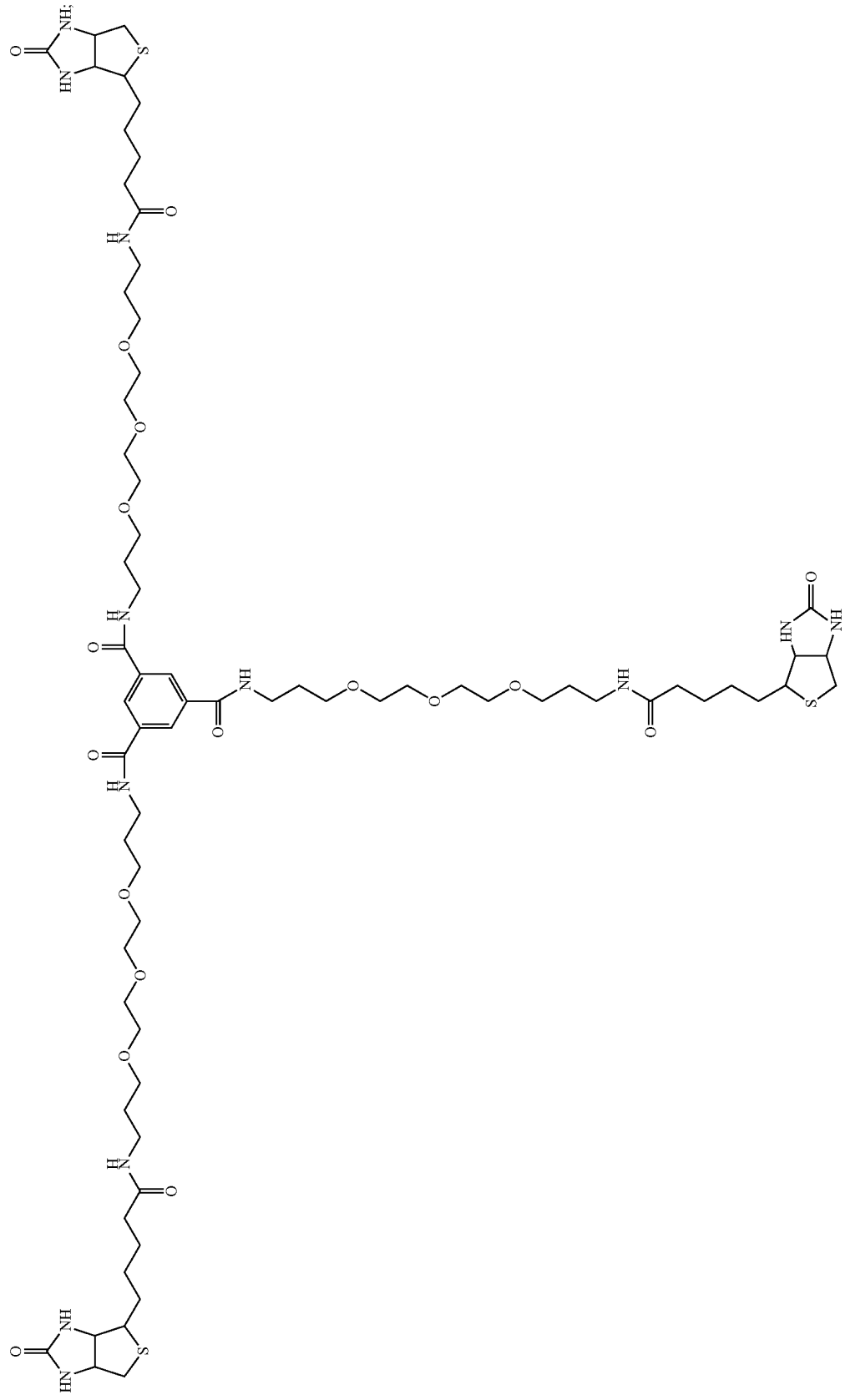

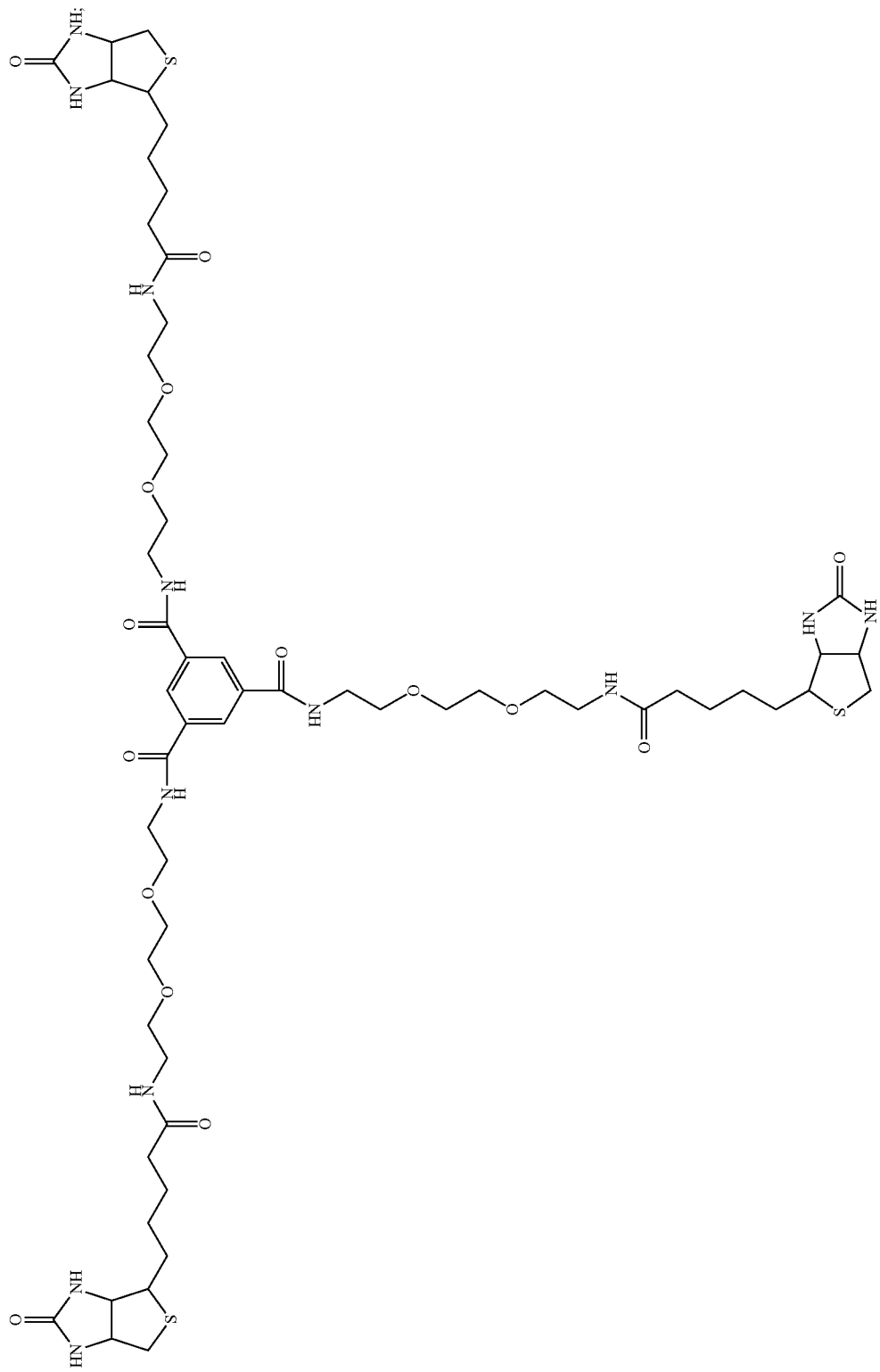

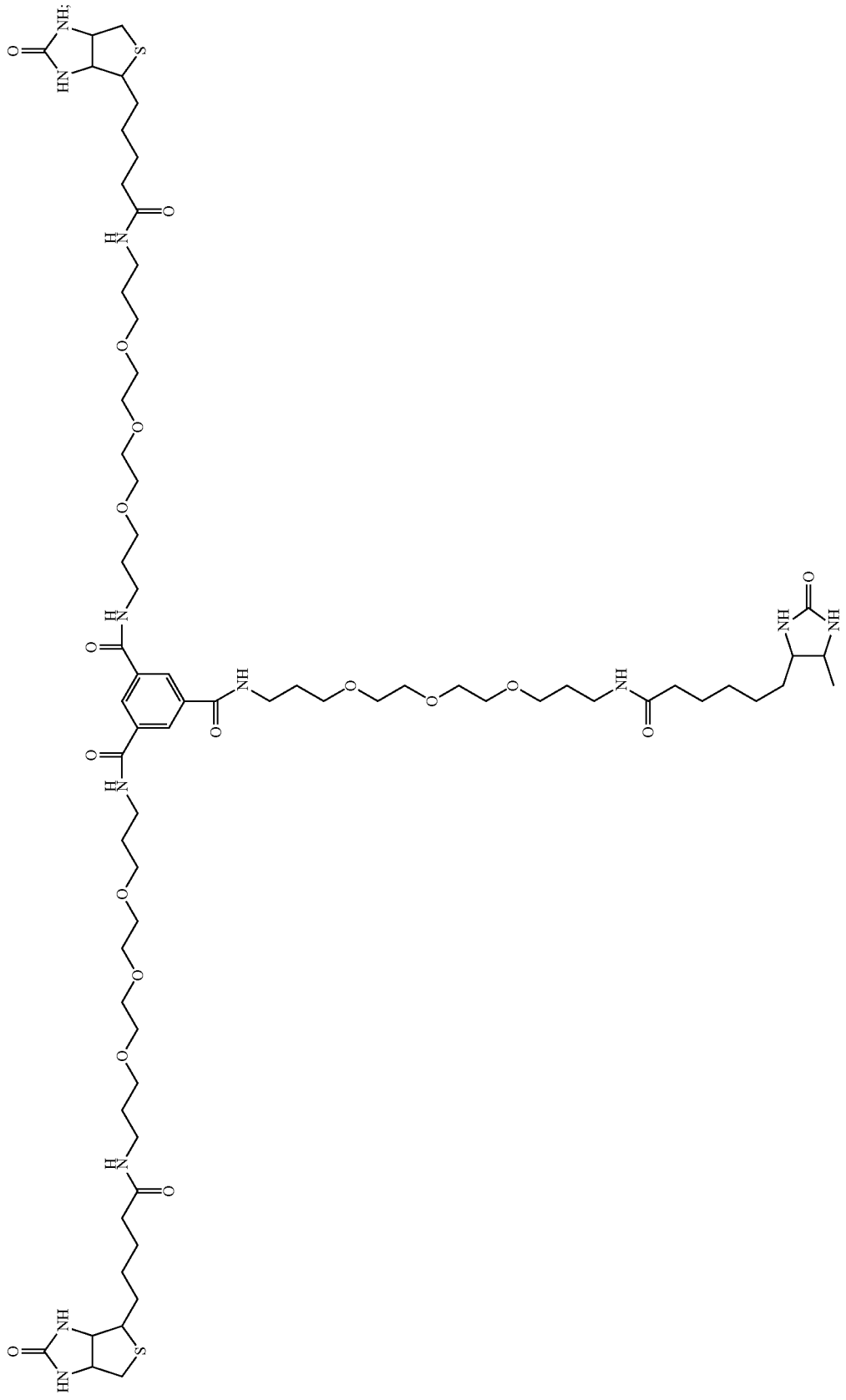

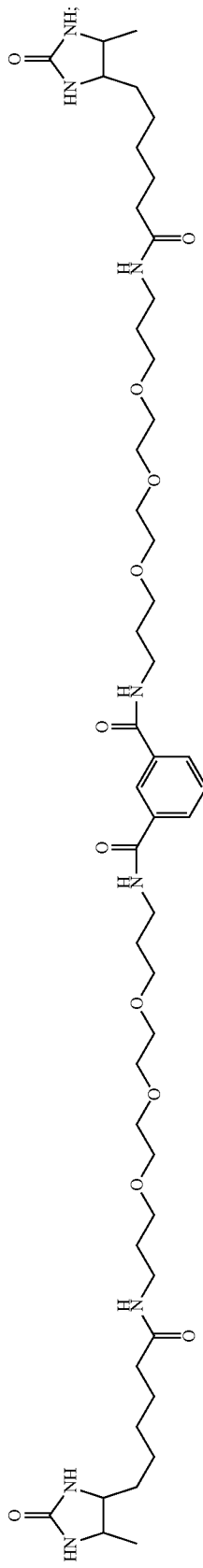
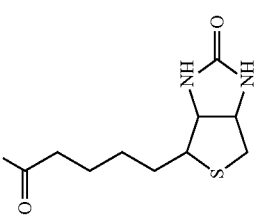

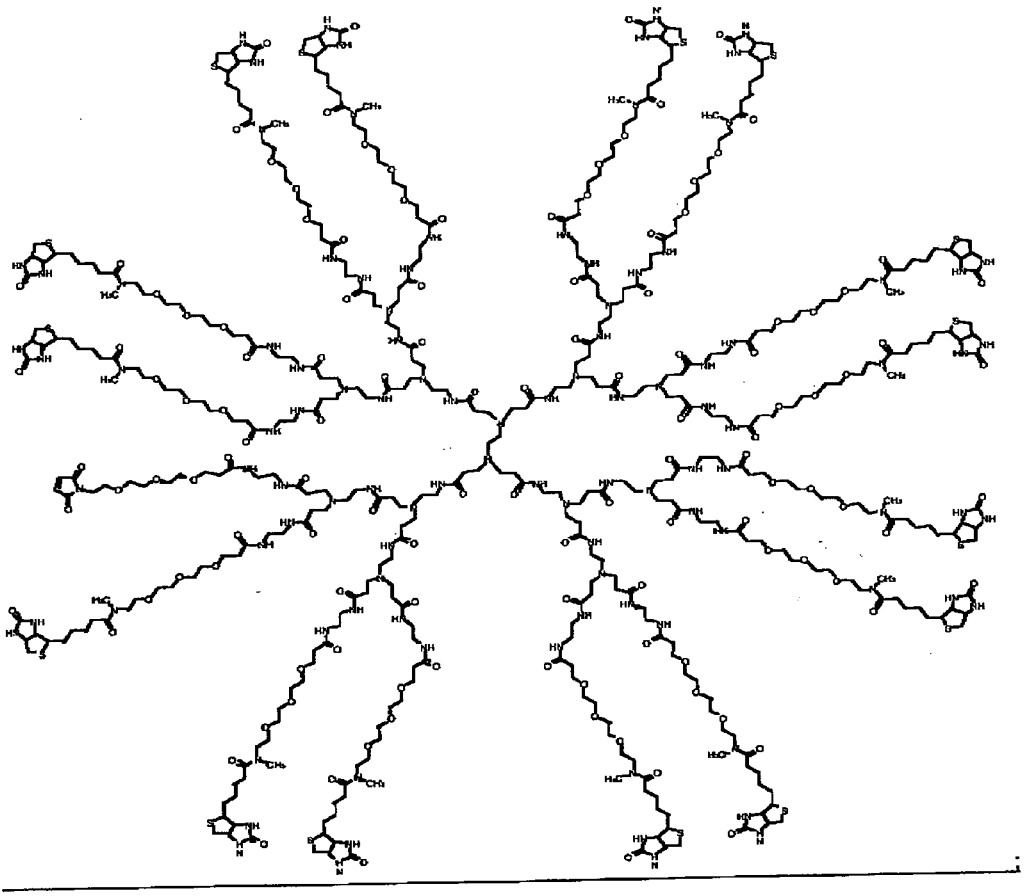

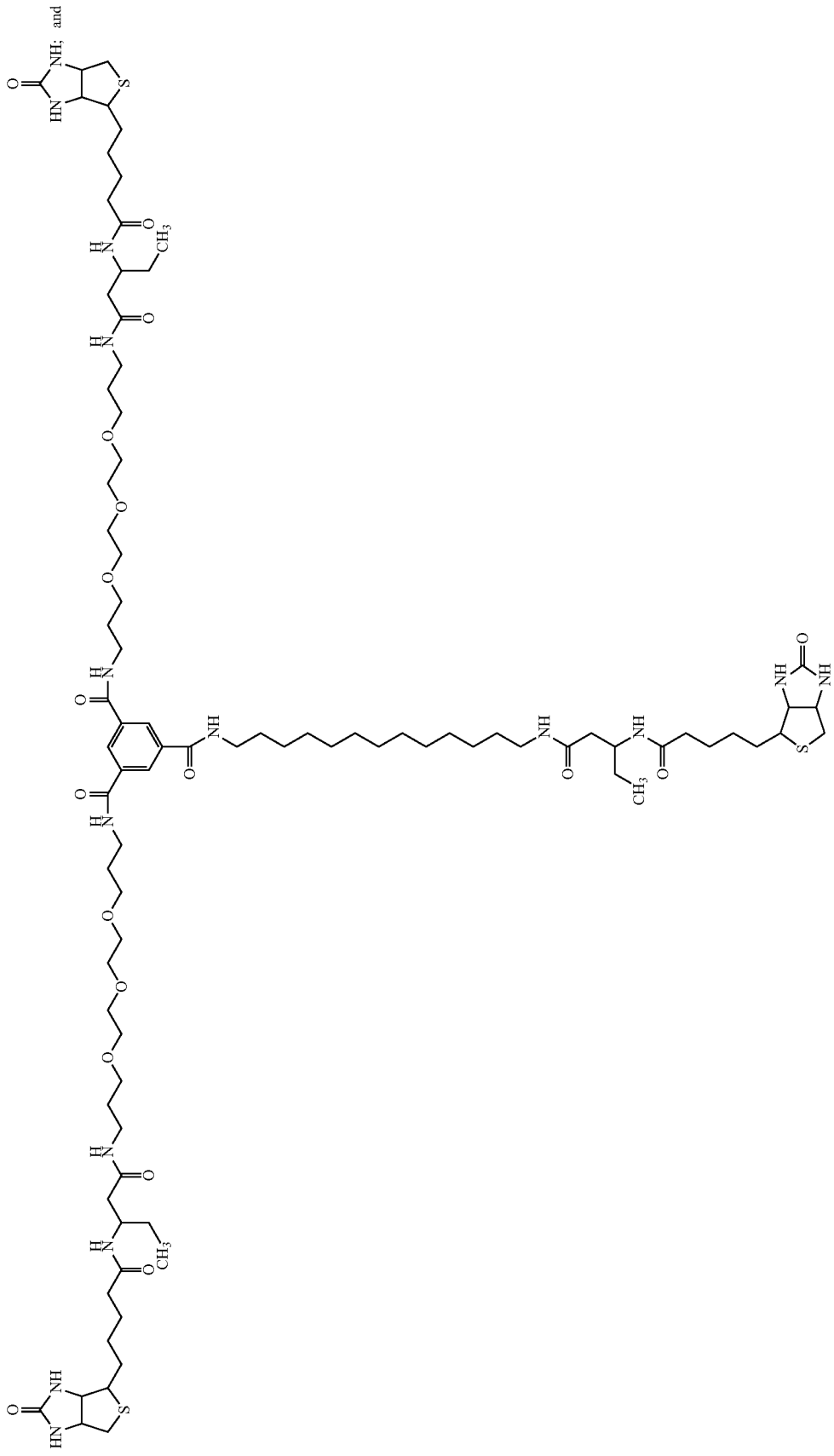

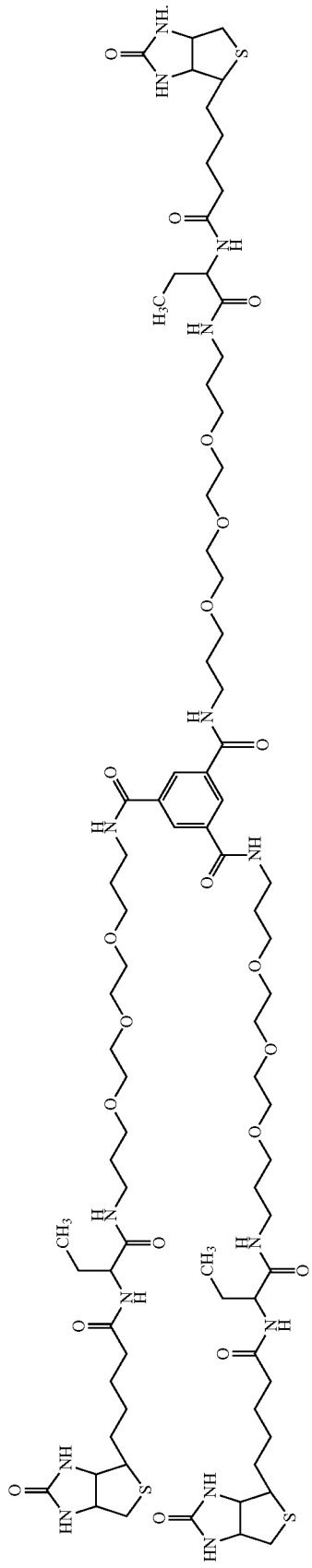

3. The composition of matter of claim 1, which is represent by the following structure:

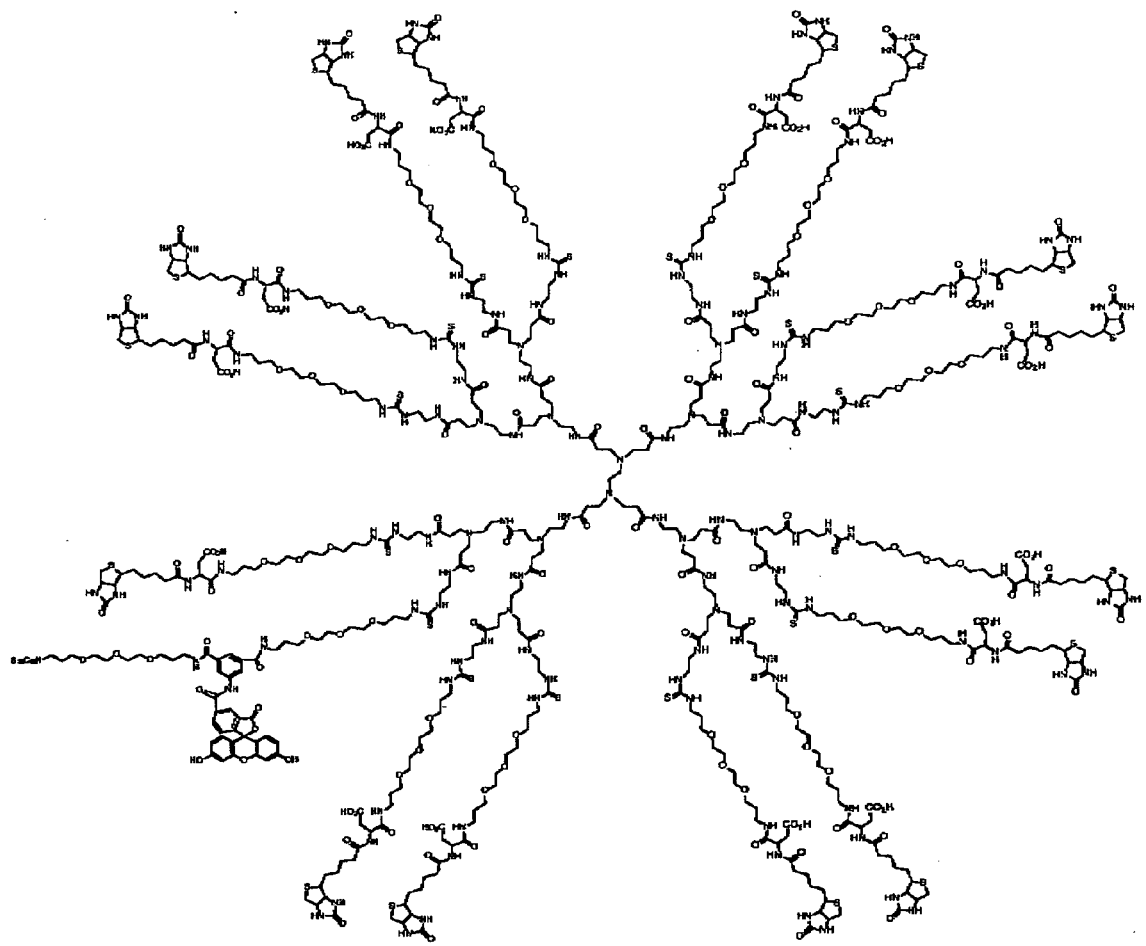

4. The composition of matter of claim 1, which is represented by the following structure:

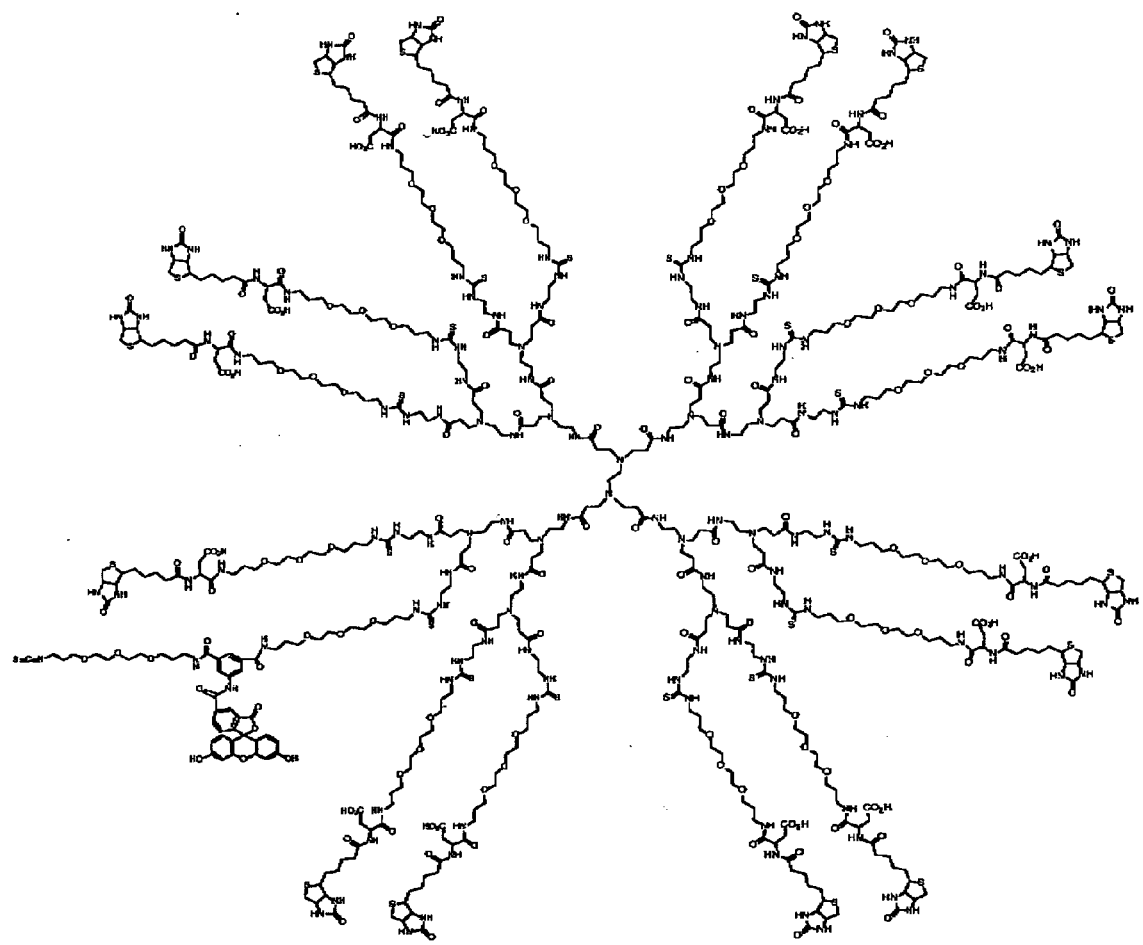

5. The composition of matter of claim 1, which is represented by the following structure:

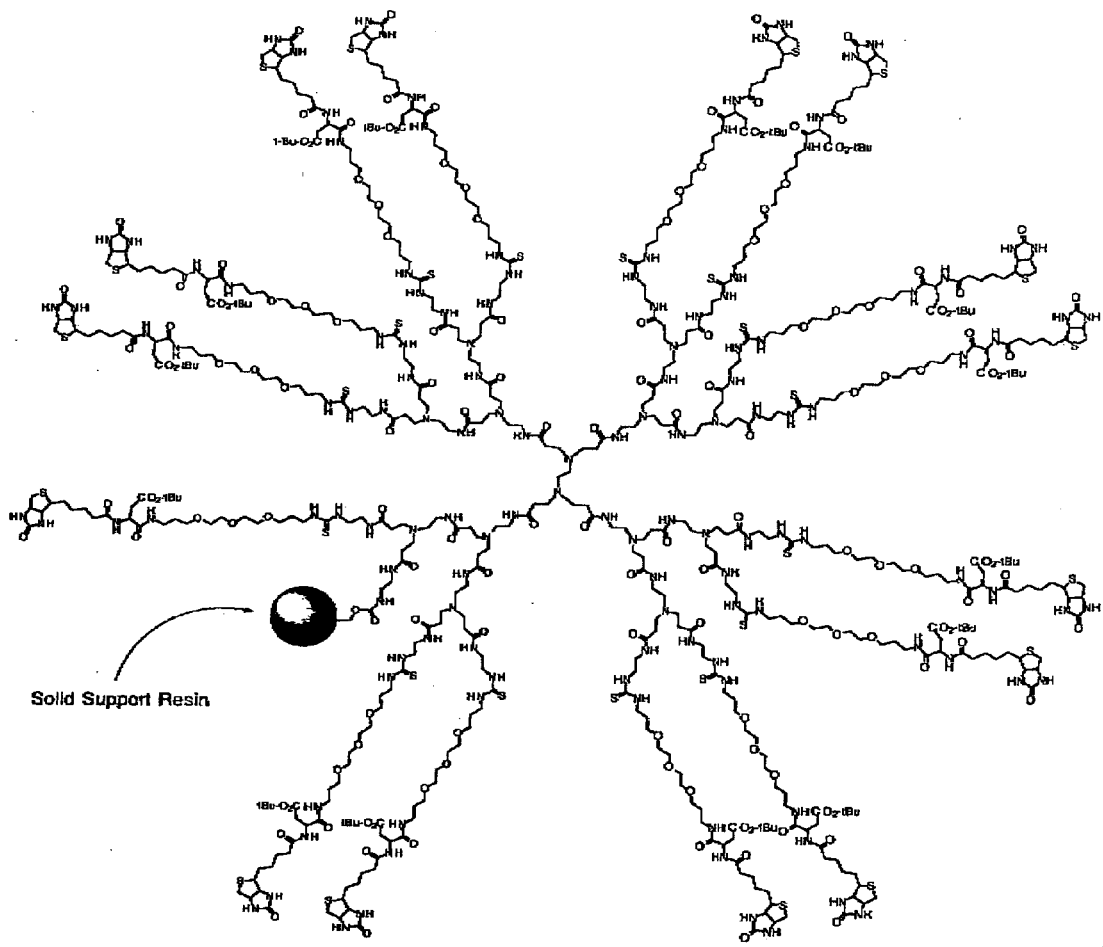

6. The composition of matter of claim 1, wherein
C is benzene tricarboxylic acid,
L is 4,7,10-trioxa-1,13-diamine,
P is aspartate or aspartic acid,
B is biotin, and
n is 3.

7. The composition of matter of claim 2, which is represented by the following structure:

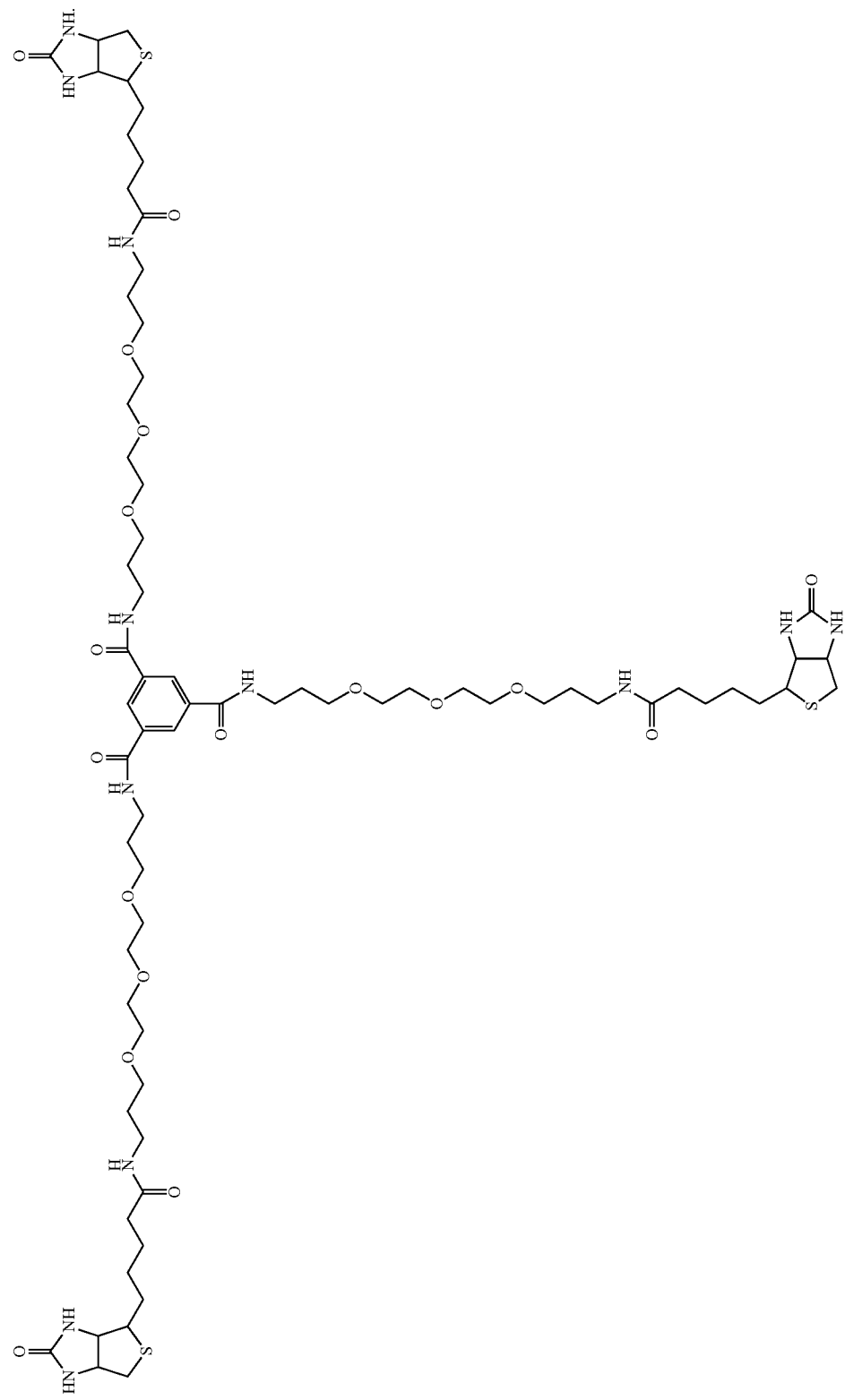

8. The composition of matter of claim 2, which is represented by the following structure:

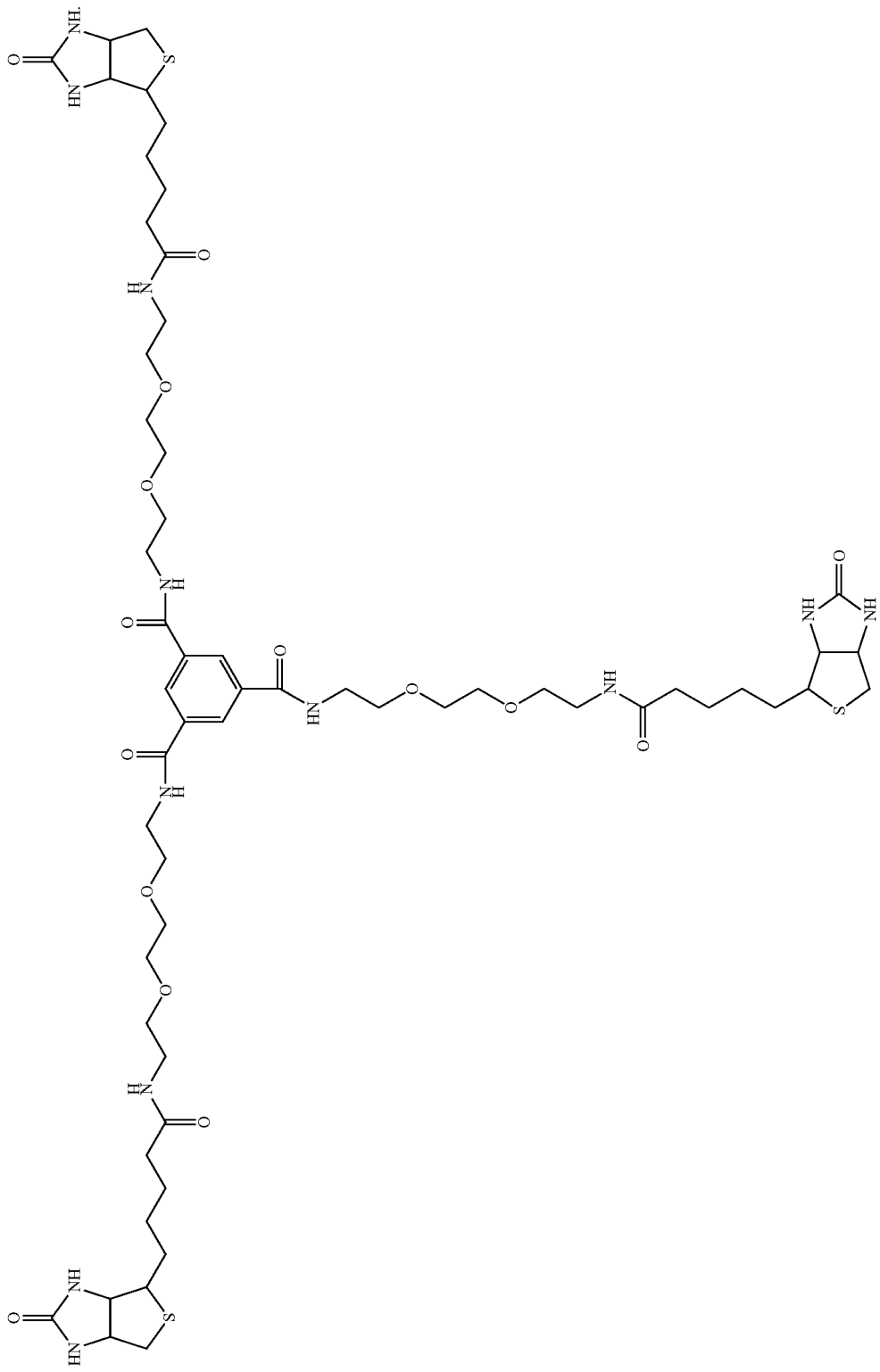

9. The composition of matter of claim 2, which is represented by the following structure:

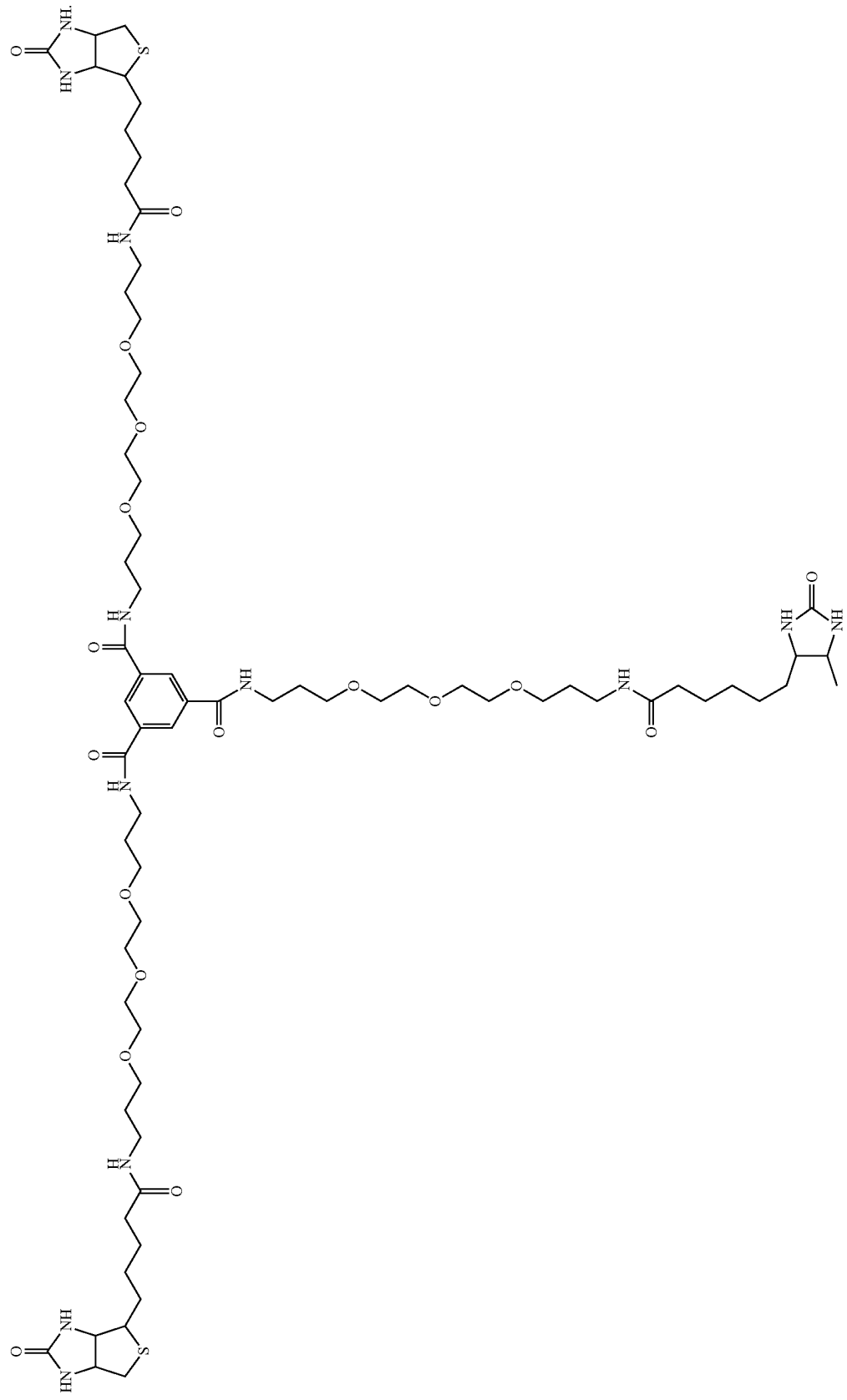

10. The composition of matter of claim 2, which is represented by the following structure:

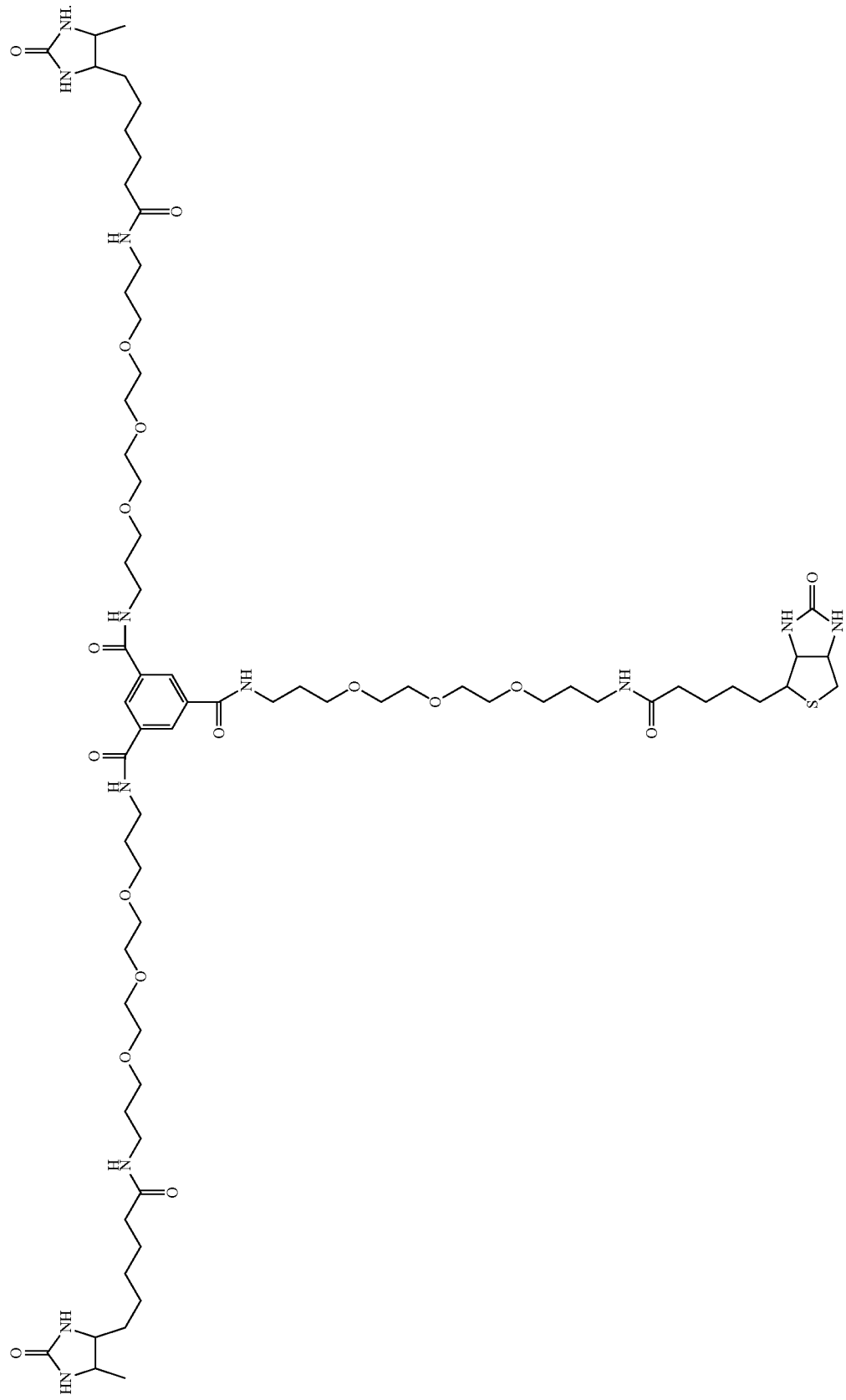

11. The composition of matter of claim 2, which can be represented by the following structure:

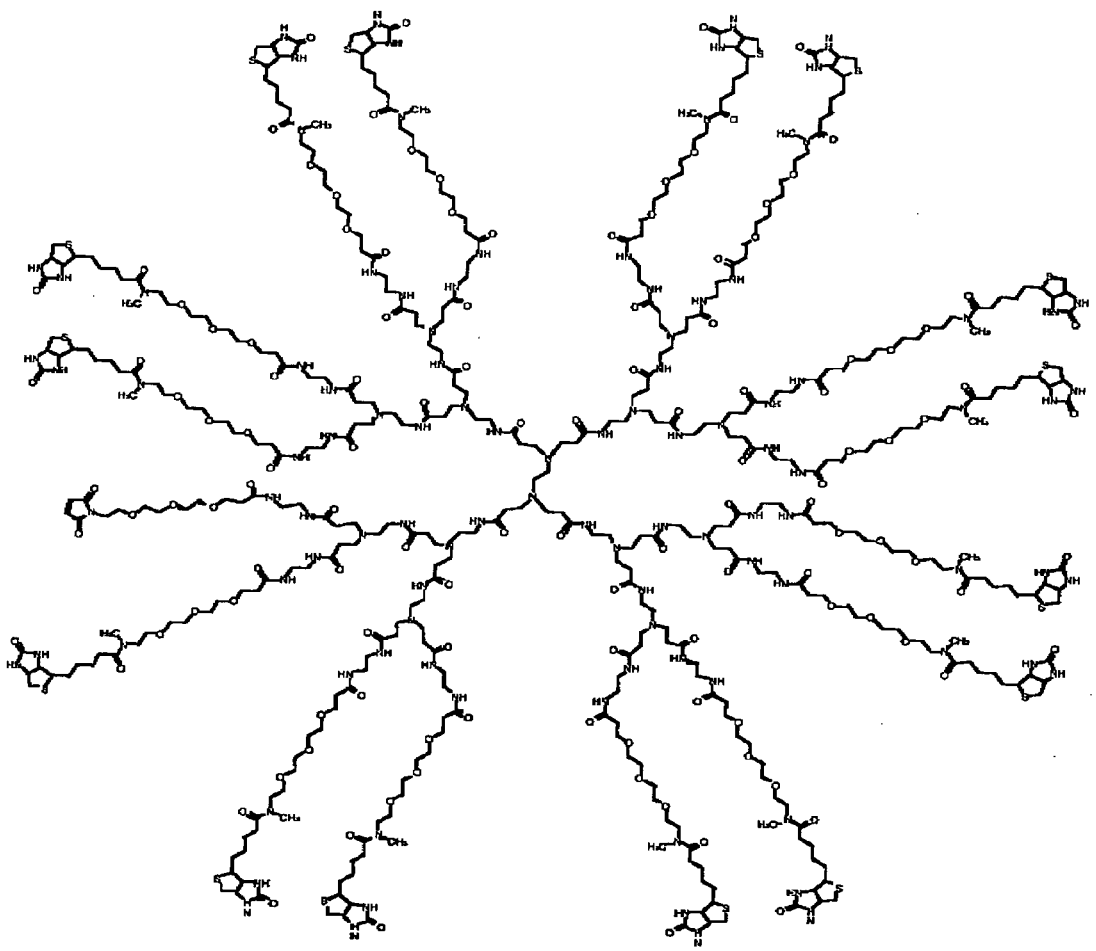

12. The composition of matter of claim 2, which is represented by the following structure:

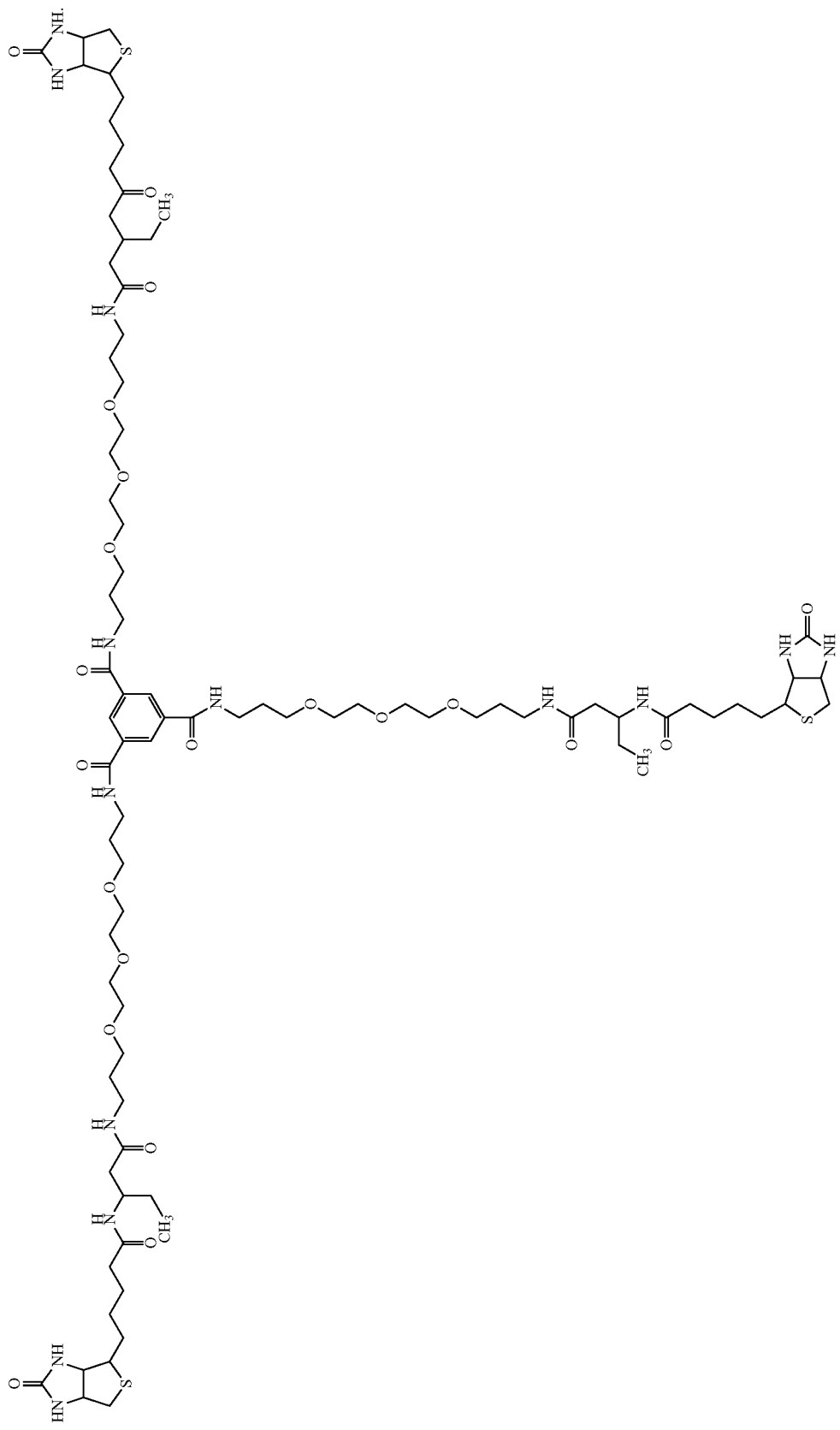

13. The composition of matter of claim 2, which is represented by the following structure: